(12) United States Patent
Liang et al.

(10) Patent No.: US 8,399,646 B2
(45) Date of Patent: Mar. 19, 2013

(54) ISOLATED NUCLEIC ACID ENCODING AN ANTIBODY WHICH SPECIFICALLY BINDS TO PCSK9 AND A HOST CELL THAT PRODUCES THE ANTIBODY

(75) Inventors: Hong Liang, San Francisco, CA (US); Yasmina Noubia Abdiche, Mountain View, CA (US); Javier Fernando Chaparro Riggers, San Mateo, CA (US); Bruce Charles Gomes, Ashburnham, MA (US); Julie Jia Li Hawkins, Old Lyme, CT (US); Jaume Pons, San Bruno, CA (US); Yuli Wang, San Diego, CA (US)

(73) Assignees: Rinat Neuroscience Corp., South San Francisco, CA (US); Pfizer Inc., New York, NY (US)

( * ) Notice: Subject to any disclaimer, the term of this patent is extended or adjusted under 35 U.S.C. 154(b) by 0 days.

(21) Appl. No.: 13/225,119

(22) Filed: Sep. 2, 2011

(65) Prior Publication Data

US 2012/0015435 A1 Jan. 19, 2012

Related U.S. Application Data

(62) Division of application No. 12/558,312, filed on Sep. 11, 2009, now Pat. No. 8,080,243.

(60) Provisional application No. 61/096,716, filed on Sep. 12, 2008, provisional application No. 61/232,161, filed on Aug. 7, 2009, provisional application No. 61/235,643, filed on Aug. 20, 2009.

(51) Int. Cl.
*C07H 21/04* (2006.01)
*C12P 21/08* (2006.01)
*C12N 5/07* (2010.01)

(52) U.S. Cl. ............. 536/23.53; 435/69.1; 435/326; 435/329

(58) Field of Classification Search ............... None
See application file for complete search history.

(56) References Cited

U.S. PATENT DOCUMENTS

2009/0142352 A1 6/2009 Jackson et al.
2010/0041102 A1 2/2010 Sitlani et al.

FOREIGN PATENT DOCUMENTS

| WO | WO 01/57081 A2 | 8/2001 |
| WO | WO 2008/057457 | 5/2008 |
| WO | WO 2008/057458 A2 | 5/2008 |
| WO | WO 2008/057459 A2 | 5/2008 |
| WO | WO 2008/133647 A2 | 11/2008 |
| WO | WO 2009/055783 A2 | 4/2009 |

OTHER PUBLICATIONS

Chamov and Ashkanazi, TIBTECH 14: 52-60, 1996.*
Rudikoff et al., Proc. Natl. Acad. Sci. 79: 1979-1983, 1982.*
Wells, 1990, Biochemistry 29:8509-8517.*
Ngo et al., 1994, The Protein Folding Problem and Tertiary Structure Prediction, pp. 492-495.*
Alborn et al., Clin. Chem. 53: 1814-1819, 2007.*
Bottomley, M., et al., "Structural and Biochemical Characterization of the Wild Type PCSK9-EGF(AB) Complex and Natural Familial Hypercholesterolemia Mutants," *The Journal of Biological Chemistry*, 2009, 1313-1323, vol. 284, No. 2.
Chan, J., et al., "A Proprotein Convertase Subtilisin/Kexin Type 9 Neutralizing Antibody Reduces Serum Cholesterol in Mice and Non-human Primates," *Proceedings of the National Academy of Sciences of the United States of America*, 2009, 9820-9825, vol. 106, No. 24.
Cunningham, D., et al., "Structural and Biophysical Studies of PCSK9 and its Mutants Linked to Familial Hypercholesterolemia," *Nature Structural & Molecular Biology*, 2007, 413-419, vol. 14, No. 5.
Frank-Kamenetsky, et al., "Therapeutic RNAi targeting PCSK9 acutely lowers plasma cholesterol in rodents and LDL cholesterol in nonhuman primates," Proceedings of the National Academy of Sciences of the United States, Aug. 2008, pp. 11915-11920, vol. 105, No. 33.
Graham, "Antisense inhibition of proprotein convertase subtilisin/kexin type 9 reduces serum LDL in hyperlipidemic mice," *Journal of Lipid Research*, Apr. 2007, pp. 763-767, vol. 48, No. 4.
Grefhorst, A., et al., "Plasma PCSK9 Preferentially Reduces Liver LDL Receptors in Mice," *Journal of Lipid Research*, 2008, 1303-1311, vol. 49.
Horton et al., "Molecular biology of PCSK9: its role in LDL metabolism," *Trends in Biochemical Sciences*, 2007, pp. 71-77, vol. 32.
International Preliminary Examination Report issued Jun. 30, 2010, for International Patent Application No. PCT/IB2009/053990.
International Preliminary Examination Report issued Dec. 15, 2010, for International Patent Application No. PCT/IB2009/053990.
International Search Report mailed Jun. 1, 2010, for International Patent Application No. PCT/IB2009/053990.
Kwon, H., et al, "Molecular Basis for LDL Receptor Recognition by PCSK9," *Proceedings of the National Academy of Sciences of the United States of America*, 2008, 1820-1825, vol. 105, No. 6.
Lopez, D., Inhibition of PCSK9 as a novel strategy for the treatment of hypercholesterolemia, Drug News & Perspectives, 2008, pp. 323-330, vol. 21.
Lopez, D., "PCSK9: An enigmatic protease," *Biochemica and Biophysica Acta*, 2008, pp. 184-191, vol. 1781.
McNutt M.C., et al., "Antagonism of secreted PCSK9 increases low density lipoprotein receptor expression in HepG2 cells," *Journal of Biological Chemistry*, 2009, pp. 10561-10570, vol. 284.
Official Communication issued Nov. 15, 2010, in connection with International Patent Application No. PCT/IB2009/053990.

(Continued)

*Primary Examiner* — Gyan Chandra
(74) *Attorney, Agent, or Firm* — Pfizer Inc.

(57) ABSTRACT

The present invention provides antagonizing antibodies, antigen-binding portions thereof, and aptamers that bind to proprotein convertase subtilisin kexin type 9 (PCSK9). Also provided are antibodies directed to peptides, in which the antibodies bind to PCSK9. The invention further provides a method of obtaining such antibodies and antibody-encoding nucleic acid. The invention further relates to therapeutic methods for use of these antibodies and antigen-binding portions thereof to reduce LDL-cholesterol levels and/or for the treatment and/or prevention of cardiovascular disease, including treatment of hypercholesterolemia.

14 Claims, 30 Drawing Sheets

OTHER PUBLICATIONS

Pandit, S., et al., "Functional Analysis of Sites within PCSK9 Responsible for Hypercholesterolemia," *Journal of Lipid Research*, 2008, 1333-1343, vol. 49.

Peterson, A., et al, "PCSK9 Function and Physiology," *Journal of Lipid Research*, 2008, 1595-1599, vol. 49.

Written Opinion of the ISA issued May 25, 2010, for International Patent Application No. PCT/IB2009/053990.

Zhang, D., et al., "Structural Requirements for PCSK9-Mediated Degradation of the Low-Density Lipoprotein Receptor," *Proceedings of the National Academy of Sciences of the United States of America*, 2008, 13045-13050, vol. 105, No. 35.

\* cited by examiner

| L1 | L2 | L3 | H1 | H2 | H3 | k$_{off}$ [1/s] | K$_D$ [pM] |
|---|---|---|---|---|---|---|---|
| KASQDVSTAVA 30 | SASYRYT 12 | QQRYSTPRT 31 | GYTFTSYWMH 57 | EINPSNGRTNYNEKFKS 44 | ERPLYAMDY 45 | | 1100 |
| QDVSTAVA 62 | | | | | | | 620000 |
| GGTRVVSTAVA 63 | | | | | | | |
| RGDFVSTAVA 64 | | | | | | | |
| KASQDVSTAVA 30 | SASYRYT 12 | QQRYSTPRT 31 | GYTFTSYYYMH 59 | EINPSNGRTNYNEKFKS 44 | ERPLYAMDY 45 | 9x10$^{-4}$ | |
| | | | | EINPSGGGRTNYNEKFKS 65 | | 1x10$^{-3}$ | |
| | | | | EINPSSSGRTNYNEKFKS 66 | | 1x10$^{-3}$ | |
| | | | | EINPSTGRTNYNEKFKS 67 | | 1x10$^{-3}$ | |
| | | | | EINPSIGRTNYNEKFKS 68 | | 8x10$^{-4}$ | |
| | | | | EINPSDSRTNYNEKFKS 69 | | 1x10$^{-3}$ | |
| | | | | EINPSGNRTNYNEKFKS 70 | | 1x10$^{-3}$ | |
| | | | | EINPSSSRTNYNEKFKS 71 | | 1x10$^{-3}$ | |
| KASQDVSTAVA 30 | SASYRYT 12 | QQRYSTPRT 31 | GYTFTSYYMH 59 | EINPSNGRTNYNEKFKS 44 | ERPLYAMDY 72 | 9x10$^{-4}$ | |
| | | | | | ERPLYAADY 73 | 9x10$^{-4}$ | |
| | | | | | ERPLYAIDY 74 | 3x10$^{-3}$ | |
| | | | | | ERPLYARDY 75 | 5x10$^{-3}$ | |
| | | | | | ERPLYAGDY 76 | 1x10$^{-3}$ | |
| | | | | | ERPLYAKDY 77 | 1x10$^{-3}$ | |
| | | | | | ERPLYAPDY 78 | 7x10$^{-3}$ | |
| | | | | | ERPLYASDY 79 | 8x10$^{-3}$ | |
| | | | | | ERPLYALDY 80 | 1x10$^{-3}$ | |
| | | | | | ERPLYAVDY 81 | 2x10$^{-3}$ | |
| | | | | | ERPLYAWDY 82 | 2x10$^{-3}$ | |
| | | | | | ERPLYAHDY 83 | 9x10$^{-3}$ | |

FIGURE 24B

| L1 | L2 | L3 | H1 | H2 | H3 | $k_{off}$ [1/s] | $K_D$ [pM] |
|---|---|---|---|---|---|---|---|
| KASQDVSTAVA 30 | SASYRYT 12 | QQRYSTPRT 31 | GYTFTSYYMH 59 | EINPSGGRTNYNEKFKS 65 | ERPLYAFDY 84 | $2\times10^{-3}$ | |
| | | | | | ERPLYATDY 85 | $1\times10^{-3}$ | |
| | | QQRFSTPRT 86 | | | ERPLYAMDY 45 | $5\times10^{-4}$ | |
| | | QQRYSDWRT 87 | | | | $2\times10^{-4}$ | |
| | | QQRYSSWRT 88 | | | | $5\times10^{-4}$ | |
| | | QQRYSTART 89 | | | | $4\times10^{-4}$ | |
| | | QQRYSLYRT 90 | | | | $7\times10^{-4}$ | |
| | | QQRYSLWRT 13 | | | | $6\times10^{-4}$ | |
| | | QQRYSFWRT 91 | | | | $4\times10^{-4}$ | |
| | | QQRYSPWRT 92 | | | | $4\times10^{-4}$ | |
| | | QQRYSGWRT 93 | | | | $4\times10^{-4}$ | |
| | | QQRYSIWRT 94 | | | | $4\times10^{-4}$ | |
| | | QQRYSAWRT 95 | | | | $4\times10^{-4}$ | |
| | | QQRYSLFRT 96 | | | | $4\times10^{-4}$ | |
| | | QQRYSTRRT 97 | | | | $4\times10^{-4}$ | |
| | | QQRYSTLYT 98 | | | | $4\times10^{-4}$ | |
| | | QQRYSTWRT 99 | | | | $5\times10^{-4}$ | |
| | | QQRYSLART 100 | | | | $5\times10^{-4}$ | |
| | | QQRYSSERT 101 | | | | $5\times10^{-4}$ | |
| | | QQRYGTART 102 | | | | $5\times10^{-4}$ | |
| | | QQRYSQART 103 | | | | $5\times10^{-4}$ | |
| | | QQRYSLHRT 104 | | | | $6\times10^{-4}$ | |

FIGURE 24C

| L1 | L2 | L3 | H1 | H2 | H3 | $k_{off}$ [1/s] | $K_D$ [pM] |
|---|---|---|---|---|---|---|---|
| | | QQRYSGVRT 105 | | | | $6 \times 10^{-4}$ | |
| | | QQRYSQSRT 106 | | | | $6 \times 10^{-4}$ | |
| | | QQRYSAERT 107 | | | | $6 \times 10^{-4}$ | |
| | | QQRYSQFRT 108 | | | | $6 \times 10^{-4}$ | |
| | | QQRYSSRRT 109 | | | | $4 \times 10^{-4}$ | |
| | | QQRYSCSRT 110 | | | | $3 \times 10^{-4}$ | |
| | | QQRYSTNRR 111 | | | | $4 \times 10^{-4}$ | |
| | | QQRYSRWRT 112 | | | | $4 \times 10^{-4}$ | |
| | | QQRYSPYRT 113 | | | | $4 \times 10^{-4}$ | |
| | | QQRYSYWRT 114 | | | | $5 \times 10^{-4}$ | |
| | | QQRYSGFRT 115 | | | | $5 \times 10^{-4}$ | |
| | | QQRYSYWRT 116 | | | | $5 \times 10^{-4}$ | |
| | | QQRYSFKRT 117 | | | | $5 \times 10^{-4}$ | |
| | | QQRYSARRT 118 | | | | $5 \times 10^{-4}$ | |
| | | QQRYSRYRT 119 | | | | $6 \times 10^{-4}$ | |
| | | QQRYSLQRT 120 | | | | $6 \times 10^{-4}$ | |
| | | QQRYSTSRT 121 | | | | $6 \times 10^{-4}$ | |
| | | QQRYSHART 122 | | | | $6 \times 10^{-4}$ | |
| | | QQRYSKYRT 123 | | | | $6 \times 10^{-4}$ | |
| | | QQRYSQSRT 124 | | | | $6 \times 10^{-4}$ | |
| | | QQRYSTAFT 125 | | | | $6 \times 10^{-4}$ | |
| | | QQRYSTCCT 126 | | | | $6 \times 10^{-4}$ | |
| | | QQRYSTDRT 127 | | | | $7 \times 10^{-4}$ | |
| | | QQRYSEDRT 128 | | | | $7 \times 10^{-4}$ | |

FIGURE 24D

| L1 | L2 | L3 | H1 | H2 | H3 | $k_{off}$ [1/s] | $K_D$ [pM] |
|---|---|---|---|---|---|---|---|
| KASQDVSTAVA 30 | SASYRYT 12 | QQRYVGRT 129 | | | | $7 \times 10^{-4}$ | |
| | | QQRYSLSRT 130 | | | | $7 \times 10^{-4}$ | |
| | | QQRYSLGRT 131 | | | | $7 \times 10^{-4}$ | |
| | | QQRYSRART 132 | | | | $8 \times 10^{-4}$ | |
| | | QQRYSHART 133 | | | | $8 \times 10^{-4}$ | |
| | | QQRYSTPDT 134 | | | | $9 \times 10^{-4}$ | |
| | | QQRYQQPRT 135 | | | | $9 \times 10^{-4}$ | |
| | | QQRYSTPRT 31 | GYTFTSYYMH 59 | EINPSGGRTNYNEKFKS 65 | ERPLYAMDY 45 | $5 \times 10^{-4}$ | |
| | | | | EIQVSGGRTNYNEKFKS 136 | | $9 \times 10^{-4}$ | |
| | | | | EINPWQGRTNYNEKFKS 137 | | $4 \times 10^{-4}$ | |
| | | | | EINPVQGRTNYNEKFKS 138 | | $6 \times 10^{-4}$ | |
| | | | | EISPFGGRTNYNEKFKS 9 | | $2 \times 10^{-4}$ | |
| | | | | EISPYGGRTNYNEKFKS 139 | | $3 \times 10^{-4}$ | |
| | | | | EIQESGGRTNYNEKFKS 140 | | $3 \times 10^{-4}$ | |
| | | | | EISPIGGRTNYNEKFKS 141 | | $4 \times 10^{-4}$ | |
| | | | | EINPEHGRTNYNEKFKS 142 | | $4 \times 10^{-4}$ | |
| | | | | EINPSEGRTNYNEKFKS 143 | | $4 \times 10^{-4}$ | |
| | | | | EINPWMGRTNYNEKFKS 144 | | $5 \times 10^{-4}$ | |
| | | | | EINPQGGRTNYNEKFKS 145 | | $5 \times 10^{-4}$ | |
| | | | | EINPVKGRTNYNEKFKS 146 | | $5 \times 10^{-4}$ | |
| | | | | EIGPWGGRTNYNEKFKS 147 | | $5 \times 10^{-4}$ | |
| | | | | EINPIGGRTNYNEKFKS 148 | | $6 \times 10^{-4}$ | |
| | | | | EIQISGGRTNYNEKFKS 149 | | $7 \times 10^{-4}$ | |

FIGURE 24E

| L1 | L2 | L3 | H1 | H2 | H3 | k_off [1/s] | K_D [pM] |
|---|---|---|---|---|---|---|---|
| KASQDVSTAVA 30 | SASYRYT 12 | QQRYSTPRT 31 | GYTFTSYYMH 59 | EINPQGTRTNYNEKFKS 150 | | $8\times10^{-4}$ | |
| | | | | EINPSGGRTNYNEKFKS 65 | ERPLYAMDY 45 | $5\times10^{-4}$ | |
| | | | | | ERPLYASDS 151 | $2\times10^{-4}$ | |
| | | | | | ERPLYASDR 152 | $2\times10^{-4}$ | |
| | | | | | ERPLYAMDR 153 | $2\times10^{-4}$ | |
| | | | | | ERPLYANDA 154 | $3\times10^{-4}$ | |
| | | | | | ERPLYANDV 155 | $3\times10^{-4}$ | |
| | | | | | ERPLYAHDV 156 | $4\times10^{-4}$ | |
| | | | | | ERPLYASDY 157 | $4\times10^{-4}$ | |
| | | | | | ERPLYASDL 10 | $3\times10^{-4}$ | |
| | | | | | ERPLYASDV 158 | $5\times10^{-4}$ | |
| | | | | | ERPLYASDA 159 | $5\times10^{-4}$ | |
| | | | | | ERPLYANDS 160 | $5\times10^{-4}$ | |
| | | | | | ERPLYATDL 161 | $3\times10^{-4}$ | |
| | | | | | ERPLYASDS 162 | $6\times10^{-4}$ | |
| | | | | | ERPLYANDM 163 | $3\times10^{-4}$ | |
| | | | | | ERPLYAHDL 164 | $4\times10^{-4}$ | |
| | | | | | ERPLYAHDI 165 | $6\times10^{-4}$ | |
| KASQDVSTAVA 30 | SASYRYT 12 | QQRYSTPRT 31 | GYTFTSYYMH 59 | EINPSGGRTNYNEKFKS 65 | ERPLYAMDY 45 | | 1470 |
| | | | | | ERPLYANDV 166 | | 342 |
| | | | | | ERPLYASDY 167 | | 755 |
| | | | | | ERPLYASDL 10 | | 343 |
| | | | | | ERPLYASDR 168 | | 271 |

FIGURE 24F

| L1 | L2 | L3 | H1 | H2 | H3 | k_off [1/s] | K_D [pM] |
|---|---|---|---|---|---|---|---|
| | | | | | ERPLYASDV 169 | | 286 |
| | | | | | ERPLYAHDV 170 | | 385 |
| | | | | | ERPLYANDM 171 | | 413 |
| | | | | | ERPLYAHDL 172 | | 376 |
| | | | | EINPWQGRTNYNEKFKS 173 | | | 1390 |
| | | | | EINPVQGRTNYNEKFKS 174 | | | 439 |
| | | | | EISPYGGRTNYNEKFKS 175 | | | 216 |
| | | | | EISPFGGRTNYNEKFKS 9 | | | 239 |
| | | | | EIGPWGGRTNYNEKFKS 176 | | | 363 |
| | | QQRYSDWRT 177 | | | | | 616 |
| | | QQRYSSWRT 178 | | | | | 728 |
| | | QQRYSAERT 179 | | | | | 345 |
| | | QQRYSLHRT 180 | | | | | 228 |
| | | QQRYSLWRT 13 | | | | | 94 |
| | | QQRYSSERT 181 | | | | | 886 |
| | | QQRYSLQRT 182 | | | | | 497 |
| | | QQRYSTRRT 183 | | | | | 297 |
| | | QQRYSLWRT 13 | | EISPFGGRTNYNEKFKS 9 | ERPLYASDL 10 | | KD at 37C 343 |
| | | QQRYSLWRT 13 | | EISPFGGRTNYNEKFKS 9 | ERPLYASDL 10 | | 384 |
| | | | | EISPFGGRTNYNEKFKS 9 | ERPLYASDL 10 | | 253 |
| | | | | | | | 183 |
| | | QQRYSDWRT 184 | | | ERPLYASDL 10 | | 466 |

FIGURE 24G

| L1 | L2 | L3 | H1 | H2 | H3 | k_off [1/s] | K_D [pM] |
|---|---|---|---|---|---|---|---|
| | | | | | ERPLYASDL 10 | | 703 |
| | | | | | | | KD at 37C |
| | | QQRYSLWRT 13 | | EISPFGGRTNYNEKFKS 9 | ERPLYASDL 10 | | 155 |
| | | | | EISPFGGRTNYNEKFKS 9 | ERPLYASDL 10 | | 79 |
| | | QQRYSRSRT 186 | | EISPYGGRTNYNEKFKS 185 | ERPLYASDL 10 | | 215 |
| KASQDVSTAVA 30 | SASYRYT 12 | QQRYSTPRT 31 | GYTFTSYYMH 59 | | ERPLYASDL 10 | | 621 |
| RASQGISSALA 11 | | | | | ERPLYASDL 10 | | 968 |
| | GASYLHS 186 | | | EINPSGGRTNYNEKFKS 65 | ERPLYAMDY 45 | | 1470 |
| | DASNRAT 187 | | | | | | 1660 |
| | | | | | | | 9890 |
| | | | | | | | 105000 |
| RASQGISSALA 11 | SASYRYT 12 | QQRYSLWRT 13 | GYTFTSYYMH 59 | EISPFGGRTNYNEKFKS 9 | ERPLYASDL 10 | | 7 |

US 8,399,646 B2

SEQUENCE LISTING

```
<160> NUMBER OF SEQ ID NOS: 187

<210> SEQ ID NO 1
<211> LENGTH: 15
<212> TYPE: PRT
<213> ORGANISM: Homo sapiens

<400> SEQUENCE: 1

Asp Thr Ser Ile Gln Ser Asp His Arg Glu Ile Glu Gly Arg Val
1               5                   10                  15

<210> SEQ ID NO 2
<211> LENGTH: 10
<212> TYPE: PRT
<213> ORGANISM: Homo sapiens

<400> SEQUENCE: 2

Gly Arg Asp Ala Gly Val Ala Lys Gly Ala
1               5                   10

<210> SEQ ID NO 3
<211> LENGTH: 9
<212> TYPE: PRT
<213> ORGANISM: Homo sapiens

<400> SEQUENCE: 3

Ala Ser Ser Asp Cys Ser Thr Cys Phe
1               5

<210> SEQ ID NO 4
<211> LENGTH: 6
<212> TYPE: PRT
<213> ORGANISM: Homo sapiens

<400> SEQUENCE: 4

Gly Gly Ser Leu Val Glu
1               5

<210> SEQ ID NO 5
<211> LENGTH: 6
<212> TYPE: PRT
<213> ORGANISM: Homo sapiens

<400> SEQUENCE: 5

Gln Pro Val Gly Pro Leu
1               5

<210> SEQ ID NO 6
<211> LENGTH: 5
<212> TYPE: PRT
<213> ORGANISM: Homo sapiens

<400> SEQUENCE: 6
```

```
His Gly Ala Gly Trp
1               5

<210> SEQ ID NO 7
<211> LENGTH: 5
<212> TYPE: PRT
<213> ORGANISM: Homo sapiens

<400> SEQUENCE: 7

Ala Glu Pro Glu Leu
1               5

<210> SEQ ID NO 8
<211> LENGTH: 5
<212> TYPE: PRT
<213> ORGANISM: Artificial
<220> FEATURE:
<223> OTHER INFORMATION: VARIABLE HEAVY CHAIN CDR

<400> SEQUENCE: 8

Ser Tyr Tyr Met His
1               5

<210> SEQ ID NO 9
<211> LENGTH: 17
<212> TYPE: PRT
<213> ORGANISM: Artificial
<220> FEATURE:
<223> OTHER INFORMATION: VARIABLE HEAVY CHAIN CDR

<400> SEQUENCE: 9

Glu Ile Ser Pro Phe Gly Gly Arg Thr Asn Tyr Asn Glu Lys Phe Lys
1               5                   10                  15

Ser

<210> SEQ ID NO 10
<211> LENGTH: 9
<212> TYPE: PRT
<213> ORGANISM: Artificial
<220> FEATURE:
<223> OTHER INFORMATION: VARIABLE HEAVY CHAIN CDR

<400> SEQUENCE: 10

Glu Arg Pro Leu Tyr Ala Ser Asp Leu
1               5

<210> SEQ ID NO 11
<211> LENGTH: 11
<212> TYPE: PRT
<213> ORGANISM: Artificial
<220> FEATURE:
<223> OTHER INFORMATION: VARIABLE LIGHT CHAIN CDR

<400> SEQUENCE: 11

Arg Ala Ser Gln Gly Ile Ser Ser Ala Leu Ala
1               5                   10

<210> SEQ ID NO 12
<211> LENGTH: 7
<212> TYPE: PRT
<213> ORGANISM: Artificial
<220> FEATURE:
<223> OTHER INFORMATION: VARIABLE LIGHT CHAIN CDR

<400> SEQUENCE: 12

Ser Ala Ser Tyr Arg Tyr Thr
```

-continued

```
<210> SEQ ID NO 13
<211> LENGTH: 9
<212> TYPE: PRT
<213> ORGANISM: Artificial
<220> FEATURE:
<223> OTHER INFORMATION: VARIABLE LIGHT CHAIN CDR

<400> SEQUENCE: 13

Gln Gln Arg Tyr Ser Leu Trp Arg Thr
1               5

<210> SEQ ID NO 14
<211> LENGTH: 214
<212> TYPE: PRT
<213> ORGANISM: Artificial
<220> FEATURE:
<223> OTHER INFORMATION: HUMANIZED L1L3 LIGHT CHAIN

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 444
<212> TYPE: PRT
<213> ORGANISM: Artificial
<220> FEATURE:
<223> OTHER INFORMATION: HUMANIZED L1L3 HEAVY CHAIN

<400> SEQUENCE: 15

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Glu Ile Ser Pro Phe Gly Gly Arg Thr Asn Tyr Asn Glu Lys Phe
     50                  55                  60

Lys Ser Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Arg Pro Leu Tyr Ala Ser Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

```
<210> SEQ ID NO 16
<211> LENGTH: 108
<212> TYPE: PRT
<213> ORGANISM: Mus musculus

<400> SEQUENCE: 16

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Leu Ser
65                  70                  75                  80

Glu Asp Leu Ala Glu Tyr Phe Cys Gln Gln Phe Tyr Ser Tyr Pro Tyr
                85                  90                  95

Thr Phe Gly Gly Gly Thr Lys Leu Glu Ile Lys Arg
            100                 105

<210> SEQ ID NO 17
<211> LENGTH: 108
<212> TYPE: PRT
<213> ORGANISM: Mus musculus

<400> SEQUENCE: 17

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 18
<211> LENGTH: 107
<212> TYPE: PRT
<213> ORGANISM: Mus musculus

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
```

```
                65                  70                  75                  80
Glu Asp Ile Ala Thr Tyr Tyr Cys Gln Gln Tyr Ser Lys Leu Pro Phe
                    85                  90                  95

Thr Phe Gly Ser Gly Thr Lys Leu Glu Ile Lys
            100                 105

<210> SEQ ID NO 19
<211> LENGTH: 108
<212> TYPE: PRT
<213> ORGANISM: Mus musculus

<400> SEQUENCE: 19

Asp Ile Val Met Thr Gln Ser His Lys Phe Met Ser Thr Ser Phe Gly
1               5                   10                  15

Asp Arg Val Ser Ile Thr Cys Lys Ala Ser Gln Asp Val Ser Asn Ala
                20                  25                  30

Leu Ala Trp Tyr Gln Gln Lys Pro Gly His Ser Pro Lys Leu Leu Ile
            35                  40                  45

Phe Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 20
<211> LENGTH: 115
<212> TYPE: PRT
<213> ORGANISM: Mus musculus

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Leu Leu Phe Ala Tyr Trp Gly Gln Gly Thr Leu Val Thr
            100                 105                 110

Val Ser Ala
    115

<210> SEQ ID NO 21
<211> LENGTH: 118
<212> TYPE: PRT
<213> ORGANISM: Mus musculus

<400> SEQUENCE: 21

Gln Val Gln Leu Gln Gln Pro Gly Ala Glu Leu Val Lys Pro Gly Ala
1               5                   10                  15
```

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Arg Pro Leu Tyr Ala Met Asp Tyr Trp Gly Gln Gly Thr
            100                 105                 110

Ser Val Thr Val Ser Ser
            115

<210> SEQ ID NO 22
<211> LENGTH: 123
<212> TYPE: PRT
<213> ORGANISM: Mus musculus

<400> SEQUENCE: 22

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Gly Gly Ile Tyr Tyr Arg Tyr Asp Arg Asn Tyr Phe Asp Tyr
            100                 105                 110

Trp Gly Gln Gly Thr Thr Leu Thr Val Ser Ser
            115                 120

<210> SEQ ID NO 23
<211> LENGTH: 117
<212> TYPE: PRT
<213> ORGANISM: Mus musculus

<400> SEQUENCE: 23

Glu Val Lys Leu Val Glu Ser Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Asn Thr Ser Tyr Leu Asp Ser Leu
50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Lys Phe Ala Ala Met Asp Tyr Trp Gly Gln Gly Thr Ser

Val Thr Val Ser Ser
        115

<210> SEQ ID NO 24
<211> LENGTH: 15
<212> TYPE: PRT
<213> ORGANISM: Artificial
<220> FEATURE:
<223> OTHER INFORMATION: LINKING PEPTIDE

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 642
<212> TYPE: DNA
<213> ORGANISM: Artificial
<220> FEATURE:
<223> OTHER INFORMATION: HUMANIZED LIGHT CHAIN NUCLEOTIDE SEQUENCE

<400> SEQUENCE: 25
gatatacaaa tgacacaatc tccatcctct ctttccgcat cagtcggcga ccgcgtaacc      60
atcacatgta gagcttctca aggcatctcc tccgccctcg catggtacca acaaaaacca     120
ggtaaagccc caaaactcct catatactca gcttcataca gatacaccgg cgtaccctca     180
agattctcag gttcaggctc tggaacagac tttactttca ccatttcatc actccaaccc     240
gaagacatag ctacatatta ctgccaacaa agatacagcc tctggagaac atttggccaa     300
ggaacaaaac tcgagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg     540 ctgagcaaag cagactacga gaaacacaaa gtctacgcct gcgaagtcac ccatcagggc     600
ctgagctcgc ccgtcacaaa gagcttcaac aggggagagt gt                       642

<210> SEQ ID NO 26
<211> LENGTH: 1332
<212> TYPE: DNA
<213> ORGANISM: Artificial
<220> FEATURE:
<223> OTHER INFORMATION: HUMANIZED HEAVY CHAIN NUCLEOTIDE SEQUENCE

<400> SEQUENCE: 26
caagttcaac tcgttcaatc tggagcagaa gtaaaaaaac ctggcgcctc tgttaaagta      60
agttgtaaag catccggtta cacattcaca tcatattaca tgcattgggt aagacaagcc     120
cctggacaag gactcgaatg gatgggtgaa atctctcctt ttggcggccg aacaaactat     180
aatgaaaaat ttaaatcccg cgtaactatg acccgagaca catccacatc tactgtttat     240
atggaacttt cctcactgcg ttctgaagac actgctgttt attactgtgc acgcgaaaga     300
cctctctacg cttccgatct ctggggccaa ggaacaacgg tcaccgtctc ctcagcctcc     360
accaagggcc catctgtctt cccactggcc ccatgctccc gcagcacctc cgagagcaca     420
gccgccctgg gctgcctggt caaggactac ttcccagaac ctgtgaccgt gtcctggaac     480
tctggcgctc tgaccagcgg cgtgcacacc ttcccagctg tcctgcagtc ctcaggtctc     540
tactccctca gcagcgtggt gaccgtgcca tccagcaact cggcaccca gacctacacc     600

```
tgcaacgtag atcacaagcc aagcaacacc aaggtagata agaccgtgga gagaaagtgt    660
tgtgtggagt gtccaccttg tccagcccct ccagtggccg gaccatccgt gttcctgttc    720
cctccaaagc caaaggacac cctgatgatc tccagaaccc cagaggtgac ctgtgtggtg    780
gtggacgtgt cccacgagga cccagaggtg cagttcaact ggtatgtgga cggagtggag    840
gtgcacaacg ccaagaccaa gccaagagag gagcagttca actccacctt cagagtggtg    900
agcgtgctga ccgtggtgca ccaggactgg ctgaacggaa aggagtataa gtgtaaggtg    960
tccaacaagg gactgccatc cagcatcgag aagaccatct ccaagaccaa gggacagcca   1020
agagagccac aggtgtatac cctgccccca tccagagagg atgaccaaga accaggtg    1080 tccctgacct gtctggtgaa gggattctat ccatccgaca tcgccgtgga gtgggagtcc   1140
aacggacagc cagagaacaa ctataagacc accctccaa tgctggactc cgacggatcc    1200
ttcttcctgt attccaagct gaccgtggac aagtccagat ggcagcaggg aaacgtgttc   1260
tcttgttccg tgatgcacga ggccctgcac aaccactata cccagaagag cctgtccctg   1320
tctccaggaa ag                                                       1332
```

<210> SEQ ID NO 27
<211> LENGTH: 11
<212> TYPE: PRT
<213> ORGANISM: Mus musculus

<400> SEQUENCE: 27

Lys Ala Ser Gln Asn Val Gly Thr Asn Val Ala
1               5                   10

<210> SEQ ID NO 28
<211> LENGTH: 7
<212> TYPE: PRT
<213> ORGANISM: Mus musculus

<400> SEQUENCE: 28

Ser Ala Ser Tyr Arg Tyr Ser
1               5

<210> SEQ ID NO 29
<211> LENGTH: 9
<212> TYPE: PRT
<213> ORGANISM: Mus musculus

<400> SEQUENCE: 29

Gln Gln Phe Tyr Ser Tyr Pro Tyr Thr
1               5

<210> SEQ ID NO 30
<211> LENGTH: 11
<212> TYPE: PRT
<213> ORGANISM: Mus musculus

<400> SEQUENCE: 30

Lys Ala Ser Gln Asp Val Ser Thr Ala Val Ala
1               5                   10

<210> SEQ ID NO 31
<211> LENGTH: 9
<212> TYPE: PRT
<213> ORGANISM: Mus musculus

<400> SEQUENCE: 31

Gln Gln Arg Tyr Ser Thr Pro Arg Thr
1               5

```
<210> SEQ ID NO 32
<211> LENGTH: 11
<212> TYPE: PRT
<213> ORGANISM: Mus musculus

<400> SEQUENCE: 32

Ser Ala Ser Gln Gly Ile Ser Asn Tyr Leu Asn
1               5                   10

<210> SEQ ID NO 33
<211> LENGTH: 7
<212> TYPE: PRT
<213> ORGANISM: Mus musculus

<400> SEQUENCE: 33

Tyr Thr Ser Ser Leu His Ser
1               5

<210> SEQ ID NO 34
<211> LENGTH: 11
<212> TYPE: PRT
<213> ORGANISM: Mus musculus

<400> SEQUENCE: 34

Lys Ala Ser Gln Asp Val Ser Asn Ala Leu Ala
1               5                   10

<210> SEQ ID NO 35
<211> LENGTH: 9
<212> TYPE: PRT
<213> ORGANISM: Mus musculus

<400> SEQUENCE: 35

Gln Gln His Tyr Ser Thr Pro Trp Thr
1               5

<210> SEQ ID NO 36
<211> LENGTH: 7
<212> TYPE: PRT
<213> ORGANISM: Mus musculus

<400> SEQUENCE: 36

Gly Tyr Thr Phe Thr Asp Tyr
1               5

<210> SEQ ID NO 37
<211> LENGTH: 5
<212> TYPE: PRT
<213> ORGANISM: Mus musculus

<400> SEQUENCE: 37

Asp Tyr Tyr Met Asn
1               5

<210> SEQ ID NO 38
<211> LENGTH: 6
<212> TYPE: PRT
<213> ORGANISM: Mus musculus

<400> SEQUENCE: 38

Asn Pro Asn Asn Gly Gly
1               5

<210> SEQ ID NO 39
```

```
<211> LENGTH: 17
<212> TYPE: PRT
<213> ORGANISM: Mus musculus

<400> SEQUENCE: 39

Asp Ile Asn Pro Asn Asn Gly Gly Thr Thr Tyr Asn Gln Lys Phe Lys
1               5                   10                  15

Gly

<210> SEQ ID NO 40
<211> LENGTH: 6
<212> TYPE: PRT
<213> ORGANISM: Mus musculus

<400> SEQUENCE: 40

Trp Leu Leu Phe Ala Tyr
1               5

<210> SEQ ID NO 41
<211> LENGTH: 7
<212> TYPE: PRT
<213> ORGANISM: Mus musculus

<400> SEQUENCE: 41

Gly Tyr Thr Phe Thr Ser Tyr
1               5

<210> SEQ ID NO 42
<211> LENGTH: 5
<212> TYPE: PRT
<213> ORGANISM: Mus musculus

<400> SEQUENCE: 42

Ser Tyr Trp Met His
1               5

<210> SEQ ID NO 43
<211> LENGTH: 6
<212> TYPE: PRT
<213> ORGANISM: Mus musculus

<400> SEQUENCE: 43

Asn Pro Ser Asn Gly Arg
1               5

<210> SEQ ID NO 44
<211> LENGTH: 17
<212> TYPE: PRT
<213> ORGANISM: Mus musculus

<400> SEQUENCE: 44

Glu Ile Asn Pro Ser Asn Gly Arg Thr Asn Tyr Asn Glu Lys Phe Lys
1               5                   10                  15

Ser

<210> SEQ ID NO 45
<211> LENGTH: 9
<212> TYPE: PRT
<213> ORGANISM: Mus musculus

<400> SEQUENCE: 45

Glu Arg Pro Leu Tyr Ala Met Asp Tyr
1               5
```

-continued

```
<210> SEQ ID NO 46
<211> LENGTH: 17
<212> TYPE: PRT
<213> ORGANISM: Mus musculus

<400> SEQUENCE: 46

Asp Ile Asn Pro Asn Asn Gly Gly Thr Ser Tyr Asn Gln Lys Phe Lys
1               5                   10                  15
Gly

<210> SEQ ID NO 47
<211> LENGTH: 14
<212> TYPE: PRT
<213> ORGANISM: Mus musculus

<400> SEQUENCE: 47

Gly Gly Ile Tyr Tyr Arg Tyr Asp Arg Asn Tyr Phe Asp Tyr
1               5                   10

<210> SEQ ID NO 48
<211> LENGTH: 7
<212> TYPE: PRT
<213> ORGANISM: Mus musculus

<400> SEQUENCE: 48

Gly Phe Thr Phe Ser Asp Tyr
1               5

<210> SEQ ID NO 49
<211> LENGTH: 5
<212> TYPE: PRT
<213> ORGANISM: Mus musculus

<400> SEQUENCE: 49

Asp Tyr Tyr Met Ala
1               5

<210> SEQ ID NO 50
<211> LENGTH: 6
<212> TYPE: PRT
<213> ORGANISM: Mus musculus

<400> SEQUENCE: 50

Asn Tyr Asp Gly Ser Asn
1               5

<210> SEQ ID NO 51
<211> LENGTH: 16
<212> TYPE: PRT
<213> ORGANISM: Mus musculus

<400> SEQUENCE: 51

Asn Ile Asn Tyr Asp Gly Ser Asn Thr Ser Tyr Leu Asp Ser Leu Lys
1               5                   10                  15

<210> SEQ ID NO 52
<211> LENGTH: 8
<212> TYPE: PRT
<213> ORGANISM: Mus musculus

<400> SEQUENCE: 52

Glu Lys Phe Ala Ala Met Asp Tyr
1               5

<210> SEQ ID NO 53
```

```
<211> LENGTH: 107
<212> TYPE: PRT
<213> ORGANISM: homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 54
<211> LENGTH: 118
<212> TYPE: PRT
<213> ORGANISM: homo sapiens

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Arg Thr Asn Tyr Asn Glu Lys Phe Lys
50                  55                  60

Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser
        115

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gln Gln Tyr Ser Lys Leu Pro Phe Thr
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 56

Gly Tyr Thr Phe Thr Asp Tyr Tyr Met Asn
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Gly Tyr Thr Phe Thr Ser Tyr Trp Met His
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Gly Phe Thr Phe Ser Asp Tyr Tyr Met Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Gly Tyr Thr Phe Thr Ser Tyr Tyr Met His
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Gly Tyr Thr Phe Thr Ser Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Ser Pro Phe Gly Gly Arg
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62
```

Gln Asp Val Ser Thr Ala Val Ala
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Gly Gly Thr Arg Val Val Ser Thr Ala Val Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Arg Gly Asp Phe Val Ser Thr Ala Val Ala
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Synthetic

<400> SEQUENCE: 65

Glu Ile Asn Pro Ser Gly Gly Arg Thr Asn Tyr Asn Glu Lys Phe Lys
1               5                   10                  15

Ser

<210> SEQ ID NO 66
<211> LENGTH: 17
<212> TYPE: PRT
<213> ORGANISM: Artificial Sequence
<220> FEATURE:
<223> OTHER INFORMATION: Synthetic

<400> SEQUENCE: 66

Glu Ile Asn Pro Ser Ser Gly Arg Thr Asn Tyr Asn Glu Lys Phe Lys
1               5                   10                  15

Ser

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Glu Ile Asn Pro Ser Thr Gly Arg Thr Asn Tyr Asn Glu Lys Phe Lys
1               5                   10                  15

Ser

<210> SEQ ID NO 68
<211> LENGTH: 17
<212> TYPE: PRT
<213> ORGANISM: Artificial Sequence
<220> FEATURE:

```
<223> OTHER INFORMATION: Synthetic

<400> SEQUENCE: 68

Glu Ile Asn Pro Ser Ile Gly Arg Thr Asn Tyr Asn Glu Lys Phe Lys
1               5                   10                  15

Ser

<210> SEQ ID NO 69
<211> LENGTH: 17
<212> TYPE: PRT
<213> ORGANISM: Artificial Sequence
<220> FEATURE:
<223> OTHER INFORMATION: Synthetic

<400> SEQUENCE: 69

Glu Ile Asn Pro Ser Asp Ser Arg Thr Asn Tyr Asn Glu Lys Phe Lys
1               5                   10                  15

Ser

<210> SEQ ID NO 70
<211> LENGTH: 17
<212> TYPE: PRT
<213> ORGANISM: Artificial Sequence
<220> FEATURE:
<223> OTHER INFORMATION: Synthetic

<400> SEQUENCE: 70

Glu Ile Asn Pro Ser Gly Asn Arg Thr Asn Tyr Asn Glu Lys Phe Lys
1               5                   10                  15

Ser

<210> SEQ ID NO 71
<211> LENGTH: 17
<212> TYPE: PRT
<213> ORGANISM: Artificial Sequence
<220> FEATURE:
<223> OTHER INFORMATION: Synthetic

<400> SEQUENCE: 71

Glu Ile Asn Pro Ser Ser Ser Arg Thr Asn Tyr Asn Glu Lys Phe Lys
1               5                   10                  15

Ser

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Glu Arg Pro Leu Tyr Ala Met Asp Tyr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Glu Arg Pro Leu Tyr Ala Ala Asp Tyr
1               5
```

```
<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Glu Arg Pro Leu Tyr Ala Ile Asp Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Glu Arg Pro Leu Tyr Ala Arg Asp Tyr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Glu Arg Pro Leu Tyr Ala Gly Asp Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic

<400> SEQUENCE: 77

Glu Arg Pro Leu Tyr Ala Lys Asp Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Glu Arg Pro Leu Tyr Ala Pro Asp Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic

<400> SEQUENCE: 79

Glu Arg Pro Leu Tyr Ala Ser Asp Tyr
1               5

<210> SEQ ID NO 80
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 80

Glu Arg Pro Leu Tyr Ala Leu Asp Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Glu Arg Pro Leu Tyr Ala Val Asp Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Glu Arg Pro Leu Tyr Ala Trp Asp Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic

<400> SEQUENCE: 83

Glu Arg Pro Leu Tyr Ala His Asp Tyr
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Glu Arg Pro Leu Tyr Ala Phe Asp Tyr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic

<400> SEQUENCE: 85

Glu Arg Pro Leu Tyr Ala Thr Asp Tyr
1               5

<210> SEQ ID NO 86
<211> LENGTH: 9
<212> TYPE: PRT
```

```
<213> ORGANISM: Artificial Sequence
<220> FEATURE:
<223> OTHER INFORMATION: Synthetic

<400> SEQUENCE: 86

Gln Gln Arg Phe Ser Thr Pro Arg Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic

<400> SEQUENCE: 87

Gln Gln Arg Tyr Ser Asp Trp Arg Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Gln Gln Arg Tyr Ser Ser Trp Arg Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic

<400> SEQUENCE: 89

Gln Gln Arg Tyr Ser Thr Ala Arg Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Gln Gln Arg Tyr Ser Leu Tyr Arg Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Gln Gln Arg Tyr Ser Phe Trp Arg Thr
1               5

<210> SEQ ID NO 92
<211> LENGTH: 9
<212> TYPE: PRT
<213> ORGANISM: Artificial Sequence
<220> FEATURE:
```

```
<223> OTHER INFORMATION: Synthetic

<400> SEQUENCE: 92

Gln Gln Arg Tyr Ser Pro Trp Arg Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gln Gln Arg Tyr Ser Gly Trp Arg Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic

<400> SEQUENCE: 94

Gln Gln Arg Tyr Ser Ile Trp Arg Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Gln Gln Arg Tyr Ser Ala Trp Arg Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Arg Tyr Ser Leu Phe Arg Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic

<400> SEQUENCE: 97

Gln Gln Arg Tyr Ser Thr Arg Arg Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 98

Gln Gln Arg Tyr Ser Thr Leu Tyr Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic

<400> SEQUENCE: 99

Gln Gln Arg Tyr Ser Thr Trp Arg Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

Gln Gln Arg Tyr Ser Leu Ala Arg Thr
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic

<400> SEQUENCE: 101

Gln Gln Arg Tyr Ser Ser Glu Arg Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic

<400> SEQUENCE: 102

Gln Gln Arg Tyr Gly Thr Ala Arg Thr
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic

<400> SEQUENCE: 103

Gln Gln Arg Tyr Ser Gln Ala Arg Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic

<400> SEQUENCE: 104
```

Gln Gln Arg Tyr Ser Leu His Arg Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic

<400> SEQUENCE: 105

Gln Gln Arg Tyr Ser Gly Val Arg Thr
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic

<400> SEQUENCE: 106

Gln Gln Arg Tyr Ser Gln Ser Arg Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Gln Gln Arg Tyr Ser Ala Glu Arg Thr
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

Gln Gln Arg Tyr Ser Gln Phe Arg Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic

<400> SEQUENCE: 109

Gln Gln Arg Tyr Ser Ser Arg Arg Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic

<400> SEQUENCE: 110

Gln Gln Arg Tyr Ser Cys Ser Arg Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic

<400> SEQUENCE: 111

Gln Gln Arg Tyr Ser Thr Asn Arg Arg
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Arg Tyr Ser Arg Trp Arg Thr
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic

<400> SEQUENCE: 113

Gln Gln Arg Tyr Ser Pro Tyr Arg Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Gln Gln Arg Tyr Ser Tyr Trp Arg Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic

<400> SEQUENCE: 115

Gln Gln Arg Tyr Ser Gly Phe Arg Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic

<400> SEQUENCE: 116

Gln Gln Arg Tyr Ser Tyr Trp Arg Thr
1               5

```
<210> SEQ ID NO 117
<211> LENGTH: 9
<212> TYPE: PRT
<213> ORGANISM: Artificial Sequence
<220> FEATURE:
<223> OTHER INFORMATION: Synthetic

<400> SEQUENCE: 117

Gln Gln Arg Tyr Ser Phe Lys Arg Thr
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic

<400> SEQUENCE: 118

Gln Gln Arg Tyr Ser Ala Arg Arg Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic

<400> SEQUENCE: 119

Gln Gln Arg Tyr Ser Arg Tyr Arg Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic

<400> SEQUENCE: 120

Gln Gln Arg Tyr Ser Leu Gln Arg Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic

<400> SEQUENCE: 121

Gln Gln Arg Tyr Ser Thr Ser Arg Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic

<400> SEQUENCE: 122

Gln Gln Arg Tyr Ser His Ala Arg Thr
1               5

<210> SEQ ID NO 123
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 123

Gln Gln Arg Tyr Ser Lys Tyr Arg Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic

<400> SEQUENCE: 124

Gln Gln Arg Tyr Ser Gln Ser Arg Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic

<400> SEQUENCE: 125

Gln Gln Arg Tyr Ser Thr Ala Phe Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic

<400> SEQUENCE: 126

Gln Gln Arg Tyr Ser Thr Cys Cys Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127

Gln Gln Arg Tyr Ser Thr Asp Arg Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Arg Tyr Ser Glu Asp Arg Thr
1               5

<210> SEQ ID NO 129
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 129

Gln Gln Arg Tyr Val Gly Arg Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic

<400> SEQUENCE: 130

Gln Gln Arg Tyr Ser Leu Ser Arg Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Gln Gln Arg Tyr Ser Leu Gly Arg Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

Gln Gln Arg Tyr Ser Arg Ala Arg Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic

<400> SEQUENCE: 133

Gln Gln Arg Tyr Ser His Ala Arg Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

Gln Gln Arg Tyr Ser Thr Pro Asp Thr
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 135

Gln Gln Arg Tyr Gln Gln Pro Arg Thr
1               5

<210> SEQ ID NO 136
<211> LENGTH: 17
<212> TYPE: PRT
<213> ORGANISM: Artificial Sequence
<220> FEATURE:
<223> OTHER INFORMATION: Synthetic

<400> SEQUENCE: 136

Glu Ile Gln Val Ser Gly Gly Arg Thr Asn Tyr Asn Glu Lys Phe Lys
1               5                   10                  15

Ser

<210> SEQ ID NO 137
<211> LENGTH: 17
<212> TYPE: PRT
<213> ORGANISM: Artificial Sequence
<220> FEATURE:
<223> OTHER INFORMATION: Synthetic

<400> SEQUENCE: 137

Glu Ile Asn Pro Trp Gln Gly Arg Thr Asn Tyr Asn Glu Lys Phe Lys
1               5                   10                  15

Ser

<210> SEQ ID NO 138
<211> LENGTH: 17
<212> TYPE: PRT
<213> ORGANISM: Artificial Sequence
<220> FEATURE:
<223> OTHER INFORMATION: Synthetic

<400> SEQUENCE: 138

Glu Ile Asn Pro Val Gln Gly Arg Thr Asn Tyr Asn Glu Lys Phe Lys
1               5                   10                  15

Ser

<210> SEQ ID NO 139
<211> LENGTH: 17
<212> TYPE: PRT
<213> ORGANISM: Artificial Sequence
<220> FEATURE:
<223> OTHER INFORMATION: Synthetic

<400> SEQUENCE: 139

Glu Ile Ser Pro Tyr Gly Gly Arg Thr Asn Tyr Asn Glu Lys Phe Lys
1               5                   10                  15

Ser

<210> SEQ ID NO 140
<211> LENGTH: 17
<212> TYPE: PRT
<213> ORGANISM: Artificial Sequence
<220> FEATURE:
<223> OTHER INFORMATION: Synthetic

<400> SEQUENCE: 140

Glu Ile Gln Glu Ser Gly Gly Arg Thr Asn Tyr Asn Glu Lys Phe Lys
1               5                   10                  15

Ser
```

<210> SEQ ID NO 141
<211> LENGTH: 17
<212> TYPE: PRT
<213> ORGANISM: Artificial Sequence
<220> FEATURE:
<223> OTHER INFORMATION: Synthetic

<400> SEQUENCE: 141

Glu Ile Ser Pro Ile Gly Gly Arg Thr Asn Tyr Asn Glu Lys Phe Lys
1               5                   10                  15

Ser

<210> SEQ ID NO 142
<211> LENGTH: 17
<212> TYPE: PRT
<213> ORGANISM: Artificial Sequence
<220> FEATURE:
<223> OTHER INFORMATION: Synthetic

<400> SEQUENCE: 142

Glu Ile Asn Pro Glu His Gly Arg Thr Asn Tyr Asn Glu Lys Phe Lys
1               5                   10                  15

Ser

<210> SEQ ID NO 143
<211> LENGTH: 17
<212> TYPE: PRT
<213> ORGANISM: Artificial Sequence
<220> FEATURE:
<223> OTHER INFORMATION: Synthetic

<400> SEQUENCE: 143

Glu Ile Asn Pro Ser Glu Gly Arg Thr Asn Tyr Asn Glu Lys Phe Lys
1               5                   10                  15

Ser

<210> SEQ ID NO 144
<211> LENGTH: 17
<212> TYPE: PRT
<213> ORGANISM: Artificial Sequence
<220> FEATURE:
<223> OTHER INFORMATION: Synthetic

<400> SEQUENCE: 144

Glu Ile Asn Pro Trp Met Gly Arg Thr Asn Tyr Asn Glu Lys Phe Lys
1               5                   10                  15

Ser

<210> SEQ ID NO 145
<211> LENGTH: 17
<212> TYPE: PRT
<213> ORGANISM: Artificial Sequence
<220> FEATURE:
<223> OTHER INFORMATION: Synthetic

<400> SEQUENCE: 145

Glu Ile Asn Pro Gln Gly Gly Arg Thr Asn Tyr Asn Glu Lys Phe Lys
1               5                   10                  15

Ser

<210> SEQ ID NO 146
<211> LENGTH: 17
<212> TYPE: PRT

```
<213> ORGANISM: Artificial Sequence
<220> FEATURE:
<223> OTHER INFORMATION: Synthetic

<400> SEQUENCE: 146

Glu Ile Asn Pro Val Lys Gly Arg Thr Asn Tyr Asn Glu Lys Phe Lys
1               5                   10                  15

Ser

<210> SEQ ID NO 147
<211> LENGTH: 17
<212> TYPE: PRT
<213> ORGANISM: Artificial Sequence
<220> FEATURE:
<223> OTHER INFORMATION: Synthetic

<400> SEQUENCE: 147

Glu Ile Gly Pro Trp Gly Gly Arg Thr Asn Tyr Asn Glu Lys Phe Lys
1               5                   10                  15

Ser

<210> SEQ ID NO 148
<211> LENGTH: 17
<212> TYPE: PRT
<213> ORGANISM: Artificial Sequence
<220> FEATURE:
<223> OTHER INFORMATION: Synthetic

<400> SEQUENCE: 148

Glu Ile Asn Pro Ile Gly Gly Arg Thr Asn Tyr Asn Glu Lys Phe Lys
1               5                   10                  15

Ser

<210> SEQ ID NO 149
<211> LENGTH: 17
<212> TYPE: PRT
<213> ORGANISM: Artificial Sequence
<220> FEATURE:
<223> OTHER INFORMATION: Synthetic

<400> SEQUENCE: 149

Glu Ile Gln Ile Ser Gly Gly Arg Thr Asn Tyr Asn Glu Lys Phe Lys
1               5                   10                  15

Ser

<210> SEQ ID NO 150
<211> LENGTH: 17
<212> TYPE: PRT
<213> ORGANISM: Artificial Sequence
<220> FEATURE:
<223> OTHER INFORMATION: Synthetic

<400> SEQUENCE: 150

Glu Ile Asn Pro Gln Gly Thr Arg Thr Asn Tyr Asn Glu Lys Phe Lys
1               5                   10                  15

Ser

<210> SEQ ID NO 151
<211> LENGTH: 9
<212> TYPE: PRT
<213> ORGANISM: Artificial Sequence
<220> FEATURE:
<223> OTHER INFORMATION: Synthetic

<400> SEQUENCE: 151
```

```
Glu Arg Pro Leu Tyr Ala Ser Asp Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Glu Arg Pro Leu Tyr Ala Ser Asp Arg
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic

<400> SEQUENCE: 153

Glu Arg Pro Leu Tyr Ala Met Asp Arg
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic

<400> SEQUENCE: 154

Glu Arg Pro Leu Tyr Ala Asn Asp Ala
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic

<400> SEQUENCE: 155

Glu Arg Pro Leu Tyr Ala Asn Asp Val
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic

<400> SEQUENCE: 156

Glu Arg Pro Leu Tyr Ala His Asp Val
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic

<400> SEQUENCE: 157

Glu Arg Pro Leu Tyr Ala Ser Asp Tyr
```

```
<210> SEQ ID NO 158
<211> LENGTH: 9
<212> TYPE: PRT
<213> ORGANISM: Artificial Sequence
<220> FEATURE:
<223> OTHER INFORMATION: Synthetic

<400> SEQUENCE: 158

Glu Arg Pro Leu Tyr Ala Ser Asp Val
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic

<400> SEQUENCE: 159

Glu Arg Pro Leu Tyr Ala Ser Asp Ala
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Glu Arg Pro Leu Tyr Ala Asn Asp Ser
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic

<400> SEQUENCE: 161

Glu Arg Pro Leu Tyr Ala Thr Asp Leu
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic

<400> SEQUENCE: 162

Glu Arg Pro Leu Tyr Ala Ser Asp Ser
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic

<400> SEQUENCE: 163

Glu Arg Pro Leu Tyr Ala Asn Asp Met
1               5
```

```
<210> SEQ ID NO 164
<211> LENGTH: 9
<212> TYPE: PRT
<213> ORGANISM: Artificial Sequence
<220> FEATURE:
<223> OTHER INFORMATION: Synthetic

<400> SEQUENCE: 164

Glu Arg Pro Leu Tyr Ala His Asp Leu
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic

<400> SEQUENCE: 165

Glu Arg Pro Leu Tyr Ala His Asp Ile
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic

<400> SEQUENCE: 166

Glu Arg Pro Leu Tyr Ala Asn Asp Val
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic

<400> SEQUENCE: 167

Glu Arg Pro Leu Tyr Ala Ser Asp Tyr
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic

<400> SEQUENCE: 168

Glu Arg Pro Leu Tyr Ala Ser Asp Arg
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic

<400> SEQUENCE: 169

Glu Arg Pro Leu Tyr Ala Ser Asp Val
1               5

<210> SEQ ID NO 170
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 170

Glu Arg Pro Leu Tyr Ala His Asp Val
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic

<400> SEQUENCE: 171

Glu Arg Pro Leu Tyr Ala Asn Asp Met
1               5

<210> SEQ ID NO 172
<211> LENGTH: 9
<212> TYPE: PRT
<213> ORGANISM: Artificial Sequence
<220> FEATURE:
<223> OTHER INFORMATION: Synthetic

<400> SEQUENCE: 172

Glu Arg Pro Leu Tyr Ala His Asp Leu
1               5

<210> SEQ ID NO 173
<211> LENGTH: 17
<212> TYPE: PRT
<213> ORGANISM: Artificial Sequence
<220> FEATURE:
<223> OTHER INFORMATION: Synthetic

<400> SEQUENCE: 173

Glu Ile Asn Pro Trp Gln Gly Arg Thr Asn Tyr Asn Glu Lys Phe Lys
1               5                   10                  15

Ser

<210> SEQ ID NO 174
<211> LENGTH: 17
<212> TYPE: PRT
<213> ORGANISM: Artificial Sequence
<220> FEATURE:
<223> OTHER INFORMATION: Synthetic

<400> SEQUENCE: 174

Glu Ile Asn Pro Val Gln Gly Arg Thr Asn Tyr Asn Glu Lys Phe Lys
1               5                   10                  15

Ser

<210> SEQ ID NO 175
<211> LENGTH: 17
<212> TYPE: PRT
<213> ORGANISM: Artificial Sequence
<220> FEATURE:
<223> OTHER INFORMATION: Synthetic

<400> SEQUENCE: 175

Glu Ile Ser Pro Tyr Gly Gly Arg Thr Asn Tyr Asn Glu Lys Phe Lys
1               5                   10                  15
```

Ser

<210> SEQ ID NO 176
<211> LENGTH: 17
<212> TYPE: PRT
<213> ORGANISM: Artificial Sequence
<220> FEATURE:
<223> OTHER INFORMATION: Synthetic

<400> SEQUENCE: 176

Glu Ile Gly Pro Trp Gly Gly Arg Thr Asn Tyr Asn Glu Lys Phe Lys
1               5                   10                  15

Ser

<210> SEQ ID NO 177
<211> LENGTH: 9
<212> TYPE: PRT
<213> ORGANISM: Artificial Sequence
<220> FEATURE:
<223> OTHER INFORMATION: Synthetic

<400> SEQUENCE: 177

Gln Gln Arg Tyr Ser Asp Trp Arg Thr
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic

<400> SEQUENCE: 178

Gln Gln Arg Tyr Ser Ser Trp Arg Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic

<400> SEQUENCE: 179

Gln Gln Arg Tyr Ser Ala Glu Arg Thr
1               5

<210> SEQ ID NO 180
<211> LENGTH: 9
<212> TYPE: PRT
<213> ORGANISM: Artificial Sequence
<220> FEATURE:
<223> OTHER INFORMATION: Synthetic

<400> SEQUENCE: 180

Gln Gln Arg Tyr Ser Leu His Arg Thr
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic

<400> SEQUENCE: 181

Gln Gln Arg Tyr Ser Ser Glu Arg Thr

```
<210> SEQ ID NO 182
<211> LENGTH: 9
<212> TYPE: PRT
<213> ORGANISM: Artificial Sequence
<220> FEATURE:
<223> OTHER INFORMATION: Synthetic

<400> SEQUENCE: 182

Gln Gln Arg Tyr Ser Leu Gln Arg Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic

<400> SEQUENCE: 183

Gln Gln Arg Tyr Ser Thr Arg Arg Thr
1               5

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Gln Gln Arg Tyr Ser Asp Trp Arg Thr
1               5

<210> SEQ ID NO 185
<211> LENGTH: 17
<212> TYPE: PRT
<213> ORGANISM: Artificial Sequence
<220> FEATURE:
<223> OTHER INFORMATION: Synthetic

<400> SEQUENCE: 185

Glu Ile Ser Pro Tyr Gly Gly Arg Thr Asn Tyr Asn Glu Lys Phe Lys
1               5                   10                  15

Ser

<210> SEQ ID NO 186
<211> LENGTH: 9
<212> TYPE: PRT
<213> ORGANISM: Artificial Sequence
<220> FEATURE:
<223> OTHER INFORMATION: Synthetic

<400> SEQUENCE: 186

Gln Gln Arg Tyr Ser Arg Ser Arg Thr
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 187

Asp Ala Ser Asn Arg Ala Thr
1               5
```

ISOLATED NUCLEIC ACID ENCODING AN ANTIBODY WHICH SPECIFICALLY BINDS TO PCSK9 AND A HOST CELL THAT PRODUCES THE ANTIBODY

This application is a divisional of U.S. application Ser. No. 12/558,312, filed Sep. 11, 2009, which claims priority, under 35 USC §119(e), to the following U.S. provisional applications, U.S. Appl. No. 61/096,716, filed Sep. 12, 2008, U.S. Appl. No. 61/232,161, filed Aug. 7, 2009, and U.S. Appl. No. 61/235,643, filed Aug. 20, 2009, each of which is herein incorporated by reference in its entirety.

REFERENCE TO SEQUENCE LISTING

This application is being filed electronically via EFS-Web and includes an electronically submitted sequence listing in .txt format. The .txt file contains a sequence listing entitled "PC33718B_SequenceListing.txt" created on Jun. 24, 2011 and having a size of 51 KB. The sequence listing contained in this .txt file is part of the specification and is herein incorporated by reference in its entirety.

FIELD OF THE INVENTION

The present invention relates to antibodies, e.g., full length antibodies or antigen-binding portions thereof, peptides, and aptamers that antagonize the activity of extracellular proprotein convertase subtilisin kexin type 9 (PCSK9), including its interaction with the low density lipoprotein (LDL) receptor (LDLR). More specifically, the invention relates to compositions comprising antagonist PCSK9 antibodies, peptides, and/or aptamers and methods of using these antibodies and/or peptides and/or aptamers as a medicament. The antagonist PCSK9 antibodies, peptides, and aptamers can be used therapeutically to lower LDL-cholesterol levels in blood, and can be used in the prevention and/or treatment of cholesterol and lipoprotein metabolism disorders, including familial hypercholesterolemia, atherogenic dyslipidemia, atherosclerosis, and, more generally, cardiovascular disease (CVD).

BACKGROUND OF THE INVENTION

Millions of people in the U.S. are at risk for heart disease and resulting cardiac events. CVD and underlying atherosclerosis is the leading cause of death among all demographic groups, despite the availability of therapies directed at its multiple risk factors. Atherosclerosis is a disease of the arteries and is responsible for coronary heart disease associated with many deaths in industrialized countries. Several risk factors for coronary heart disease have now been identified: dyslipidemias, hypertension, diabetes, smoking, poor diet, inactivity and stress. The most clinically relevant and common dyslipidemias are characterized by an increase in beta-lipoproteins (very low density lipoprotein (VLDL) and LDL) with hypercholesterolemia in the absence or presence of hypertriglyceridemia (Fredrickson et al., 1967, N Engl J. Med. 276:34-42, 94-103, 148-156, 215-225, and 273-281). There is a long-felt significant unmet need with respect to CVD with 60-70% of cardiovascular events, heart attacks and strokes occurring despite the treatment with statins (the current standard of care in atherosclerosis). Moreover, new guidelines suggest that even lower LDL levels should be achieved in order to protect high risk patients from premature CVD [National Cholesterol Education Program (NCEP), 2004].

PCSK9, also known as NARC-1, was identified as a protein with a genetic mutation in some forms of familial hypercholesterolemia. PCSK9 is synthesized as a zymogen that undergoes autocatalytic processing at the motif LVFAQ in the endoplasmic reticulum. Population studies have shown that some PCSK9 mutations are "gain-of-function" and are found in individuals with autosomal dominant hypercholesterolemia, while other "loss-of-function" (LOF) mutations are linked with reduced plasma cholesterol. Morbidity and mortality studies in this group clearly demonstrated that reducing PCSK9 function significantly diminished the risk of cardiovascular disease.

Of significant importance to the treatment of CVD, a LOF mutation may sensitize humans to statins, allowing for efficacy at a lower dose (hence, improving risks associated with safety and tolerance) and potentially achieving lower plasma cholesterol levels than with current therapies.

PCSK9 is secreted into the plasma predominantly by hepatocytes. Genetic modulation of PCSK9 in mice confirmed the ability of PCSK9 to regulate blood lipids, and suggested that it acts to down-regulate hepatic LDLR protein levels.

The mechanism by which, and the site at which, PCSK9 down-regulates LDLR protein has not been clearly established. When over-expressed, PCSK9 may act both within the hepatocyte and as a secreted ligand for LDLR. There is strong evidence that extracellular PCSK9 binds to cell surface LDLR and promotes LDLR degradation at an intracellular site. However, it is also possible that PCSK9 could interact with the LDLR when the two proteins are translated within the endoplasmic reticulum (ER) and traffic through endosomal compartments towards the cell membrane. Maxwell et al., 2005, Curr. Opin. Lipidol. 16:167-172, showed that PCSK9-mediated LDLR endocytosis and degradation was not altered by proteosome inhibitors nor was it modulated by different classes of lysosomal and nonlysosomal proteases. Two naturally occurring familial hypercholesterolemia mutations, S127R and D129G, have been reported to be defective in autoprocessing and secretion as levels of these mutant proteins were greatly reduced or undetectable in the media of transfected cells. Yet these mutants demonstrated an enhanced ability to down-regulate LDLR, consistent with their identification in individuals with high plasma LDL (Horner et al., 2008, Atherosclerosis 196:659-666; Cameron et al., 2006 Human Molecular Genetics 15:1551-1558; Lambert et al., 2006, TRENDS in Endocrinology and Metabolism 17:79-81. Since these mutants apparently do not get secreted extracellularly, and yet do downregulate LDLR, this strongly suggests that an intracellular site of action is physiologically important.

From the information available in the art, and prior to the present invention, it remained unclear whether the introduction of an antibody-, peptide-, or aptamer-based PCSK9 antagonist into the blood circulation to selectively antagonize extracellular PCSK9 would be effective to reduce hypercholesterolemia and the associated incidence of CVD and, if so, what properties of a PCSK9 antagonist are needed for such in vivo effectiveness.

SUMMARY OF THE INVENTION

This invention relates to antagonist antibodies, peptides, and aptamers that selectively interact with and inhibit PCSK9 function. It is demonstrated for the first time that certain PCSK9 antagonists are effective in vivo to lower blood cholesterol.

In one embodiment, the invention provides an isolated antagonist of PCSK9 which comprises an antibody, a peptide, or an aptamer, which interacts with PCSK9 and when administered to a subject lowers the LDL-cholesterol level in blood of said subject. The antagonist can be an antibody, for example, a monoclonal antibody or human, humanized, or chimeric antibody.

In another embodiment, the invention provides an isolated anti-PCSK9 antibody which specifically binds to PCSK9 and which is a full antagonist of the PCSK9-mediated effect on LDLR levels when measured in vitro using the LDLR down regulation assay in Huh7 cells disclosed herein.

In yet another embodiment, the invention provides an isolated antibody which antagonizes the extracellular interaction of PCSK9 with the LDLR, as measured by PCSK9 binding to the LDLR in vitro, and, when administered to a subject, lowers the LDL-cholesterol level in blood of said subject. Preferably, the antibody recognizes an epitope on human PCSK9 that overlaps with more than about 75% of the surface on PCSK9 that interacts with the EGF-like domain of the LDLR as described in Kwon et al., 2008, PNAS, 105:1820-1825.

In yet another embodiment, the invention provides an antibody that recognizes a first epitope of PCSK9 that overlaps with a second epitope that is recognized by a monoclonal antibody selected from the group consisting of 5A10, which is produced by a hybridoma cell line deposited with the American Type Culture Collection and assigned accession number PTA-8986; 4A5, which is produced by a hybridoma cell line deposited with the American Type Culture Collection and assigned accession number PTA-8985; 6F6, which is produced by a hybridoma cell line deposited with the American Type Culture Collection and assigned accession number PTA-8984, and 7D4, which is produced by a hybridoma cell line deposited with the American Type Culture Collection and assigned accession number PTA-8983.

In another embodiment, the invention provides an antibody to human PCSK9, wherein the antibody recognizes an epitope on human PCSK9 comprising amino acid residues 153-155, 194, 195, 197, 237-239, 367, 369, 374-379 and 381 of the PCSK9 amino acid sequence of SEQ ID NO: 53. Preferably, the antibody epitope on human PCSK9 does not comprise one or more of amino acid residues 71, 72, 150-152, 187-192, 198-202, 212, 214-217, 220-226, 243, 255-258, 317, 318, 347-351, 372, 373, 380, 382, and 383.

In still another embodiment, the invention provides an antibody which specifically binds PCSK9 comprising a VH complementary determining region one (CDR1) having the amino acid sequence shown in SEQ ID NO:8 (SYYMH), a VH CDR2 having the amino acid sequence shown in SEQ ID NO:9 (EISPFGGRTNYNEKFKS), and/or VH CDR3 having the amino acid sequence shown in SEQ ID NO:10 (ERPLYASDL), or a variant thereof having one or more conservative amino acid substitutions in said sequences of CDR1, CDR2, and/or CDR3, wherein the variant retains essentially the same binding specificity as the CDR defined by said sequences. Preferably, the variant comprises up to about ten amino acid substitutions and, more preferably, up to about four amino acid substitutions.

The invention is further directed to an antibody comprising a VL CDR1 having the amino acid sequence shown in SEQ ID NO:11 (RASQGISSALA), a CDR2 having the amino acid sequence shown in SEQ ID NO:12 (SASYRYT), and/or CDR3 having the amino acid sequence shown in SEQ ID NO:13 (QQRYSLWRT), or a variant thereof having one or more conservative amino acid substitutions in said sequences of CDR1, CDR2, and/or CDR3, wherein the variant retains essentially the same binding specificity as the CDR1 defined by said sequences. Preferably, the variant comprises up to about ten amino acid substitutions and, more preferably, up to about four amino acid substitutions.

In another embodiment, the invention provides an antibody comprising specific VL CDR1, CDR2, and/or CDR3 sequences, or a variant thereof having one or more conservative amino acid substitutions in CDR1, CDR2, and/or CDR3 and further comprising a VH complementary determining region CDR1 having the amino acid sequence shown in SEQ ID NO:59, 60, or 8, a VH CDR2 having the amino acid sequence shown in SEQ ID NO:61 or 9, and/or VH CDR3 having the amino acid sequence shown in SEQ ID NO:10, or a variant thereof having one or more conservative amino acid substitutions in said sequences of CDR1, CDR2, and/or CDR3, wherein the variant retains essentially the same binding specificity as the CDR1, CDR2, and/or CDR3 defined by said sequences. Preferably, the variant comprises up to about twenty amino acid substitutions and, more preferably, up to about eight amino acid substitutions. In another preferred embodiment, the antibody of the invention has a variable heavy chain sequence comprising or consisting of SEQ ID NO: 54 and a variable light chain sequence comprising or consisting of SEQ ID NO: 53.

The invention also provides a humanized antibody comprising polypeptides selected from the groups consisting of SEQ ID NO:14, SEQ ID NO:15, or both SEQ ID NO:14 and SEQ ID NO:15, or a variant thereof having one or more conservative amino acid substitutions in said sequences, wherein the variant retains essentially the same binding specificity as the antibody defined by said sequence(s). It also includes an antibody lacking a terminal lysine on the heavy chain, as this is normally lost in a proportion of antibodies during manufacture.

Preferably, the variant comprises up to about twenty amino acid substitutions and more preferably, up to about eight amino acid substitutions. Preferably, the antibody further comprises an immunologically inert constant region, and/or the antibody has an isotype that is selected from the group consisting of $IgG_2$, $IgG_4$, $IgG_{2\Delta a}$, $IgG_{4\Delta b}$, $IgG_{4\Delta c}$, $IgG_4$ S228P, $IgG_{4\Delta b}$ S228P and $IgG_{4\Delta c}$ S228P. In another preferred embodiment, the constant region is aglycosylated Fc.

In one embodiment, the invention provides a method for reducing a level of LDL, LDL-cholesterol, or total cholesterol in blood, serum, or plasma of a subject in need thereof, comprising administering to the subject a therapeutically effective amount of an antagonist of the invention.

In one embodiment, the invention provides a therapeutically effective amount of an antagonist of the invention for use in reducing a level of LDL, LDL-cholesterol, or total cholesterol in blood, serum, or plasma of a subject in need thereof. The invention further provides the use of a therapeutically effective amount of an antagonist of the invention in the manufacture of a medicament for reducing a level of LDL, LDL-cholesterol, or total cholesterol in blood, serum, or plasma of a subject in need thereof.

In yet another embodiment, the invention provides a method of preparing an antibody which specifically binds PCSK9, which comprises: a) providing a PCSK9-negative host animal; b) immunizing said PCSK9-negative host animal with PCSK9; and c) obtaining an antibody. An antibody-producing cell, or an antibody-encoding nucleic acid from said PCSK9-negative host animal, and preparing an antibody from said antibody-producing cell or said antibody-encoding nucleic acid.

The invention also comprises a method for reducing the level of LDL in blood of a subject in need thereof, comprising administering to the subject a therapeutically effective amount of the antibody prepared according to the invention.

The subject can be further treated by administering a statin. In a preferred embodiment, the subject is a human subject.

In one embodiment, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate.

In another embodiment, the invention provides a therapeutically effective amount of the antibody prepared according to the invention for use in reducing the level of LDL in blood of a subject in need thereof. The invention further provides the use of a therapeutically effective amount of the antibody prepared according to the invention in the manufacture of a medicament for reducing the level of LDL in blood of a subject in need thereof. The therapeutically effective amount can optionally be combined with a therapeutically effective amount of a statin.

In another embodiment, the invention provides a hybridoma cell line that produces a PCSK9-specific antibody or an antigen-binding portion thereof, wherein the hybridoma cell line is selected from the group consisting of:

4A5 having an ATCC Accession No. of PTA-8985;
5A10 having an ATCC Accession No. of PTA-8986;
6F6 having an ATCC Accession No. of PTA-8984; and
7D4 having an ATCC Accession No. of PTA-8983.

In another embodiment, the invention provides cell line that recombinantly produces an antibody which specifically binds to PCSK9 and comprises a heavy chain variable region (VH) complementary determining region one (CDR1) having the amino acid sequence shown in SEQ ID NO:8, 59, or 60, a VH CDR2 having the amino acid sequence shown in SEQ ID NO:9 or 61, and/or VH CDR3 having the amino acid sequence shown in SEQ ID NO:10, or a variant thereof having one or more conservative amino acid substitutions in CDR1, CDR2, and/or CDR3, and/or comprises a light chain variable region (VL) CDR1 having the amino acid sequence shown in SEQ ID NO:11, a VL CDR2 having the amino acid sequence shown in SEQ ID NO:12, and/or VL CDR3 having the amino acid sequence shown in SEQ ID NO:13, or a variant thereof having one or more conservative amino acid substitutions in CDR1, CDR2, and/or CDR3. Preferably, the cell line recombinantly produces an antibody comprising SEQ ID NO: 53 and/or 54, and, more preferably, SEQ ID NO: 14 and/or 15.

BRIEF DESCRIPTION OF THE FIGURES/DRAWINGS

Figure 1:
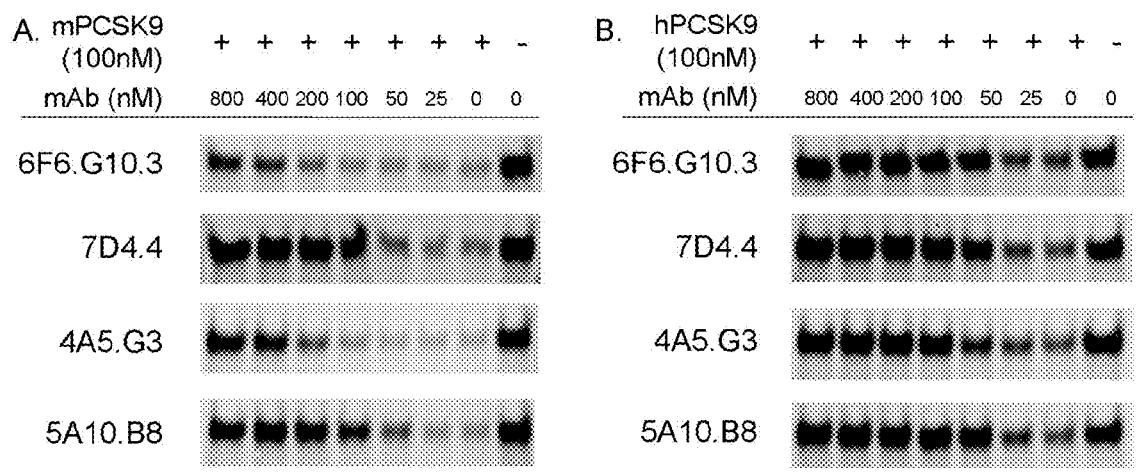
FIG. 1 illustrates the effect of anti-PCSK9 antagonistic monoclonal antibodies 7D4.4, 4A5.G3, 6F6.G10.3 and 5A10.B8 on the ability of mouse PCSK9 (A) and human PCSK9 (B) to down regulate LDLR in cultured Huh7 cells. 6F6.G10.3 is a subclone of 6F6, 7D4.4 is a subclone of 7D4, 4A5.G3 is a subclone of 4A5, and 5A10.B8 is a subclone of 5A10.

FIGS. 24 A-G depict the substitutions made in the CDRs of antibody 5A10 in the course of affinity maturation and optimization and to achieve particular properties. PCSK9 binding associated with antibodies having these CDR substitutions is also represented. The number following each sequence is the SEQ ID NO designated for each sequence.

DETAILED DESCRIPTION OF THE INVENTION

The present invention relates to antibodies, peptides, and aptamers that antagonize the function of extracellular PCSK9 including its interaction with the LDLR. More specifically, the invention relates to methods of making antagonist PCSK9 antibodies, peptides, and aptamers, compositions comprising these antibodies, peptides, and/or aptamers, and methods of using these antibodies, peptides, and/or aptamers as a medicament. The antagonist PCSK9 antibodies and peptides can be used to lower blood LDL-cholesterol levels, and can be used in the prevention and/or treatment of cholesterol and lipoprotein metabolism disorders, including familial hypercholesterolemia, atherogenic dyslipidemia, atherosclerosis, and, more generally, CVD.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv) and domain antibodies), and fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

As used herein, "humanized" antibody refers to forms of non-human (e.g., murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody.

As used herein, "human antibody" means an antibody having an amino acid sequence corresponding to that of an antibody that can be produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al. Monoclonal Antibodies and Cancer Therapy, Alan R. Liss, p. 77, 1985; Boerner et al., 1991, J. Immunol., 147 (1):86-95; and U.S. Pat. No. 5,750,373.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al, 1997, J. Molec. Biol. 273:927-948). As used herein, a CDR may refer to CDRs defined by either approach or by a combination of both approaches.

As known in the art a "constant region" of an antibody refers to the constant region of the antibody light chain or the constant region of the antibody heavy chain, either alone or in combination.

As used herein, the term "PCSK9" refers to any form of PCSK9 and variants thereof that retain at least part of the activity of PCSK9. Unless indicated differently, such as by specific reference to human PCSK9, PCSK9 includes all mammalian species of native sequence PCSK9, e.g., human, canine, feline, equine, and bovine. One exemplary human PCSK9 is found as Uniprot Accession Number Q8NBP7 (SEQ ID NO:16).

As used herein, a "PCSK9 antagonist" refers to an antibody, peptide, or aptamer that is able to inhibit PCSK9 biological activity and/or downstream pathway(s) mediated by PCSK9 signaling, including PCSK9-mediated down-regulation of the LDLR, and PCSK9-mediated decrease in LDL blood clearance. A PCSK9 antagonist antibody encompasses antibodies that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "PCSK9 antagonist antibody" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and decreased blood LDL clearance), or the consequences of the biological activity, are substantially nullified, decreased, or neutralized in any meaningful degree. In some embodiments, a PCSK9 antagonist antibody binds PCSK9 and prevents interaction with the LDLR. Examples of PCSK9 antagonist antibodies are provided herein.

As used herein a "full antagonist" is an antagonist which, at an effective concentration, essentially completely blocks a measurable effect of PCSK9. By a partial antagonist is meant an antagonist that is capable of partially blocking a measurable effect, but that, even at a highest concentration is not a full antagonist. By essentially completely is meant at least about 80%, preferably, at least about 90%, more preferably, at least about 95%, and most preferably, at least about 98% or 99% of the measurable effect is blocked. The relevant "measurable effects" are described herein and include down regulation of LDLR by a PCSK9 antagonist as assayed in Huh7 cells in vitro, in vivo decrease in blood (or plasma) levels of total cholesterol, and in vivo decrease in LDL levels in blood (or plasma).

As used herein, the term "clinically meaningful" means at least a 15% reduction in blood LDL-cholesterol levels in humans or at least a 15% reduction in total blood cholesterol in mice. It is clear that measurements in plasma or serum can serve as surrogates for measurement of levels in blood.

As used herein, the term "PCSK9 antagonist peptide" or "PCSK9 antagonist aptamer" includes any conventional peptide or polypeptide or aptamer that blocks, antagonizes, suppresses or reduces (to any degree including significantly) PCSK9 biological activity, including downstream pathways mediated by PCSK9 signaling, such as LDLR interaction and/or elicitation of a cellular response to PCSK9. PCSK9 antagonist peptides or polypeptides include Fc fusions comprising the LDLR and soluble portions of the LDLR, or mutants thereof with higher affinity to PCSK9.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O) OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "PCSK9 antagonist aptamer," which comprises a nucleic acid or protein sequence, is, for example, selected from a large pool of random sequences and specifically binds PCSK9. The nucleic acid of the aptamer is double-stranded DNA or single-strand RNA. Nucleic acid aptamers can include modified bases or functional groups, including but not limited to 2'-fluorine nucleotides and 2'-O-methyl nucleotides. Aptamers can include hydrophilic polymers, for example, polyethylene glycol. Aptamers may be made by methods known in the art and selected for PCSK9 antagonist activity by routine modification of the methods disclosed in the Examples.

As used herein, an antibody, peptide, or aptamer "interacts with" PCSK9 when the equilibrium dissociation constant is equal to or less than 20 nM, preferably less than about 6 nM, more preferably less than about 1 nM, most preferably less than about 0.2 nM, as measured by the methods disclosed herein in Example 2.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a PCSK9 epitope is an antibody that binds this epitope with greater affinity, avidity, more readily, and/or with greater duration than it binds to other PCSK9 epitopes or non-PCSK9 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976 J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

By an antibody with an epitope that "overlaps" with another (second) epitope or with a surface on PCSK9 that interacts with the EGF-like domain of the LDLR is meant the sharing of space in terms of the PCSK9 residues that are interacted with. To calculate the percent of overlap, for example, the percent overlap of the claimed antibody's PCSK9 epitope with the surface of PCSK9 which interacts with the EGF-like domain of the LDLR, the surface area of PCSK9 buried when in complex with the LDLR is calculated on a per-residue basis. The buried area is also calculated for these residues in the PCSK9:antibody complex. To prevent more than 100% possible overlap, surface area for residues that have higher buried surface area in the PCSK9:antibody complex than in LDLR:PCSK9 complex is set to values from the LDLR:PCSK9 complex (100%). Percent surface overlap is calculated by summing over all of the LDLR:PCSK9 interacting residues and is weighted by the interaction area.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g., B cell receptor), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g., from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: enhancement of LDL clearance and reducing incidence or amelioration of aberrant cholesterol and/or lipoprotein levels resulting from metabolic and/or eating disorders, or including familial hypercholesterolemia, atherogenic dyslipidemia, atherosclerosis, and, more generally, cardiovascular disease (CVD).

"Reducing incidence" means any of reducing severity (which can include reducing need for and/or amount of (e.g., exposure to) other drugs and/or therapies generally used for this condition. As is understood by those skilled in the art, individuals may vary in terms of their response to treatment, and, as such, for example, a "method of reducing incidence" reflects administering the PCSK9 antagonist antibody, peptide, or aptamer based on a reasonable expectation that such administration may likely cause such a reduction in incidence in that particular individual.

"Ameliorating" means a lessening or improvement of one or more symptoms as compared to not administering a PCSK9 antagonist antibody, peptide, or aptamer. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing hypercholesterolemia or one or more symptoms of dyslipidemia, atherosclerosis, CVD, or coronary heart disease, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using Fab antibody fragments (i.e., univalent) and PCSK9.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

A. Methods for Preventing or Treating Disorders Associated with Hypercholesterolemia In one aspect, the invention provides a method for treating or preventing hypercholesterolemia, and/or at least one symptom of dyslipidemia, atherosclerosis, CVD or coronary heart disease, in an individual comprising administering to the individual an effective amount of a PCSK9 antagonist antibody or peptide or aptamer that antagonizes circulating PCSK9.

In a further aspect, the invention provides an effective amount of a PCSK9 antagonist antibody, peptide, or aptamer that antagonizes circulating PCSK9 for use in treating or preventing hypercholesterolemia, and/or at least one symptom of dyslipidemia, atherosclerosis, CVD or coronary heart disease, in an individual. The invention further provides the use of an effective amount of a PCSK9 antagonist antibody, peptide, or aptamer that antagonizes extracellular or circulating PCSK9 in the manufacture of a medicament for treating or preventing hypercholesterolemia, and/or at least one symptom of dyslipidemia, atherosclerosis, CVD or coronary heart disease, in an individual.

Advantageously, therapeutic administration of the antibody, peptide, or aptamer results in lower blood cholesterol and/or lower blood LDL. Preferably, blood cholesterol and/or blood LDL is at least about 10% or 15% lower than before administration. More preferably, blood cholesterol and/or blood LDL is at least about 20% lower than before administration of the antibody. Yet more preferably, blood cholesterol and/or blood LDL is at least 30% lower than before administration of the antibody. Advantageously, blood cholesterol and/or blood LDL is at least 40% lower than before administration of the antibody. More advantageously, blood cholesterol and/or blood LDL is at least 50% lower than before administration of the antibody. Very preferably, blood cholesterol and/or blood LDL is at least 60% lower than before administration of the antibody. Most preferably, blood cholesterol and/or blood LDL is at least 70% lower than before administration of the antibody.

With respect to all methods described herein, reference to PCSK9 antagonist antibodies, peptides, and aptamers also include compositions comprising one or more additional agents. These compositions may further comprise suitable excipients, such as pharmaceutically acceptable excipients including buffers, which are well known in the art. The present invention can be used alone or in combination with other conventional methods of treatment.

The PCSK9 antagonist antibody, peptide, or aptamer can be administered to an individual via any suitable route. It should be apparent to a person skilled in the art that the examples described herein are not intended to be limiting but to be illustrative of the techniques available. Accordingly, in some embodiments, the PCSK9 antagonist antibody, peptide, or aptamer is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, PCSK9 antagonist antibody, peptide, or aptamer can be aerosolized using a fluorocarbon formulation and a metered dose inhaler, or inhaled as a lyophilized and milled powder.

In one embodiment, a PCSK9 antagonist antibody, peptide, or aptamer is administered via site-specific or targeted local delivery techniques. Examples of site-specific or targeted local delivery techniques include various implantable depot sources of the PCSK9 antagonist antibody, peptide, or aptamer or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publ. No. WO 00/53211 and U.S. Pat. No. 5,981,568.

Various formulations of a PCSK9 antagonist antibody, peptide, or aptamer may be used for administration. In some embodiments, the PCSK9 antagonist antibody, peptide, or aptamer may be administered neat. In some embodiments, PCSK9 antagonist antibody, peptide, or aptamer and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy, 20th Ed., Mack Publishing (2000).

These agents can be combined with pharmaceutically acceptable vehicles such as saline, Ringer's solution, dextrose solution, and the like. The particular dosage regimen, i.e., dose, timing and repetition, will depend on the particular individual and that individual's medical history.

PCSK9 antibodies can also be administered via inhalation, as described herein. Generally, for administration of PCSK9 antibodies, an initial candidate dosage can be about 2 mg/kg. For the purpose of the present invention, a typical daily dosage might range from about any of about 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce blood LDL levels. An exemplary dosing regimen comprises administering an initial dose of about 2 mg/kg, followed by a weekly maintenance dose of about 1 mg/kg of the PCSK9 antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the PCSK9 antagonist(s) used) can vary over time.

For the purpose of the present invention, the appropriate dosage of a PCSK9 antagonist antibody, peptide, or aptamer will depend on the PCSK9 antagonist antibody, peptide, or aptamer (or compositions thereof) employed, the type and severity of symptoms to be treated, whether the agent is administered for preventive or therapeutic purposes, previous therapy, the patient's clinical history and response to the agent, the patient's blood PCSK9 levels, the patient's synthesis and clearance rate for PCSK9, the patient's clearance rate for the administered agent, and the discretion of the attending physician. Typically the clinician will administer a PCSK9 antagonist antibody, peptide, or aptamer until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., hypercholesterolemia. Alternatively, sustained continuous release formulations of PCSK9 antagonist antibodies may be appropriate. Various formulations and devices for achieving sustained release are known in the art.

In one embodiment, dosages for an antagonist antibody, peptide, or aptamer may be determined empirically in individuals who have been given one or more administration(s) of an antagonist antibody, peptide, or aptamer. Individuals are given incremental dosages of a PCSK9 antagonist antibody, peptide, or aptamer. To assess efficacy, an indicator of the disease can be followed.

Administration of a PCSK9 antagonist antibody, peptide, or aptamer in accordance with the method in the present invention can be continuous or intermittent, depending, for example, upon the recipient's physiological condition, whether the purpose of the administration is therapeutic or prophylactic, and other factors known to skilled practitioners. The administration of a PCSK9 antagonist antibody, peptide, or aptamer may be essentially continuous over a preselected period of time or may be in a series of spaced doses.

In some embodiments, more than one antagonist antibody, peptide, or aptamer may be present. At least one, at least two, at least three, at least four, at least five different, or more antagonist antibodies and/or peptides can be present. Generally, those PCSK9 antagonist antibodies or peptides may have complementary activities that do not adversely affect each other. A PCSK9 antagonist antibody, peptide, or aptamer can also be used in conjunction with other PCSK9 antagonists or PCSK9 receptor antagonists. For example, one or more of the following PCSK9 antagonists may be used: an antisense molecule directed to a PCSK9 (including an anti-sense molecule directed to a nucleic acid encoding PCSK9), a PCSK9 inhibitory compound, and a PCSK9 structural analog. A PCSK9 antagonist antibody, peptide, or aptamer can also be used in conjunction with other agents that serve to enhance and/or complement the effectiveness of the agents.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing the PCSK9 antagonist antibody, peptide, or aptamer are prepared by methods known in the art, such as described in Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG- PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic PCSK9 antagonist antibody, peptide, or aptamer compositions are generally placed into a container having a sterile access port, for example, an intravenous solution bag or vial having a stopper pierceable by a hypodermic injection needle.

Suitable emulsions may be prepared using commercially available fat emulsions, such as Infralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a PCSK9 antagonist antibody, peptide, or aptamer with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

B. PCSK9 Antagonists

The methods of the invention use a PCSK9 antagonist antibody, peptide, or aptamer, which refers to any peptide or nucleic acid molecule that blocks, suppresses or reduces (including significantly reduces) PCSK9 biological activity, including downstream pathways mediated by PCSK9 signaling, such as elicitation of a cellular response to PCSK9.

A PCSK9 antagonist antibody, peptide, or aptamer should exhibit any one or more of the following characteristics: (a) bind to PCSK9; (b) block PCSK9 interaction with the LDLR; (c) block or decrease PCSK9-mediated down-regulation of the LDLR; (d) inhibit the PCSK9-mediated decrease in LDL blood clearance, (e) increase LDL clearance in media by cultured hepatocytes, (f) increase blood LDL clearance by the liver in vivo, (g) sensitize to statins, and (h) block PCSK9 interaction with other yet to be identified factors.

For purposes of this invention, the antibody, peptide, or aptamer preferably reacts with PCSK9 in a manner that inhibits PCSK9 signaling function and LDLR interaction. In some embodiments, the PCSK9 antagonist antibody specifically recognizes primate PCSK9. In some embodiments, the PCSK9 antagonist antibody binds primate and rodent PCSK9.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), human antibodies, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the PCSK9 antagonist antibody is a monoclonal antibody. The PCSK9 antagonist antibody can also be humanized. In other embodiments, the antibody is human.

In some embodiments, the antibody comprises a modified constant region, such as a constant region that is immunologically inert, that is, having a reduced potential for provoking an immune response. In some embodiments, the constant region is modified as described in Eur. J. Immunol., 1999, 29:2613-2624; PCT Publ. No. WO99/58572; and/or UK patent application No. 9809951.8. The Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type IgG2 sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19). In another embodiment, the Fc can be aglycosylated Fc.

In some embodiments, the constant region is aglycosylated by mutating the oligosaccharide attachment residue (such as Asn297) and/or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

The binding affinity ($K_D$) of a PCSK9 antagonist antibody to PCSK9 (such as human PCSK9)) can be about 0.002 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

One way of determining binding affinity of antibodies to PCSK9 is by measuring binding affinity of monofunctional Fab fragments of the antibody. To obtain monofunctional Fab fragments, an antibody (for example, IgG) can be cleaved with papain or expressed recombinantly. The affinity of a PCSK9 Fab fragment of an antibody can be determined by surface plasmon resonance (Biacore3000™ surface plasmon resonance (SPR) system, Biacore, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human PCSK9 (or any other PCSK9) can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of PCSK9 on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B., 1994. Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any PCSK9, including human PCSK9, PCSK9 of another mammalian (such as mouse PCSK9, rat PCSK9, primate PCSK9), as well as different forms of PCSK9 (such as α and β form). Binding affinity of an antibody is generally measured at 25° C., but can also be measured at 37° C.

The PCSK9 antagonist antibodies may be made by any method known in the art including the method as provided in Example 1. The route and schedule of immunization of the host animal are generally in keeping with established and conventional techniques for antibody stimulation and production, as further described herein. General techniques for production of human and mouse antibodies are known in the art and/or are described herein. A currently preferred method of making the antibodies comprises the immunization of PCSK9⁻ knockout (PCSK9 −/−) animals as disclosed herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., 1982, In Vitro, 18:377-381. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the PCSK9 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as a source of antibodies encompass all derivatives, progeny cells of the parent hybridomas that produce monoclonal antibodies specific for PCSK9, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human PCSK9, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the PCSK9 antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g., Tiller et al., 2008, J. Immunol. Methods 329, 112; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to PCSK9 and greater efficacy in inhibiting PCSK9. It will be apparent to one of skill in the art that one or more polynucleotide changes can be made to the PCSK9 antagonist antibody and still maintain its binding ability to PCSK9.

There are four general steps to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated CDRs fused to human constant domains. See, for example, Winter et al., 1991, Nature 349:293-299; Lobuglio et al., 1989, Proc. Nat. Acad. Sci. USA 86:4220-4224; Shaw et al., 1987, J. Immunol. 138:4534-4538; and Brown et al., 1987, Cancer Res. 47:3577-3583. Other references describe rodent CDRs grafted into a human supporting framework region (FR) prior to fusion with an appropriate human antibody constant domain. See, for example, Riechmann et al., 1988, Nature 332:323-327; Verhoeyen et al., 1988, Science 239:1534-1536; and Jones et al., 1986, Nature 321:522-525. Another reference describes rodent CDRs supported by recombinantly engineered rodent framework regions. See, for example, European patent Publ. No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g., PCT Publ. No. WO99/58572; UK patent application No. 9809951.8. Other methods of humanizing antibodies that may also be utilized are disclosed by Daugherty et al., 1991, Nucl. Acids Res. 19:2471-2476 and in U.S. Pat. Nos. 6,180,377; 6,054,297; 5,997,867; 5,866,692; 6,210,671; and 6,350,861; and in PCT Publ. No. WO 01/27160.

In yet another alternative, fully human antibodies may be obtained by using commercially available mice that have been engineered to express specific human immunoglobulin proteins. Transgenic animals that are designed to produce a more desirable or more robust immune response may also be used for generation of humanized or human antibodies. Examples of such technology are Xenomouse™ from Abgenix, Inc. (Fremont, Calif.), HuMAb-Mouse® and TC Mouse™ from Medarex, Inc. (Princeton, N.J.), and the VelocImmune® mouse from Regeneron Pharmaceuticals, Inc. (Tarrytown, N.Y.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., 1994, Annu. Rev. Immunol. 12:433-455. Alternatively, the phage display technology (McCafferty et al., 1990, Nature 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; see, e.g., Johnson, Kevin S, and Chiswell, David J., 1993, Current Opinion in Structural Biology 3:564-571. Several sources of V-gene segments can be used for phage display. Clackson et al., 1991, Nature 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., 1991, J. Mol. Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., 1992, Bio/Technol. 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., 1993, Nucl. Acids Res. 21:2265-2266. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publ. No. WO 93/06213). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, 2001, et al. Vaccine 19:2756; Lonberg, N. and D. Huszar, 1995, Int. Rev. Immunol 13:65; and Pollock, et al., 1999, J Immunol Methods 231:147. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for PCSK9.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publ. No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publ. No. WO 87/04462. The DNA also may be modified, for example, by substituting the coding sequence for human heavy and light chain constant domains in place of the homologous murine sequences, Morrison et al., 1984, Proc. Nat. Acad. Sci. 81:6851, or by covalently joining to the immunoglobulin coding sequence all or part of the coding sequence for a non-immunoglobulin polypeptide. In that manner, "chimeric" or "hybrid" antibodies are prepared that have the binding specificity of a PCSK9 monoclonal antibody herein.

PCSK9 antagonist antibodies and polypeptides derived from antibodies can be identified or characterized using methods known in the art, whereby reduction, amelioration, or neutralization of PCSK9 biological activity is detected and/or measured. In some embodiments, a PCSK9 antagonist antibody or polypeptide is identified by incubating a candidate agent with PCSK9 and monitoring binding and/or attendant reduction or neutralization of a biological activity of PCSK9. The binding assay may be performed with purified PCSK9 polypeptide(s), or with cells naturally expressing, or transfected to express, PCSK9 polypeptide(s). In one embodiment, the binding assay is a competitive binding assay, where the ability of a candidate antibody to compete with a known PCSK9 antagonist for PCSK9 binding is evaluated. The assay may be performed in various formats, including the ELISA format. In other embodiments, a PCSK9 antagonist antibody is identified by incubating a candidate agent with PCSK9 and monitoring binding and attendant inhibition of LDLR expression and/or blood cholesterol clearance.

Following initial identification, the activity of a candidate PCSK9 antagonist antibody can be further confirmed and refined by bioassays that are known to test the targeted biological activities. Alternatively, bioassays can be used to screen candidates directly. Some of the methods for identifying and characterizing PCSK9 antagonist antibodies, peptides, or aptamers are described in detail in the Examples. PCSK9 antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, (Cold Spring Harbor Laboratory Press, Cold Spring Harbor, N.Y., 1999). In an additional example, epitope mapping can be used to determine the sequence to which a PCSK9 antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a PCSK9 antagonist antibody. In another example, the epitope to which the PCSK9 antagonist antibody binds can be determined in a systematic screening by using overlapping peptides derived from the PCSK9 sequence and determining binding by the PCSK9 antagonist antibody. According to the gene fragment expression assays, the open reading frame encoding PCSK9 is fragmented either randomly or by specific genetic constructions and the reactivity of the expressed fragments of PCSK9 with the antibody to be tested is determined. The gene fragments may, for example, be produced by PCR and then transcribed and translated into protein in vitro, in the presence of radioactive amino acids. The binding of the antibody to the radioactively labeled PCSK9 fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant PCSK9 in which various fragments of the PCSK9 polypeptide have been replaced (swapped) with sequences from PCSK9 from another species, or a closely related, but antigenically distinct protein (such as another member of the proprotein convertase family). By assessing binding of the antibody to the mutant PCSK9, the importance of the particular PCSK9 fragment to antibody binding can be assessed.

Yet another method which can be used to characterize a PCSK9 antagonist antibody is to use competition assays with other antibodies known to bind to the same antigen, i.e., various fragments on PCSK9, to determine if the PCSK9 antagonist antibody binds to the same epitope as other antibodies. Competition assays are well known to those of skill in the art.

The crystal structure of the antibody and antibody:antigen complex can also be used to characterize the antibody. The residues are identified by calculating the difference in accessible surface area between the L1L3:PCSK9 crystal structure and PCSK9 structure alone. PCSK9 residues that show buried surface area upon complex formation with L1L3 antibody are included as a part of the epitope. The solvent accessible surface of a protein is defined as the locus of the centre of a probe sphere (representing a solvent molecule of 1.4 Å radius) as it rolls over the Van der Waals surface of the protein. The solvent accessible surface area is calculated by generating surface points on an extended sphere about each atom (at a distance from the atom centre equal to the sum of the atom and probe radii), and eliminating those that lie within equivalent spheres associated with neighboring atoms as implemented in program AREAIMOL (Briggs, P. J., 2000, CCP4 Newsletter No. 38, CCLRC, Daresbury).

An expression vector can be used to direct expression of a PCSK9 antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., 1993, Trends Biotechnol. 11:202; Chiou et al., 1994, Gene Therapeutics: Methods And Applications Of Direct Gene Transfer (J. A. Wolff, ed.); Wu et al., 1988, J. Biol. Chem. 263:621; Wu et al., 1994, J. Biol. Chem. 269:542; Zenke et al., 1990, Proc. Natl. Acad. Sci. USA 87:3655; Wu et al., 1991, J. Biol. Chem. 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, 1994, Cancer Gene Therapy 1:51; Kimura, 1994, Human Gene Therapy 5:845; Connelly, 1995, Human Gene Therapy 1:185; and Kaplitt, 1994, Nature Genetics 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publ. Nos. WO 90/07936; WO 94/03622; WO 93/25698; WO 93/25234; WO 93/11230; WO 93/10218; WO 91/02805; U.S. Pat. Nos. 5,219,740 and 4,777,127; GB patent No. 2,200,651; and EP patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publ. Nos. WO 94/12649, WO 93/03769; WO 93/19191; WO 94/28938; WO 95/11984 and WO 95/00655). Administration of DNA linked to killed adenovirus as described in Curiel, 1992, Hum. Gene Ther. 3:147, can also be employed.

Non-viral delivery vehicles and methods can also be employed, including, but not limited to, polycationic condensed DNA linked or unlinked to killed adenovirus alone (see, e.g., Curiel, 1992, Hum. Gene Ther. 3:147); ligand-linked DNA (see, e.g., Wu, J., 1989, Biol. Chem. 264:16985); eukaryotic cell delivery vehicles cells (see, e.g., U.S. Pat. No. 5,814,482; PCT Publ. Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publ. No. WO 90/11092 and U.S. Pat. No. 5,580,859. Liposomes that can act as gene delivery vehicles are described in U.S. Pat. No. 5,422,120; PCT Publ. Nos. WO 95/13796; WO 94/23697; WO 91/14445; and EP 0524968. Additional approaches are described in Philip, 1994, Mol. Cell. Biol., 14:2411, and in Woffendin, 1994 Proc. Natl. Acad. Sci. 91:1581.

This invention encompasses compositions, including pharmaceutical compositions, comprising antibodies described herein or made by the methods and having the characteristics described herein. As used herein, compositions comprise one or more antibodies, peptides, or aptamers that antagonize the interaction of PCSK9 with the LDLR, and/or one or more polynucleotides comprising sequences encoding one or more these antibodies or peptides. These compositions may further comprise suitable excipients, such as pharmaceutically acceptable excipients including buffers, which are well known in the art.

The PCSK9 antagonist antibodies and peptides of the invention are characterized by any (one or more) of the following characteristics: (a) bind to PCSK9; (b) block PCSK9 interaction with the LDLR; (c) decrease PCSK9-mediated down-regulation of the LDLR; and (d) inhibit PCSK9-mediated inhibition of LDL blood clearance. Preferably, PCSK9 antibodies have two or more of these features. More preferably, the antibodies have three or more of the features. Most preferably, the antibodies have all four characteristics.

Accordingly, the invention provides any of the following, or compositions (including pharmaceutical compositions) comprising any antibody having a partial light chain sequence and a partial heavy chain sequence as found in Table 1. The underlined sequences are CDR sequences according to Kabat and in bold according to Chothia.

TABLE 1

| mAb | Light Chain Variable Region | Heavy Chain Variable Region |
|---|---|---|
| 4A5 | DIVMTQSQKFMSTSVGDRV | EVQLQQSGPELVKPGASVKISCKAS |
|  | SVTC<u>KASQNVGTNVA</u>WYQ | GYTFTD<u>YYMN</u>WVKQSHGKSLEWIG |
|  | QKPGQSPKALIY<u>SASYRYSG</u> | DI<u>NPNNGGTTYNQKFKG</u>KATLTVDKS |
|  | VPDRFTGSGSGTDFTLTISN | YSTAYMELRSLTSEDSAVYYCAR<u>WL</u> |
|  | VLSEDLAEYFC<u>QQFYSYPYT</u> | <u>LFAY</u>WGQGTLVTVSA |
|  | FGGGTKLEIK (SEQ ID NO: 16) | (SEQ ID NO: 20) |

TABLE 1-continued

| mAb | Light Chain Variable Region | Heavy Chain Variable Region |
|---|---|---|
| 5A10 | DIVMTQSHKFMSTSVGDRVS ITCKASQDVSTAVAWYQQK PGQSPKLLIYSASYRYTGVP DRFTGSGSGTDFTFTISSVQ AEDLAVYYCQQRYSTPRTF GGGTKLEIK (SEQ ID NO: 17) | QVQLQQPGAELVKPGASVKLSCKAS GYTFTSY<u>WMH</u>WVKQRPGQGLEWIG EINPSNGRTNYNEKFKSKATLTVDKS SSTAYMQLSSLTSEDSAVYYCAR<u>ER</u> PLYAMDYWGQGTSVTVSS (SEQ ID NO: 21) |
| 6F6 | DIQMTQTTSSLSASLGDRVTI SCSASQGISNYLNWYQQKP DGTVKLLIYYTSSLHSGVPS RFSGSGSGTDYSLTISNLEP EDIATYYCQQYSKLPFTFGS GTKLEIK (SEQ ID NO: 18) | EVQLQQSGPELVKPGASVKISCKAS GYTFTD<u>YYMN</u>WVKQSHGKSLEWIG DINPNNGGTSYNQKFKGKATLTVDK SSSTAYMELRSLTSEDSAVYYCAG<u>G</u> GIYYRYDRNYFDYWGQGTTLTVSS (SEQ ID NO: 22) |
| 7D4 | DIVMTQSHKFMSTSFGDRVS ITCKASQDVSNALAWYQQK PGHSPKLLIFSASYRYTGVP DRFTGSGSGTDFTFTISSVQ AEDLAVYYCQQHYSTPWTF GGGTKLEIK (SEQ ID NO: 19) | EVKLVESEGGLVQPGSSMKLSCTAS GFTFSD<u>YYMA</u>WVRQVPEKGLEWVA NINYDGSNTSYLDSLKSRFIISRDNAK NILYLQMSSLKSEDTATYYCAR<u>EKFA</u> AMDYWGQGTSVTVSS (SEQ ID NO: 23) |
| L1L3 | DIQMTQSPSSLSASVGDRVT ITCRASQGISSALAWYQQKP GKAPKLLIYSASYRYTGVPS RFSGSGSGTDFTFTISSLQP EDIATYYCQQRYSLWRTFG QGTKLEIK (SEQ ID NO: 53) | QVQLVQSGAEVKKPGASVKVSCKAS GYTFTSY<u>YMH</u>WVRQAPGQGLEWM GEISPFGGRTNYNEKFKSRVTMTRD TSTSTVYMELSSLRSEDTAVYYCAR<u>E</u> RPLYASDLWGQGTTVTVSS (SEQ ID NO: 54) |

The invention also provides CDR portions of antibodies to PCSK9 (including Chothia and Kabat CDRs). Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies and peptides can be made recombinantly using procedures that are well known in the art. In one embodiment, a polynucleotide comprises a sequence encoding the heavy chain and/or the light chain variable regions of antibody 4A5, 5A10, 6F6, 7D4 or L1L3. The sequence encoding the antibody of interest may be maintained in a vector in a host cell and the host cell can then be expanded and frozen for future use. Vectors (including expression vectors) and host cells are further described herein.

The invention also encompasses scFv of antibodies of this invention. Single chain variable region fragments are made by linking light and/or heavy chain variable regions by using a short linking peptide. Bird et al., 1988, Science 242:423-426. An example of a linking peptide is (GGGGS)$_3$ (SEQ ID NO:24), which bridges approximately 3.5 nm between the carboxy terminus of one variable region and the amino terminus of the other variable region. Linkers of other sequences have been designed and used. Bird et al., 1988, supra. Linkers should be short, flexible polypeptides and preferably comprised of less than about 20 amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publ. No. WO 94/04690.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publ. Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibodies 5A10 or 7D4 or one or more CDRs derived from antibodies 5A10 or 7D4 can be made, for example, using any methods know in the art. For example, four general steps may be used to humanize a monoclonal antibody. These are: (1) determining the nucleotide and predicted amino acid sequence of the starting antibody light and heavy variable domains; (2) designing the humanized antibody, i.e., deciding which antibody framework region to use during the humanizing process; (3) using the actual humanizing methodologies/techniques; and (4) transfecting and expressing the humanized antibody. See, for example, U.S. Pat. Nos. 4,816, 567; 5,807,715; 5,866,692; 6,331,415; 5,530,101; 5,693,761; 5,693,762; 5,585,089; and 6,180,370.

In the recombinant humanized antibodies, the Fc portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

Humanized antibody comprising the light or heavy chain variable regions or one or more CDRs of an antibody or its variants shown in Table 1, or one or more CDRs derived from the antibody or its variants shown in Table 2 can be made using any methods known in the art.

Humanized antibodies may be made by any method known in the art.

The invention encompasses modifications to the antibodies and polypeptides of the invention variants shown in Table 1, including functionally equivalent antibodies which do not significantly affect their properties and variants which have enhanced or decreased activity and/or affinity. For example, the amino acid sequence may be mutated to obtain an antibody with the desired binding affinity to PCSK9. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 2 under the heading of "conservative substitutions." If such substitutions result in a change in biological activity, then more substantial changes, denominated "exemplary substitutions" in Table 2, or as further described below in reference to amino acid classes, may be introduced and the products screened.

TABLE 2

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of $\beta(1,4)$-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g., antibodies, as potential therapeutics is rarely the native cell, variations in the glycosylation pattern of the antibodies can be expected (see, e.g., Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate ADCC, or does not activate microglia; or have reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., 1995, Immunology 86:319-324; Lund et al., 1996, J. Immunology 157:4963-9 157:4963-4969; Idusogie et al., 2000, J. Immunology 164:4178-4184; Tao et al., 1989, J. Immunology 143: 2595-2601; and Jefferis et al., 1998, Immunological Reviews 163:59-76. In some embodiments, the constant region is modified as described in Eur. J. Immunol., 1999, 29:2613-2624; PCT Publ. No. WO99/58572; and/or UK patent application No. 9809951.8. In other embodiments, the antibody comprises a human heavy chain IgG2 constant region comprising the following mutations: A330P331 to S330S331 (amino acid numbering with reference to the wild type IgG2 sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., 1989, J. Immunology 143: 2595-2601; and Jefferis et al., 1998, Immunological Reviews 163: 59-76. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publ. No. WO 99/58572. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publ. No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore surface plasmon resonance analysis, which detects differences in binding affinity of about 2-fold or greater. Biacore is particularly useful when the starting antibody already binds with a relatively high affinity, for example a $K_D$ of about 10 nM or lower. Screening using Biacore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, screening, and selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid, and may further include additional substitutions at that position, depending on the complexity of the library that is desired, or permitted using the desired screening or selection method. In addition, if desired, and adjacent amino acid position can be randomized to at least two or more amino acids. Randomization of adjacent amino acids may permit additional conformational flexibility in the mutant CDR, which may, in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

The invention also encompasses fusion proteins comprising one or more fragments or regions from the antibodies or polypeptides of this invention. In one embodiment, a fusion polypeptide is provided that comprises at least 10 contiguous amino acids of a variable light chain region shown in SEQ ID NOs: 53, 16, 17, 18, or 19 and/or at least 10 amino acids of a variable heavy chain region shown in SEQ ID NOs: 54, 20, 21, 22, or 23. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 53 and 54, 16 and 20, 17 and 21, 18 and 22, and 19 and 23. In another embodiment, the fusion polypeptide comprises one or more CDR(s). In still other embodiments, the fusion polypeptide comprises CDR H3 (VH CDR3) and/or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies or polypeptides conjugated (for example, linked) to an agent that facilitate coupling to a solid support (such as biotin or avidin). For simplicity, reference will be made generally to antibodies with the understanding that these methods apply to any of the PCSK9 binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent such as a fluorescent molecule, a radioactive molecule or any others labels known in the art. Labels are known in the art which generally provide (either directly or indirectly) a signal.

The invention also provides compositions (including pharmaceutical compositions) and kits comprising, as this disclosure makes clear, any or all of the antibodies and/or polypeptides described herein.

The invention also provides isolated polynucleotides encoding the antibodies and peptides of the invention, and vectors and host cells comprising the polynucleotide.

Accordingly, the invention provides polynucleotides (or compositions, including pharmaceutical compositions), comprising polynucleotides encoding any of the following: the antibodies 4A5, 5A10, 6F6, 7D4, L1L3, or any fragment or part thereof having the ability to antagonize PCSK9.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as pharmaceutical compositions) comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies or polypeptides described herein. In still other embodiments, the composition comprises either or both of the polynucleotides shown in SEQ ID NO:25 and SEQ ID NO:26. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure (National Biomedical Research Foundation, Washington D.C.), Vol. 5, Suppl. 3, pp. 345-358; Hein J., 1990, Unified Approach to Alignment and Phylogenes pp. 626-645 Methods in Enzymology vol. 183, (Academic Press, Inc., San Diego, Calif.); Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy (Freeman Press, San Francisco, Calif.); Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989, supra.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al., 1994, eds. (Birkauswer Press, Boston, Mass.).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp 18, mp 19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publ. No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but are not limited to COS, HeLa, NS0, and CHO cells. See also PCT Publ. No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to PCSK9 or a PCSK9 domain is effected by an immunoassay or FACS. A cell overexpressing the antibody or protein of interest can be identified.

C. Compositions

The compositions used in the methods of the invention comprise an effective amount of a PCSK9 antagonist antibody, a PCSK9 antagonist antibody derived polypeptide, or other PCSK9 antagonists described herein. Examples of such compositions, as well as how to formulate them, are also described in an earlier section and below. In one embodiment, the composition further comprises a PCSK9 antagonist. In another embodiment, the composition comprises one or more PCSK9 antagonist antibodies. In other embodiments, the PCSK9 antagonist antibody recognizes human PCSK9. In still other embodiments, the PCSK9 antagonist antibody is humanized. In yet other embodiments, the PCSK9 antagonist antibody comprises a constant region that does not trigger an unwanted or undesirable immune response, such as antibody-mediated lysis or ADCC. In other embodiments, the PCSK9 antagonist antibody comprises one or more CDR(s) of the antibody (such as one, two, three, four, five, or, in some embodiments, all six CDRs). In some embodiments, the PCSK9 antagonist antibody is human.

It is understood that the compositions can comprise more than one PCSK9 antagonist antibody (e.g., a mixture of PCSK9 antagonist antibodies that recognize different epitopes of PCSK9). Other exemplary compositions comprise more than one PCSK9 antagonist antibodies that recognize the same epitope(s), or different species of PCSK9 antagonist antibodies that bind to different epitopes of PCSK9.

The composition used in the present invention can further comprise pharmaceutically acceptable carriers, excipients, or stabilizers (Remington: The Science and Practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Pharmaceutically acceptable excipients are further described herein.

In one embodiment, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate.

The PCSK9 antagonist antibody and compositions thereof can also be used in conjunction with other agents that serve to enhance and/or complement the effectiveness of the agents.

D. Kits

The invention also provides kits for use in the instant methods. Kits of the invention include one or more containers comprising a PCSK9 antagonist antibody (such as a humanized antibody) or peptide described herein and instructions for use in accordance with any of the methods of the invention described herein. Generally, these instructions comprise a description of administration of the PCSK9 antagonist antibody, peptide, or aptamer for the above described therapeutic treatments.

In some embodiments, the antibody is a humanized antibody. In some embodiments, the antibody is human. In other embodiments, the antibody is a monoclonal antibody. The instructions relating to the use of a PCSK9 antagonist antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PCSK9 antagonist antibody. The container (e.g., pre-filled syringe or autoinjector) may further comprise a second pharmaceutically active agent.

Kits may optionally provide additional components such as buffers and interpretive information. Normally, the kit comprises a container and a label or package insert(s) on or associated with the container.

Mutations and Modifications

To express the PCSK9 antibodies of the present invention, DNA fragments encoding $V_H$ and $V_L$ regions can first be obtained using any of the methods described above. Various modifications, e.g., mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant domain of an antibody. In some embodiments, the cysteine is canonical.

The antibodies may also be modified, e.g., in the variable domains of the heavy and/or light chains, e.g., to alter a binding property of the antibody. For example, a mutation may be made in one or more of the CDR regions to increase or decrease the $K_D$ of the antibody for PCSK9, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant domain to increase the half-life of a PCSK9 antibody. See, e.g., PCT Publ. No. WO 00/09560. A mutation in a framework region or constant domain can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant domain.

In a process known as "germlining", certain amino acids in the $V_H$ and $V_L$ sequences can be mutated to match those found naturally in germline $V_H$ and $V_L$ sequences. In particular, the amino acid sequences of the framework regions in the $V_H$ and $V_L$ sequences can be mutated to match the germline sequences to reduce the risk of immunogenicity when the antibody is administered. Germline DNA sequences for human $V_H$ and $V_L$ genes are known in the art (see e.g., the "Vbase" human germline sequence database; see also Kabat, E. A., et al. (1991) Sequences of Proteins of Immunological Interest, Fifth Edition, U.S. Department of Health and Human Services, NIH Publ. No. 91-3242; Tomlinson et al., 1992, J. Mol. Biol. 227:776-798; and Cox et al., 1994, Eur. J. Immunol. 24:827-836.

Another type of amino acid substitution that may be made is to remove potential proteolytic sites in the antibody. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. Another type of amino acid substitution eliminates asparagine-glycine pairs, which form potential deamidation sites, by altering one or both of the residues. In another example, the C-terminal lysine of the heavy chain of a PCSK9 antibody of the invention can be cleaved. In various embodiments of the invention, the heavy and light chains of the PCSK9 antibodies may optionally include a signal sequence.

Once DNA fragments encoding the $V_H$ and $V_L$ segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publ. No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the $V_H$-encoding DNA can be operatively linked to another DNA molecule encoding only the heavy chain CH1 constant region. The CH1 heavy chain constant region may be derived from any of the heavy chain genes.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al., 1991, Sequences of Proteins of Immunological Interest, Fifth Edition, U.S. Department of Health and Human Services, NIH Publ. No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to PCSK9 and to another molecule.

In another embodiment, a fusion antibody or immunoadhesin may be made that comprises all or a portion of a PCSK9 antibody of the invention linked to another polypeptide. In another embodiment, only the variable domains of the PCSK9 antibody are linked to the polypeptide. In another embodiment, the $V_H$ domain of a PCSK9 antibody is linked to a first polypeptide, while the $V_L$ domain of a PCSK9 antibody is linked to a second polypeptide that associates with the first polypeptide in a manner such that the $V_H$ and $V_L$ domains can interact with one another to form an antigen binding site. In another preferred embodiment, the $V_H$ domain is separated from the $V_L$ domain by a linker such that the $V_H$ and $V_L$ domains can interact with one another. The $V_H$-linker-$V_L$ antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In other embodiments, other modified antibodies may be prepared using PCSK9 antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., 1993, Proc. Natl. Acad. Sci. USA 90:6444-6448), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

Bispecific antibodies or antigen-binding fragments can be produced by a variety of methods including fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. In addition, bispecific antibodies may be formed as "diabodies" or "Janusins." In some embodiments, the bispecific antibody binds to two different epitopes of PCSK9. In some embodiments, the modified antibodies described above are prepared using one or more of the variable domains or CDR regions from a human PCSK9 antibody provided herein.

Generation of Antigen-specific Antibodies

More than 500 polyclonal and monoclonal antibodies raised against recombinant full-length human PCSK9, recombinant full length mouse PCSK9, and various synthetic peptides were evaluated for their ability to down regulate total LDLR protein in cultured Huh7 human liver cells. Among these antibodies were a set of antibodies raised to and reactive with a set of 12-20 amino acid residue polypeptides that, based on the structure of PCSK9, were predicted to cover majority of the protein surface. At the highest concentration, the best antibodies exhibited only about 60% blocking activity.

Thus, an alternative and heretofore unexplored approach was employed, namely, the generation of monoclonal antibodies by immunizing PCSK9 null mice with recombinant full-length PCSK9 protein. This manner of antibody preparation yielded antagonist antibodies that show complete blocking of PCSK9 binding to LDLR, complete blocking of PCSK9-mediated lowering of LDLR levels in Huh7 cells, and lowering of uLDLc in vivo including in mice to levels comparable to that seen in PCSK9 −/− mice, as shown in Example 7.

Representative antibodies (hybridomas) of the present invention were deposited in the American Type Culture Collection (ATCC) on Feb. 28, 2008, and were assigned the accession numbers in Table 3. Hybridomas were deposited for antibodies 4A5, 5A10, 6F6 and 7D4.

TABLE 3

| Antibody Reference | ATCC Accession No. |
| --- | --- |
| 4A5 | PTA-8985 |
| 5A10 | PTA-8986 |
| 6F6 | PTA-8984 |
| 7D4 | PTA-8983 |

EXAMPLES

Example 1

Generating and Screening PCSK9 Antagonist Antibodies

General Procedures for Immunization of Animals for Generating Monoclonal Antibodies:

Balb/c or 129/bl6 pcsk9 −/− mice were injected 5 times on a 13 day schedule with 100 µg antigen. PCSK9−/− (that is, null or knock-out mice) can be obtained from, or as described by, Rashid et al., 2005, Proc Natl Acad Sci USA 102: 5374. See also U.S. Pat. No. 7,300,754. For the first 4 injections, antigen was prepared by mixing the recombinant proteins with adjuvant. Immunogen was given via injection to the scruff of the neck, the foot pads and intraperitoneally, approximately every 3 days over the course of 11 days, with the last boost administered i.v., without adjuvant. On Day 13, the mice were euthanized and their spleens were removed. Lymphocytes were immortalized by fusion with an established cell line to make hybridoma clones using standard hybridoma technology, distributed into 96 well plates. Clones were allowed to grow, then selected by ELISA screening using the immunizing antigen, as below.

ELISA Screening of Antibodies:

Supernatant media from growing hybridoma clones were screened separately for their ability to bind the recombinant human PCSK9 or recombinant mouse PCSK9. The assays were performed with 96-well plates coated overnight with 100 µl of a 1 µg/ml solution of one of the antigens. Excess reagents were washed from the wells between each step with PBS containing 0.05% Tween-20. Plates were then blocked with PBS containing 0.5% BSA. Supernatant was added to the plates and incubated at room temperature for 2 hours. Horse radish peroxidase (HRP) conjugated goat-anti mouse Fc was added to bind to the mouse antibodies bound to the antigen. Tetramethyl benzidine was then added as substrate for HRP to detect the amount of mouse antibody present in the supernatant. The reaction was stopped and the relative amount of antibody was quantified by reading the absorbance at 450 nm. Hybridoma clones that secreted antibodies that are capable of binding to either mouse or human PCSK9 were selected for further analysis.

PCSK9-Mediated LDLR Down-regulation in Huh7 Cells:

Hybridoma clones secreting human or mouse PCSK9 binding antibodies were expanded and supernatants were harvested. Total IgGs were purified from approximately 10 ml of the supernatant using protein A beads, dialyzed into PBS buffer, and the final volume reduced to yield solutions with 0.7-1 mg/ml of antibodies. Purified antibodies were then used to test their ability to inhibit the ability of PCSK9 to mediate LDLR down-regulation in Huh7 cells. Huh7 cells were plated and allowed to grow to 80% confluency in RPMI media containing 10% FBS, 4 mM glutamine, and penicillin and streptavidin in 96 well plates. The medium was changed to one containing 10% de-lipidated FBS for 8-16 hrs to induce LDLR expression. Cells were then incubated for 8-16 hours with 40 µl/well of 293 expression media supplemented with 6 µg/ml of human (preferably) or mouse PCSK9, with or without 70-100 µg/ml of test antibodies. The PCSK9 and antibody containing media were removed at the end of incubation, and cells were lysed with 17 µl lysis buffer by shaking at 4 C for an hour. The lysis buffer consisted of 50 mM glycerol phosphate, 10 mM HEPES pH 7.4, 1% Triton X-100, 20 mM NaCl, and a cocktail of protease inhibitors (Roche). Cell lysates were collected and analyzed for LDLR protein levels via staining of Western blots following SDS polyacrylamide gel electrophoresis. Hybridoma clones producing antibodies that can partially or fully rescue LDLR level were selected for further analysis. By "LDLR down regulation assay" is meant the above assay using Huh7 cells.

FIG. 1 illustrates the effect of anti-PCSK9 antagonistic monoclonal antibodies 7D4.4, 4A5.G3, 6F6.G10.3 and 5A10.B8 on the ability of human and mouse PCSK9 to down regulate LDLR in cultured Huh7 cells. 100 nM of mouse or human recombinant PCSK9, and a serial dilution of 25-800 nM of antibodies were used. A) mouse PCSK9. B) human PCSK9. The figures are Western blots showing that the antibodies are in general more effective in blocking the function of human PCSk9 than mouse PCSK9. The several antibodies have generally similar affinities for human PCSK9 but vary in their affinity for murine PCSK9.

Example 2

Determining Antibody Binding Affinity

The affinities of PCSK9 antibodies to PCSK9 were measured on a surface plasmon resonance Biacore 3000 biosensor equipped with a research-grade sensor chip using HBS-EP running buffer (Biacore AB, Uppsala, Sweden—now GE Healthcare). Rabbit polyclonal anti-Ms IgGs were amine-coupled at saturating levels onto the chip using a standard N-hydroxysuccinimide/ethyldimethylaminopropyl carbodiimide (NHS/EDC) chemistry. The buffer was switched to HBS-EP+1 mg/mL BSA+1 mg/mL CM-dextran. Full-length PCSK9 IgGs were diluted to about 15 µg/mL and captured for 1 min at 5 µL/min to give levels of about 500 RU per flow cell, leaving one blank to serve as a reference channel. 3.73-302 nM hPCSK9 or 2.54-206 nM mPCSK9 were injected as a 5-membered 3-fold series for 1 min at 100 µL/min. Dissociation was monitored for 5 min. The chip was regenerated after the last injection of each titration with two 30 sec pulses of 100 mM phosphoric acid. Buffer cycles provided blanks for double-referencing the data, which were then fit globally to a simple binding model using Biaevaluation software v.4.1. Affinities were deduced from the quotient of the kinetic rate constants ($K_D = k_{off}/k_{on}$). The results of Example 2 are shown in Table 4. These data show that the antibodies have excellent affinity for murine PCSK9 or human PCSK9, as indicated.

TABLE 4

| mAb | ligand | Inhibition of LDLR-PCSK9 binding ($IC_{50}$) | $K_{on}$ for PCSK9 (1/Ms) | $K_{off}$ for PCSK9 (1/S) | $K_D$ for PCSK9 (nM) |
|---|---|---|---|---|---|
| 4A5 | human | 0.4 nM | $6.66 \times 10^4$ | $1.89 \times 10^{-4}$ | 2.8 |
| 5A10 | human | 0.4 nM | $8.47 \times 10^4$ | $8.55 \times 10^{-5}$ | 1 |
| 6F6 | human | 1.5 nM | $9.15 \times 10^4$ | $5.84 \times 10^{-4}$ | 6.4 |
| 7D4 | human | 1.5 nM | $1.25 \times 10^5$ | $7.94 \times 10^{-4}$ | 6.4 |
| 4A5 | mouse | 3 nM | $1.41 \times 10^5$ | $7.2 \times 10^{-4}$ | 5.1 |
| 5A10 | mouse | 3 nM | $1.27 \times 10^5$ | $4.89 \times 10^{-4}$ | 3.9 |
| 6F6 | mouse | 10 nM | $1.11 \times 10^5$ | $1.97 \times 10^{-3}$ | 17.7 |
| 7D4 | mouse | 1 nM | $3.92 \times 10^4$ | $5.23 \times 10^{-4}$ | 1.3 |

Example 3

Analysis of the Effect of PCSK9 Antibodies on PCSK9-LDLR Interaction

PCSK9 has been shown to bind LDLR with an affinity of 180 nM under neutral pH (Cunningham et al., 2007, Nat Struct Mol Biol, 14(5):413-9). Recombinant mouse or human PCSK9 protein was biotinylated using the Pierce reagents following the manufacture's instructions. ELISA plates (Corning Mixisorb) were coated with a solution of 1 µg/ml recombinant LDLR extracellular domain (R&D Systems) in each well at 4 C overnight, blocked with 2% BSA+PBS for 2 hrs at room temperature, and then washed 5 times with washing buffer (1×PBS+0.05% Tween-20). Wells were incubated with 50 µl of indicated concentrations of biotinylated PCSK9 protein for 1 hr RT. LDLR-PCSK9 binding can be stabilized by adding 50 µl of 4% FDH+4% sucrose+PBS solution and incubate for 5 min. Wells were washed 5 times with washing buffer, incubated with 1:2000 dilution of HRP conjugated Strepavidin (Invitrogen) for 1 hr at RT, washed 5 times with washing buffer. TMB substrate was added to the wells, the solution was incubated 20 to 30 min at RT, and the reaction was terminated using 1 M phosphoric acid. Signals were read at 450 nm.

Figure 2:
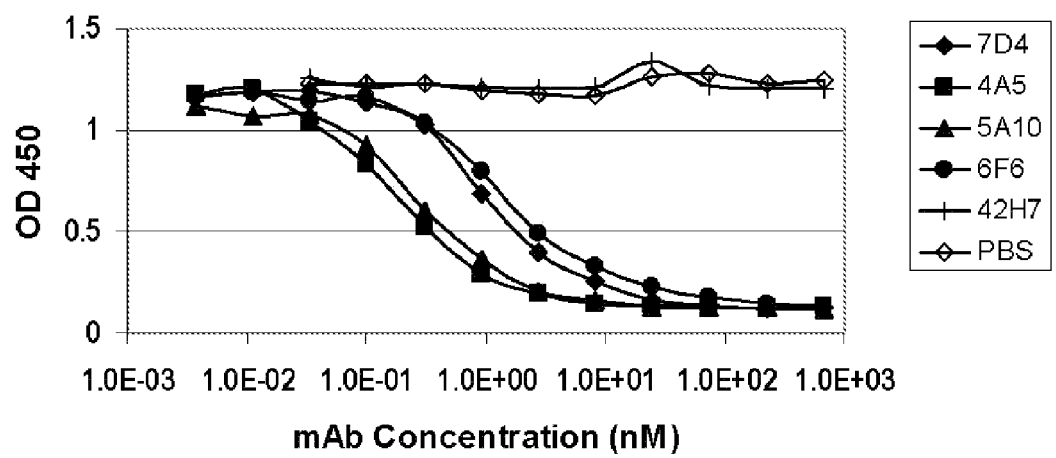
FIG. 2 illustrates the dose-response of anti-PCSK9 antagonist monoclonal antibodies 6F6.G10.3, 7D4.4, 4A5.G3, 5A10.B8, negative control antibody 42H7, and PBS to block the binding of recombinant biotinylated human PCSK9 (A) and mouse PCSK9 (B) to immobilized recombinant LDLR extracellular domain in vitro.
Figure 2:
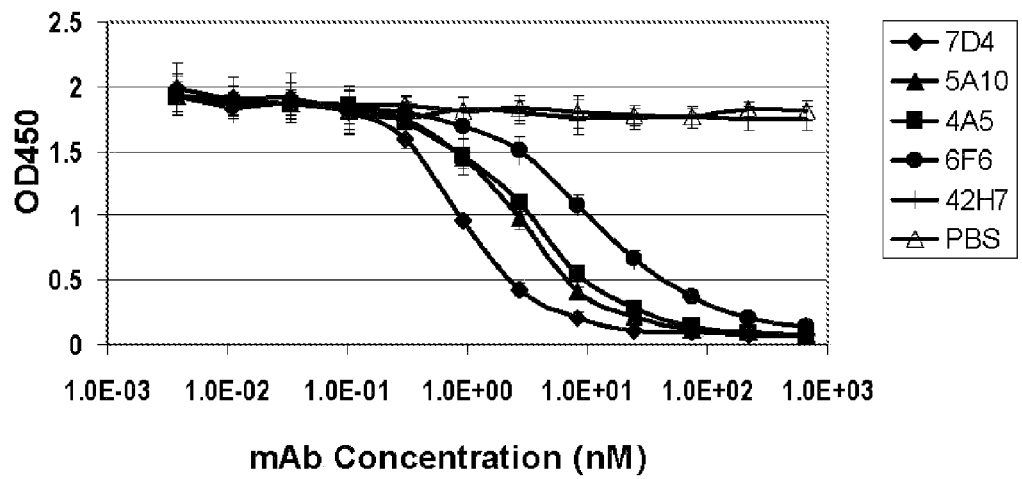

FIG. 2 illustrates the dose-response of anti-PCSK9 antagonist monoclonal antibodies 6F6.G10.3, 7D4.4, 4A5.G3, 5A10.B8, negative control antibody 42H7, and PBS on blocking the binding of recombinant biotinylated human PCSK9 and mouse PCSK9 to immobilized recombinant LDLR extracellular domain in vitro. Part A) shows human PCSK9 binding to human LDLR extracellular domain and that 7D4, 4A5, 5A10, and 6F6 are effective in blocking binding, whereas 42H7 and PBS are not. Part B) shows mouse PCSK9 binding to human LDLR extracellular domain.

Figure 3:
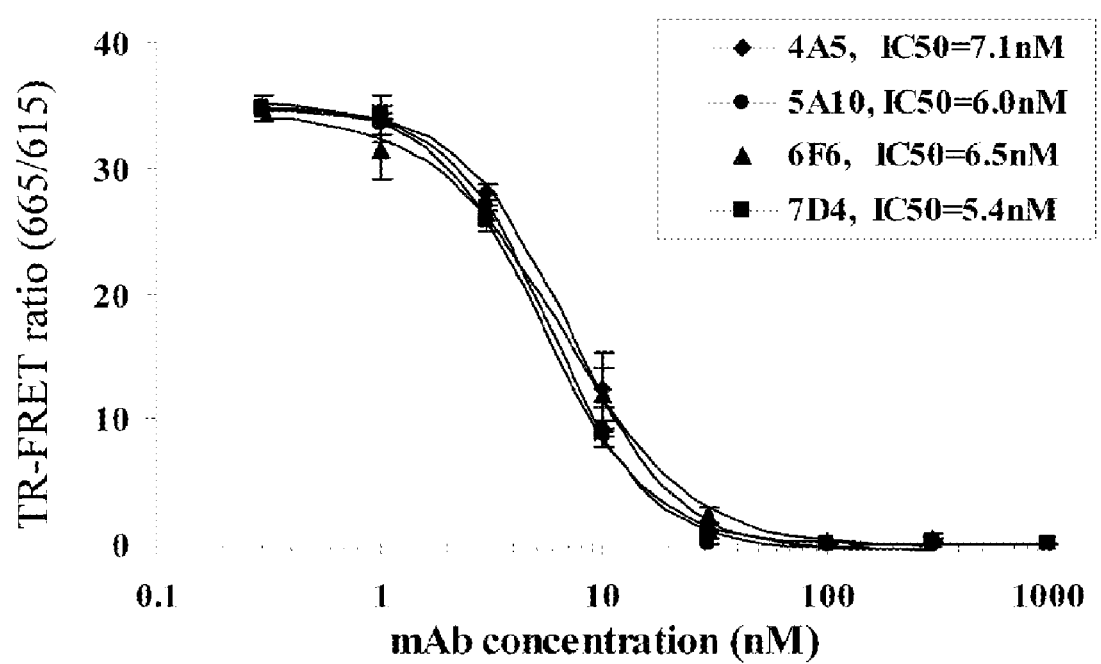
FIG. 3 illustrates the dose-response of anti-PCSK9 monoclonal antagonist antibodies 6F6.G10.3, 7D4.4, 4A5.G3 and 5A10.B8 to block binding of recombinant biotinylated human PCSK9 (30 nM) to Europium labeled recombinant LDLR extracellular domain (10 nM) in solution at neutral pH in vitro.

The interaction can also be evaluated in free solution at neutral pH. FIG. 3 illustrates the dose-response of anti-PCSK9 monoclonal antagonist antibodies 6F6.G10.3, 7D4.4, 4A5.G3 and 5A10.B8 on blocking binding of recombinant biotinylated human PCSK9 (30 nM) to Europium labeled recombinant LDLR extracellular domain (10 nM) in solution at neutral pH in vitro. This assay measures binding in free solution at neutral pH.

Example 4

Epitope Mapping/Binding of Antibodies using the Crystal Structure of the L1L3:PCSK9 Complex, Biacore, and Mutagenesis a. Crystal structure of the L1L3:PCSK9 complex. The residues were identified by calculating the difference in accessible surface area between the L1L3:PCSK9 crystal structure and PCSK9 structure alone. PCSK9 residues that show buried surface area upon complex formation with L1L3 antibody were included as a part of the epitope. The solvent accessible surface of a protein was defined as the locus of the centre of a probe sphere (representing a solvent molecule of 1.4 Å radius) as it rolls over the Van der Waals surface of the protein. The solvent accessible surface area was calculated by generating surface points on an extended sphere about each atom (at a distance from the atom centre equal to the sum of the atom and probe radii), and eliminating those that lie within equivalent spheres associated with neighboring atoms as implemented in program AREAIMOL (Briggs, P. J., 2000, CCP4 Newsletter No. 38, CCLRC, Daresbury).

Figure 23:
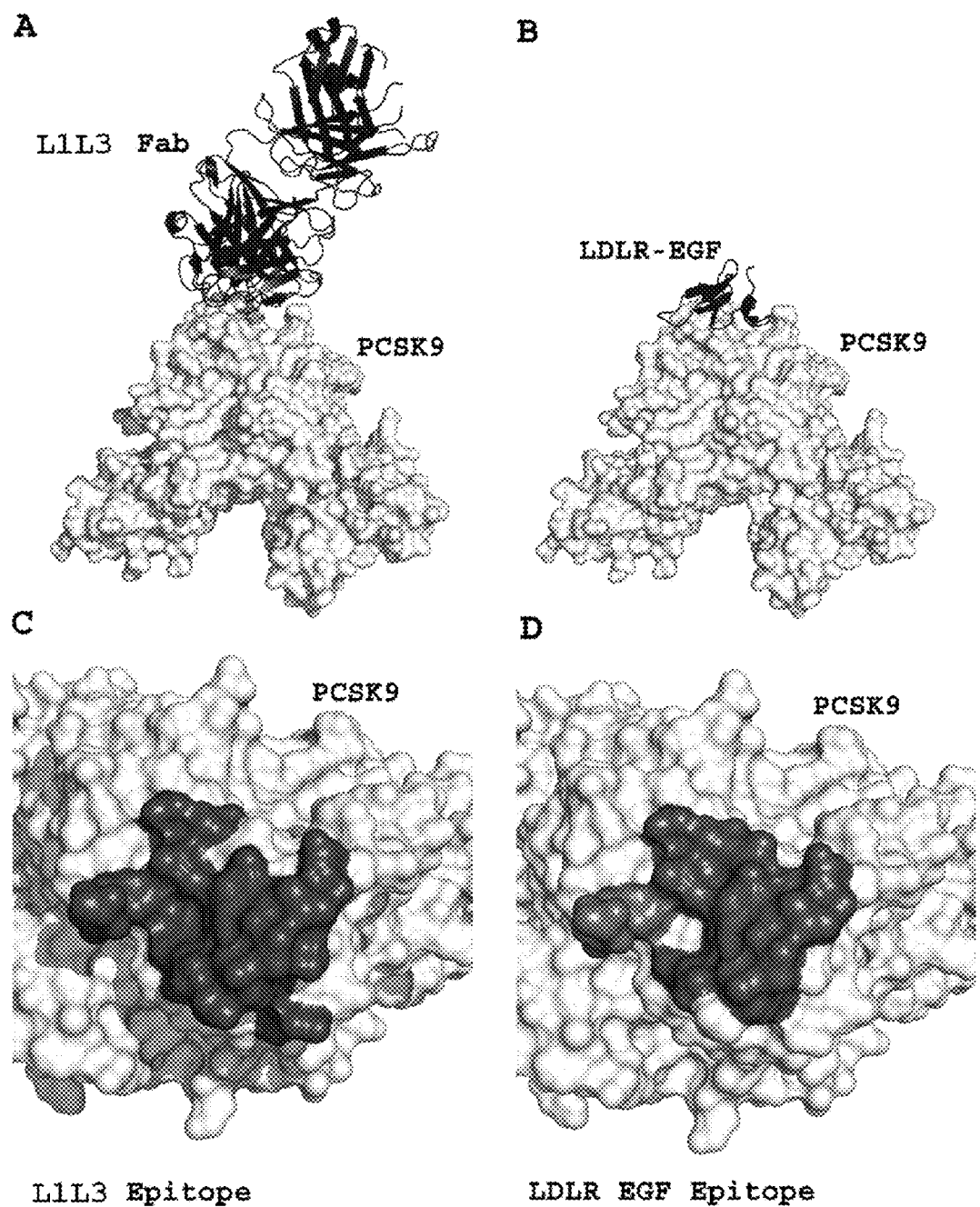
FIG. 23A depicts the crystal structure of the PCSK9 (light gray surface representation) bound to the L1L3 antibody (black cartoon representation).
FIG. 23B depicts the crystal structure of the PCSK9 (light gray surface representation) bound to the EGF-like domain of the LDLR (black cartoon representation) (Kwon et al., PNAS, 105, 1820-1825, 2008).
FIG. 23C shows the surface area representation of PCSK9 with the L1L3 epitope shown in dark gray.
FIG. 23D shows the surface area representation of PCSK9 with the LDLR EGF-like domain epitope shown in dark gray.

The result of the crystal structure analysis are shown in FIG. 23. FIG. 23A shows the crystal structure of the PCSK9 (light gray surface representation) bound to the L1L3 antibody (black cartoon representation). The epitope for L1L3 binding to PCSK9 involves residues 153-155, 194, 197, 237-239, 367, 369, 374-379 and 381 of the PCSK9 amino acid sequence (SEQ ID NO:53). By comparison, the epitope for the LDLR EGF domain binding to PCSK9 involves residues 153-155, 194, 238, 367, 369, 372, 374-375, and 377-381 (Kwon et al., 2008, PNAS 105: 1820-1825).

b. Group antibodies and epitopes based on competition in PCSK9 binding. Full-length IgGs were amine-coupled to a CM5 sensor chip (three per chip at about 7000 RU final), using a standard EDC/NHS-mediated amine-coupling chemistry. One flow cell was left unmodified to provide a reference channel. Human-PCSK9 (100 nM) was premixed with an array of IgGs (final 500 nM) and these complexes were injected over the chip using 1 min injections at 10 μL/min. Antibodies that bind to competing epitopes will block the binding of PCSK9 to the antibody immobilized on the chip. Alternatively, a classical sandwich approach was used by first injecting human-PCSK9 at 50 nM for 1 min at 10 μL/min (to tether it via the IgG on the chip) and then binding an array of IgGs (final 500 nM each) for 2 mins each. The immobilized IgGs were regenerated with a mild acid (Pierce gentle elution buffer+1 M NaCl). Antibodies directed to known different epitopes were used as controls for positive sandwich formation in this assay.

c. Structure-guided mutagenesis to map antibody binding epitopes. Based on the crystal structure of PCSK9 and the likely involvement of D374 in LDLR binding (Cunningham et al., 2007, Nat Struct Mol Biol, 14(5): 413-419), nineteen PCSK9 surface-residue mutants (F379A, I369A, R194A, D374Y, D238R, T377R, K222A, R199A, F216A, R218A, R237A, D192R, D367R, R165A, R167A, A443T, A53V, I474V, H449A) near or far from the position of D374 were chosen for mutation to map the antibody binding epitopes.

d. Mutant and antibody production. The 19 single point mutants were generated from the previously described wild-type DNA construct (Cunningham et al., 2007, supra) using standard DNA techniques. The mutant proteins were expressed using transient transfection in HEK293T cells and secreted into the cell media. The mutant proteins were purified with the high-throughput AKTA Xpress system (GE Healthcare) by $Ni^{2+}$ and size-exclusion chromatography steps, using conditions similar to those described earlier. Protein concentrations were determined using the LabChip instrument (Bio-Rad). The PCSK9-blocking murine antibodies 4A5, 7D4, 5A10 and 6F6 were expressed with transient transfection in HEK293F cells and purified with a protein G column eluted with 0.1 M Glycine buffer at pH 2.8 and neutralized into 1.0 M Tris at pH 9.0.

e. The regions of PCSK9 that are contacted by monoclonal antibodies 5A10 and 7D4 (preparation described later herein) were determined by protein tomography (Sidec AB, Stockholm, Sweden). The loops at positions 186-200, 371-379, 176-181, 278-283, 449-453, 402-406, and 236-245 of PCSK9 were proximal to amino acid residues of the antibody. The sequences corresponding to the loops are shown in Table 5, and in a preferred embodiment, the antagonists of the invention bind to one or more of these sequences in PSCK9.

TABLE 5

| PCSK9 Loops | Sequence | SEQ ID NO. |
|---|---|---|
| 186-200 | DTSIQSDHREIEGRV | 1 |
| 236-245 | GRDAGVAKGA | 2 |
| 371-379 | ASSDCSTCF | 3 |
| 176-181 | GGSLVE | 4 |
| 278-283 | QPVGPL | 5 |
| 449-453 | HGAGW | 6 |
| 402-406 | AEPEL | 7 | f. Biacore binding of the mutants to immobilized LDLR. Recombinant LDLR extracellular domain protein was immobilized onto a Biacore SA chip. Each mutant protein was injected to the Biacore-3000 M) in duplicates at 25 mM to 0.012 mM at five concentrations (from 1° C., with a running buffer of 50 mM Tris pH 7.5, 2 mM $CaCl_2$, 200 mM NaCl, 0.02% P20 and 1 mg/ml BSA. All the results fit nicely to a 1:1 binding kinetics model. As expected, mutation at residues in direct contact with the EGF-A domain (F379A, R194A, I369A, T377R, D238R) significantly weakens (by 10-100 fold) LDLR binding. Moreover, three mutants not in contact with EGF-A (R199A, R218A, K222A) showed weaker binding (5-15 fold). This new finding suggests that they are involved in binding other domains of LDLR. Overall, these experiments validate the integrity and activity of the mutants for subsequent epitope mapping experiments.

g. Binding of the mutants to immobilized 4A5, 7D4, 5A10 and 6F6 antibodies. Biotinylated anti-PCSK9 antibodies were immobilized on SA chips using standard methods. Mutant binding experiments were performed using Biacore 3000 at 25° C. with a running buffer of 50 mM Tris-HCl pH 7.5, 150 mM NaCl and 0.02% P20. Mutants were tested at 333 nM or 111 nM concentrations in duplicates, with the ones giving weakened binding compared to the wild-type as the residues involved in mAb binding (listed below).

| mAb | Binding Residues in Descending Order of Mutant Effects |
|---|---|
| 4A5 | R237, F379, 369, R194, R199 & D238 |
| 5A10 | R194, R237, I369, D238, R199 |
| 6F6 | R237, R194, F379, D238, I369, T377, R199 |
| 7D4 | R237, R194, F379, I369, R199 |

Example 5

Cloning and Sequencing of Antibodies

One million hybridoma cells were homogenized using the QIAshredder spin columns and total RNA was extracted according to RNAeasy Micro kit from QIAGEN. cDNA was synthesized using SuperScript III RT kit from Invitrogen. Variable regions from the PCSK9 antibodies were cloned using the mouse IgG-Primer Sets from Novagen, which consist of degenerate primers for cloning mouse IgG heavy chain genes and the mouse kappa or lambda light chains. PCR cycling conditions were the followings: 1 cycle at 92 C for 2 min; two cycles at 94 C for 30 sec, 44 C for 30 sec and 72 C for 2 min; two cycles at 94 C for 30 sec, 46 C for 30 sec and 72 C for 2 min; two cycles at 94 C for 30 sec, 48 C for 30 sec and 72 C for 2 min; two cycles at 94 C for 30 sec, 50 C for 30 sec and 72 C for 2 min; two cycles at 94 C for 30 sec, 52 C for 30 sec and 72 C for 2 min; followed by 35 cycles at 94 C for 30 sec, 54 C for 30 sec and 72 C for 45 sec. The resulting PCR products were cloned into Topo-TA cloning vector from Invitrogen and sequenced. The cloned antibody sequences were confirmed by N-terminal sequencing of the first 10 amino acids of the original antibodies produced from ascites.

Example 6

Generation of Antigens for Immunization

Recombinant human PCSK9 protein was produced as reported Cunningham et al., 2007, Nat Struct Mol Biol, 14(5): 413-9. To produce recombinant mouse PCSK9 protein, the cDNA of mouse PCSK9 was cloned into mammalian expression vector PRK5 with the addition of a 6-His tag at the C-terminus by methods known in the art, transiently transfected and expressed in HEK293 cells. Recombinant protein was purified from conditioned media using a Ni column.

Surface peptides of human and mouse PCSK9 were selected based on PCSK9 protein structure, and synthesized by Elim Biopharmaceuticals.

Example 7

PCSK9-Specific Antibodies as PCSK9 Antagonists

1. Identification of PCSK9-Specific Antagonist Antibodies
a. Identification of PCSK9-Blocking Antibodies Murine antibodies to human and/or mouse PCSK9 were generated by immunizing mice with human-PCSK9 and mouse-PCSK9 synthetic peptides as prepared in Example 6 or recombinant proteins, and screening antibodies by ELISA assay using human and/or mouse PCSK9 recombinant protein as the antigens as described in Example 1 and other standard hybridoma procedures. Over 500 positive clones were obtained and allowed to grow to confluency in 6 well plates with 10 ml media. Media supernatant were collected and total IgGs in the conditioned media were purified using mAb Select (Pierce). The ability of purified and concentrated mouse IgGs to inhibit mouse and human PCSK9 function was tested in Huh7 cells using the methods described in Example 1. Hybridoma clones expressing IgGs that showed some degrees of blocking were expanded and retested. 60 promising clones were subcloned, expanded, and injected into either Balb/c or nude mice to produce ascites. Antibodies purified from ascites fluid were retested for their ability to inhibit the down regulation of LDLR by human or mouse PCSK9 in Huh7 cells. Four hybridoma clones, 4A5, 5A10, 6F6, and 7D4, were identified as being able to completely inhibit human PCSK9 function, and at least partially inhibit mouse PCSK9 function. To determine $IC_{50}$ of each of these blocking antibodies, a serial dilution of IgGs were used in the assay, starting from 100 μg/ml to 3.125 μg/ml, with human and mouse PCSK9 concentration being constant at 6 μg/ml.

b. Effect of PCSK9 Antagonists on PCSK9-LDLR Binding

PCSK9 has been shown to be co-localized with LDLR in cellular compartments (Lagace et al., 2006, J Clin Inv, 116 (11):2995-3005. Recombinant PCSK9 protein also binds to LDLR extracellular domain in vitro (Fisher et al., 2007, JBC, 282(28):20502-12. To determine the relationship between inhibition of PCSK9 mediated down-regulation of LDLR and inhibition of PCSK9-LDLR binding by antibodies, we tested the PCSK9 antibodies that partially or completely blocked PCSK9 function on LDLR and representatives of antibodies that do not block. All partial antagonistic antibodies also partially inhibited LDLR extracellular domain binding to PCSK9, except one. Antagonistic antibodies that can completely block PCSK9 function, namely 4A5, 5A10, 6F6 and 7D4 also completely inhibited LDLR extracellular domain binding to PCSK9 (Table 5). $IC_{50}$ values of these four antibodies correlates with their binding affinity to PCSK9.

c. Epitope Determination of the Blocking Antibodies

Figure 4:
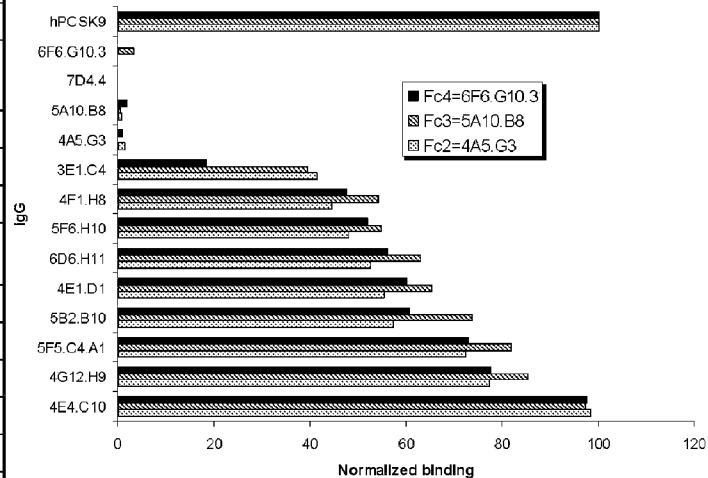
FIG. 4 illustrates comparative epitope binding of anti-PCSK9 antibodies.

FIG. 4 illustrates the epitope binding of anti-PCSK9 antibodies. Part A) shows epitope information of anti-PCSK9 mAbs, determined by binding to synthetic 13-18-mer peptides or epitope binding via Biacore. Part B) shows the ability of immobilized antibodies 6F6, 5A10 and 4A5 to bind to human PCSK9 μremixed with the mAbs indicated on the y axis by Biacore assay.

Another monoclonal anti-PCSK9 antibody, termed 6G7, binds to recombinant mouse PCSK9 but not human PCSK9. See Table 6. 6G7, 4A5, 5A10, 6F6, and 7D4 mutually exclude each other's binding to mouse PCSK9. Chimera analysis between mouse and human PCSK9 reveals that 6G7 binding to PCSK9 requires the catalytic domain. See Table 6. Thus the binding sites of 4A5, 5A10, 6F6, and 7D4 overlap the catalytic site and/or the epitope bound by 6G7.

TABLE 6

| Recombinant protein | 6G7 binding |
|---|---|
| Human PCSK9 | No |
| Human pro + human catalytic + mouse C-term | No |
| Human pro + mouse catalytic + mouse C-term | Yes |
| Mouse pro + human catalytic + human C-term | No |
| Mouse Pro + mouse catalytic + human C-term | Yes |
| Mouse PCSK9 | yes | d. Determining Sequences Species Specificity of Anti-PCSK9 Antibodies

Figure 5:
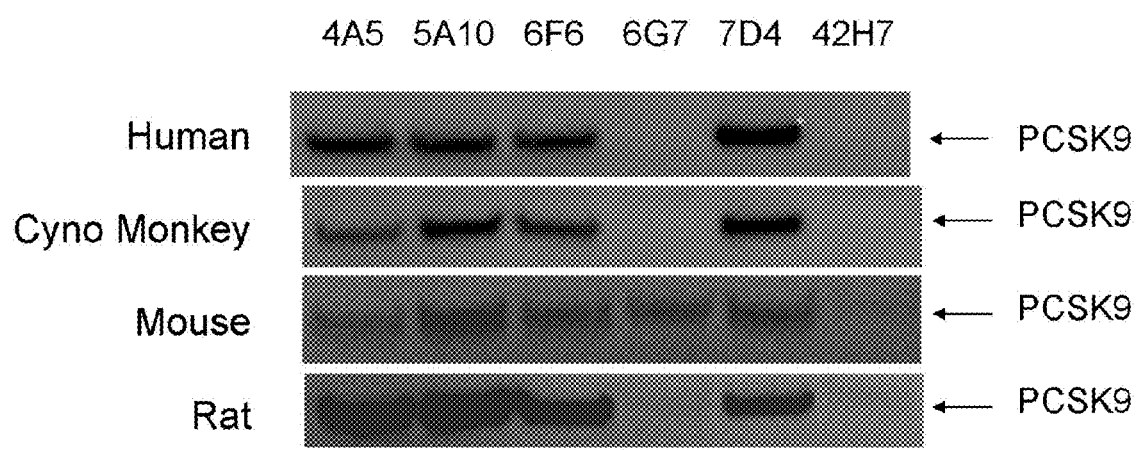
FIG. 5 illustrates Western blots of binding of anti-PCSK9 antibodies to serum PCSK9 from different species.

To determine the species specificity of the anti-PCSK9 antibodies, antibodies were incubated with plasma from different species and the resultant complexes were purified and probed by an independent anti PCSK9 antibody on Western blots. The antibodies 4A5, 5A10, 6F6, and 7D4 recognized human, cynomolgus monkey, mouse, and rat PCSK9. See FIG. 5. Antibody 6G7 recognized only murine PCSK9 and an unrelated control antibody 42H7 did not recognize any tested PCSK9. Id.

e. Determining Sequences of Antagonist PCSK9 Antibodies

The amino acid sequences of the variable domains of PCSK9 antibodies 4A5, 5A10, 6F6, and 7D4 were determined using the method described in Example 5. The sequences indicate that the antibodies are related but different from each other. Table 1 shows the amino acid sequences of the variable regions of each antibody. Table 7 shows the CDR sequences of the light chains and heavy chains of Table 1 as identified by the Kabat and Chotia methods.

Figure 6:
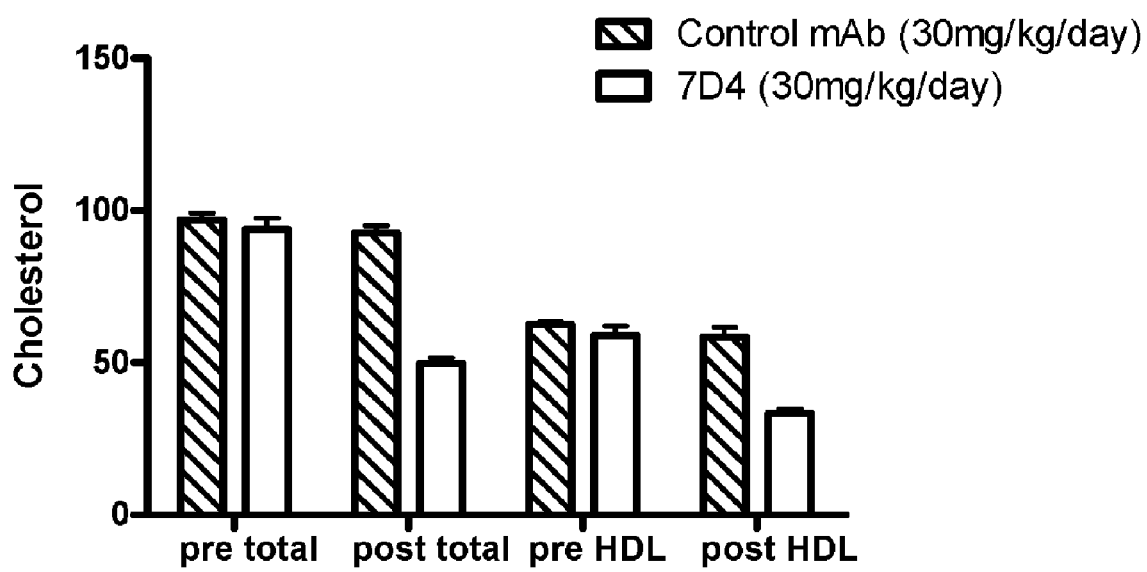
FIG. 6 illustrates the effect of anti-PCSK9 monoclonal antibody 7D4 on blood cholesterol levels in mice.

2. Effect of PCSK9 Specific Antibodies as PCSK9 Antagonist In Vivo a. PCSK9 Antagonist Antibodies Lower Serum Cholesterol in Mice To determine if PCSK9 antagonist monoclonal antibodies can affect cholesterol levels in vivo by inhibiting the function of extracellular PCSK9, the effect of 7D4 was tested against mouse PCSK9 in vitro, on serum cholesterol when injected into mice. 6 to 7 week old male C57/bl6 mice were kept on a 12 hr light/dark cycle, bled to collect approximately 70 µl serum on day −7. Antagonist PCSK9 antibody 7D4, and a control isotype matching monoclonal antibody were injected into male 7 week old C57/bl6 mice via i.p. injections on days 0, 1, 2, and 3. Mice were sacrificed on day 4 without fasting, and serum samples were collected. All frozen serum samples were sent to IDEXX laboratories for total cholesterol, triglyceride, HDL cholesterol and LDL cholesterol measurements. FIG. 6 shows that 7D4 lowered serum cholesterol by 48%, while the control antibody did not have any significant

TABLE 7

Blocking PCSK9 Antibodies and Antigen-binding CDR Sequences according to Kabat (underlined) and Chotia (bold).

| | VL CDR1 | VL CDR2 | VL CDR3 |
|---|---|---|---|
| 4A5 | KASQNVGTNVA (SEQ ID NO: 27) | SASYRYS (SEQ ID NO: 28) | QQFYSYPYT (SEQ ID NO: 29) |
| 5A10 | KASQDVSTAVA (SEQ ID NO: 30) | SASYRYT (SEQ ID NO: 12) | QQRYSTPRT (SEQ ID NO: 31) |
| 6F6 | SASQGISNYLN (SEQ ID NO: 32) | YTSSLHS (SEQ ID NO: 33) | QQYSKLPFT (SEQ ID NO: 55) |
| 7D4 | KASQDVSNALA (SEQ ID NO: 34) | SASYRYT (SEQ ID NO: 12) | QQHYSTPWT (SEQ ID NO: 35) |
| L1L3 | RASQGISSALA (SEQ ID NO: 11) | SASYRYT (SEQ ID NO: 12) | QQRYSLWRT (SEQ ID NO: 13) |
| 4A5 | GYTFTDYYMN (SEQ ID NOs: 56(whole), 36 and 37) | DINPNNGGTTYNQKFKG (SEQ ID NOs: 38 and 39) | WLLFAY (SEQ ID NO: 40) |
| 5A10 | GYTFTSYWMH (SEQ ID NOs: 57(whole), 41 and 42) | EINPSNGRTNYNEKFKS (SEQ ID NO: 43 and 44) | ERPLYAMDY (SEQ ID NO: 45) |
| 6F6 | GYTFTDYYMN (SEQ ID NOs: 56(whole), 36 and 37) | DINPNNGGTSYNQKFKG (SEQ ID NO: 38 and 46) | GGIYYRYDRNYFDY (SEQ ID NO: 47) |
| 7D4 | GFTFSDYYMA (SEQ ID NOs: 58(whole), 48 and 49) | NINYDGSNTSYLDSLKS (SEQ ID NOs: 50 and 51) | EKFAAMDY (SEQ ID NO: 52) |
| L1L3 | GYTFTSYYMH SEQ ID NOs: 59(whole), 60, and 8. | EISPFGGRTNYNEKFKS (SEQ ID NO: 9 and 61) | ERPLYASDL (SEQ ID NO: 10) |

Anti-PCSK9 IgGs 4A5, 5A10 and 6F6 were amine coupled to the Biacore chip. hPCSK9 (100 nM) was mixed with 500 nM of 4A5, 5A10, 6F6 or 7D4 in various ratios and injected for 1 min at 10 µl/min. The four antibodies mutually blocked one another irrespective of the assay orientation tested, suggesting that they all bind to competing epitopes. In contrast, they are able to form sandwich complexes with other non-fully-blocking antibodies that were mapped to specific regions using synthetic peptides.

affect. Both the amount and percentage of reduction are similar to what was reported for PCSK9−/− mice (PCSK9 knockout mice), suggesting that one can achieve complete or near complete inhibition of PCSK9 function through blocking extracellular PCSK9 only, and that intracellular PCSK9 plays little or no role in down-regulating LDLR under normal physiological conditions. As expected, liver LDLR levels were induced in animals treated with 7D4 compared to those treated with a control antibody (FIG. 6).

b. A Partially Blocking Antibody Had No Effect on Blood Cholesterol Levels

Figure 7:
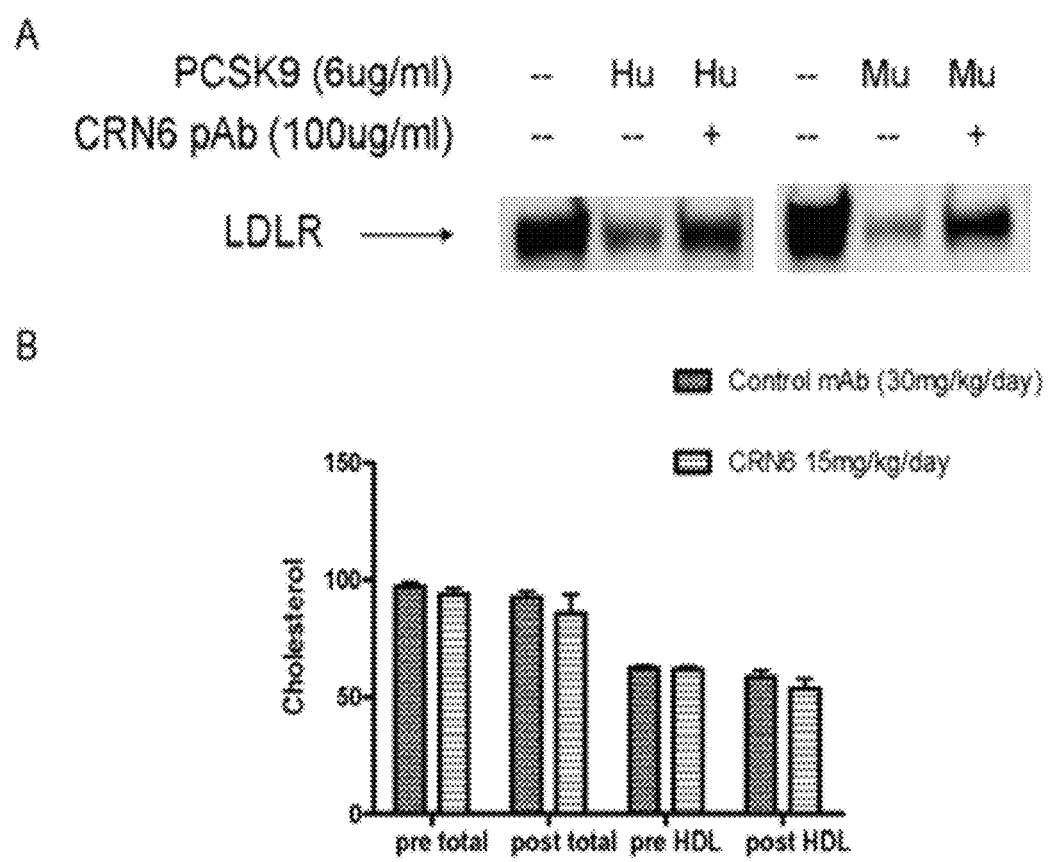
FIG. 7 illustrates (A) the effect of a partial antagonist polyclonal anti-PCSK9 mAb CRN6 on LDLR down regulation and (B) the lack of effect on cholesterol levels in mice.

FIG. 7 illustrates that a partial antagonist polyclonal anti-PCSK9 mAb CRN6 does not affect cholesterol levels in mice. Two groups of 8 week old C57/bl6 mice (n=10 mice/group) were bled and tested for cholesterol levels on day −7; dosed with 15 mg/kg/day of CRN6 or a control antibody by i.v. administration on days 0, 1, 2 and 3; and then bled and tested for cholesterol levels 24 hrs after the final dose. FIG. 7A shows that CRN6 antibody partially blocks PCSK9 mediated down regulation of LDLR in Huh7 cells in vitro. FIG. 7B shows that administration of CRN6 antibody does not affect serum cholesterol levels in mice.

c. Prolonged Effect on Serum Cholesterol by Antagonist PCSK9 mAb in Mice.

Figure 8:
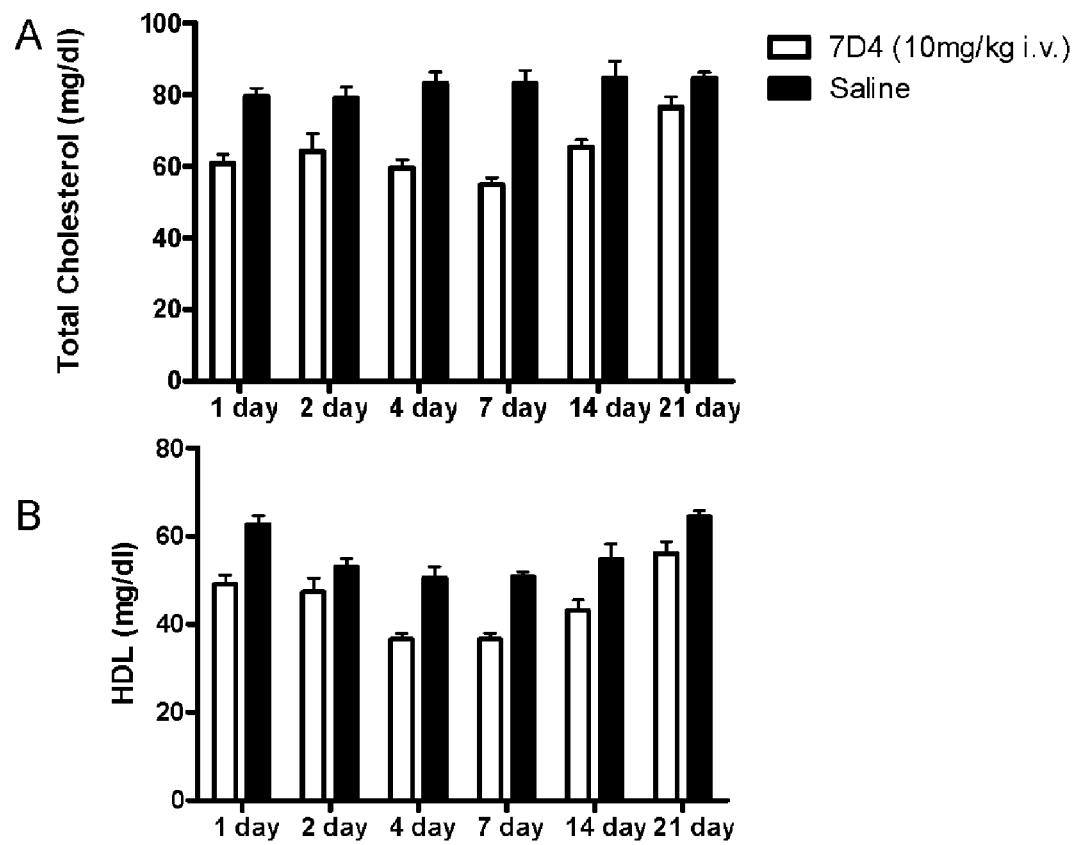
FIG. 8 illustrates the time course of the cholesterol lowering effect obtained using anti-PCSK9 antagonist antibody 7D4 in mice.

A time course study was performed to determine the time of onset and duration of the cholesterol lowering effect of PCSK9 antagonist antibodies in mice. MAb 7D4 or saline control were each injected i.v. at 10 mg/kg or 3 ml/kg in 48 6-week-old C57/bl6 mice. Eight mice from each treatment group were sacrificed on days 1, 2, 4, 7, 14 and 21 after injection. A single injection of 7D4 produced a fast and prolonged lowering effect on serum cholesterol. A 25% reduction in serum cholesterol was seen at 24 hrs after injection. See FIG. 8. Maximum drop of serum cholesterol was observed at the 7 day time point. At 21 days, the reduction in cholesterol is no longer statistically significant. Part B) shows HDL cholesterol. LDL cholesterol levels were very low.

Figure 9:
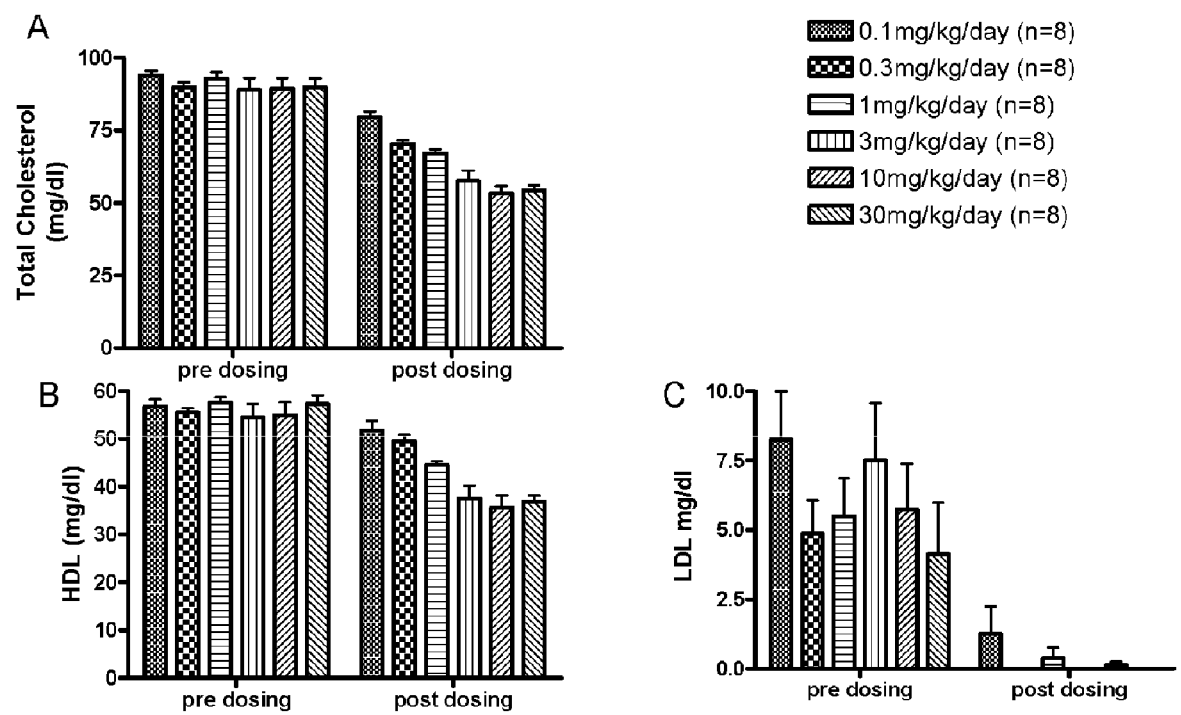
FIG. 9 illustrates the dose dependence of the anti-PCSK9 antagonist mAb 7D4 on the reduction of serum total cholesterol, HDL and LDL in mice.

FIG. 9 illustrates that the anti-PCSK9 antagonist mAb 7D4 dose dependently reduces serum total cholesterol, HDL, and LDL in mice. Six groups of 8 week old C57/bl6 mice (n=8/group) were bled and tested for basal cholesterol levels on day −7 and administered with the indicated doses of antibodies or saline on days 0, 1, 2, and 3 by i. p. bolus injection. Serum samples were collected and tested for cholesterol levels 24 hrs after the last dose. FIG. 9A shows total cholesterol levels, which decreased to less than 60% of control after administration of 3 to 30 mg/kg/day. The maximal effect on total cholesterol was seen at 10 mg/kg, and statistically significant reduction at 1 mg/kg. FIG. 9B shows HDL levels, which decreased to less than 70% after administration of 3 to 30 mg/kg/day. FIG. 9C shows LDL levels, which decreased to nearly zero at all tested doses of 0.3 mg/kg/day and above.

d. Dose Response of Antagonist Antibodies Specific to PCSK9 in Mice

Figure 10:
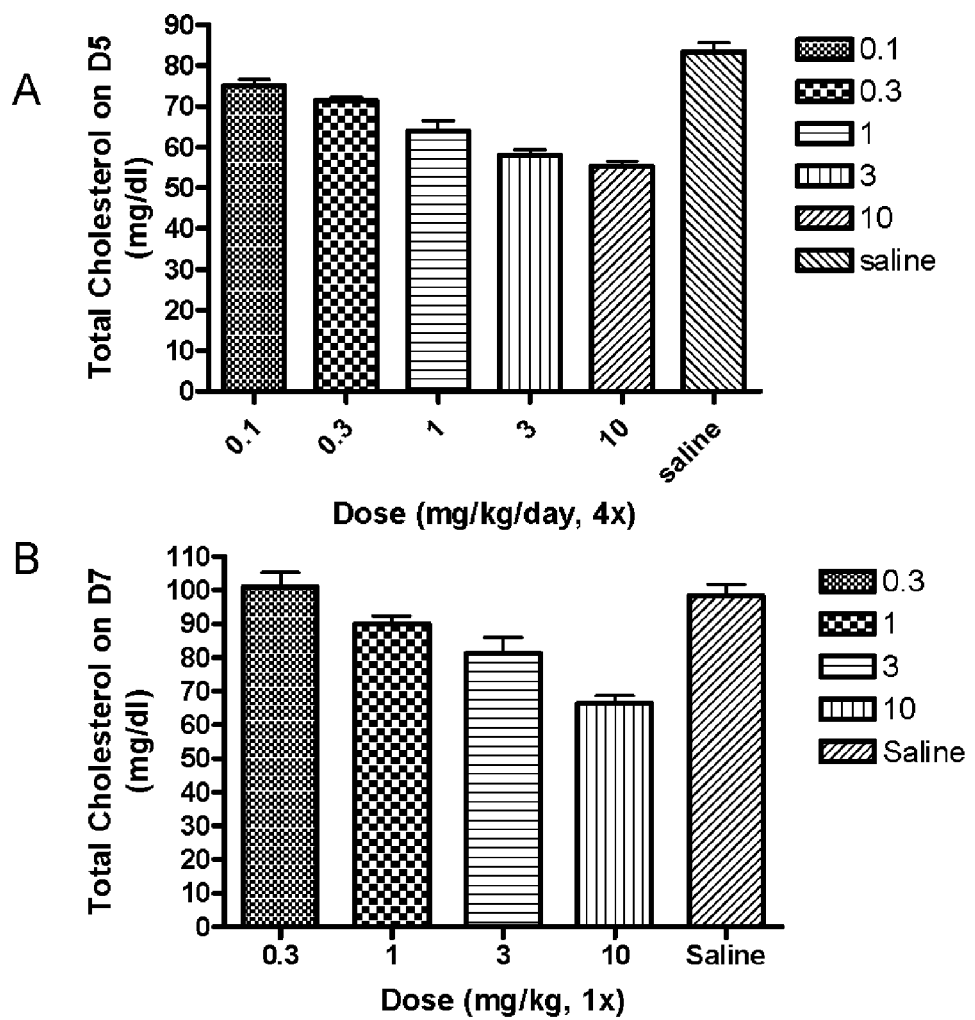
FIG. 10 illustrates the dose dependence of the cholesterol lowering effect of anti-PCSK9 antagonist antibody 5A10 in mice.

FIG. 10 illustrates that anti-PCSK9 antagonist antibody 5A10 dose dependently lowers cholesterol levels in mice. FIG. 10A shows six groups of 8 week old C57/bl6 mice (n=8/group) to which were administered the indicated doses of antibodies or saline daily on days 0, 1, 2, and 3 by i.v. bolus injection. Serum samples were collected and tested for cholesterol levels 24 hrs after the last dose and showed a graduated decrease with increasing dose of antibody. FIG. 10B shows five groups of 8 week old C57/bl6 mice (n=8/group) to which were administered the indicated doses of antibodies or saline on day 0 by i. p. bolus injection. Serum samples were collected and tested for cholesterol levels on day 7 and also showed a graduated decrease with increasing doses of antibody.

Figure 11:
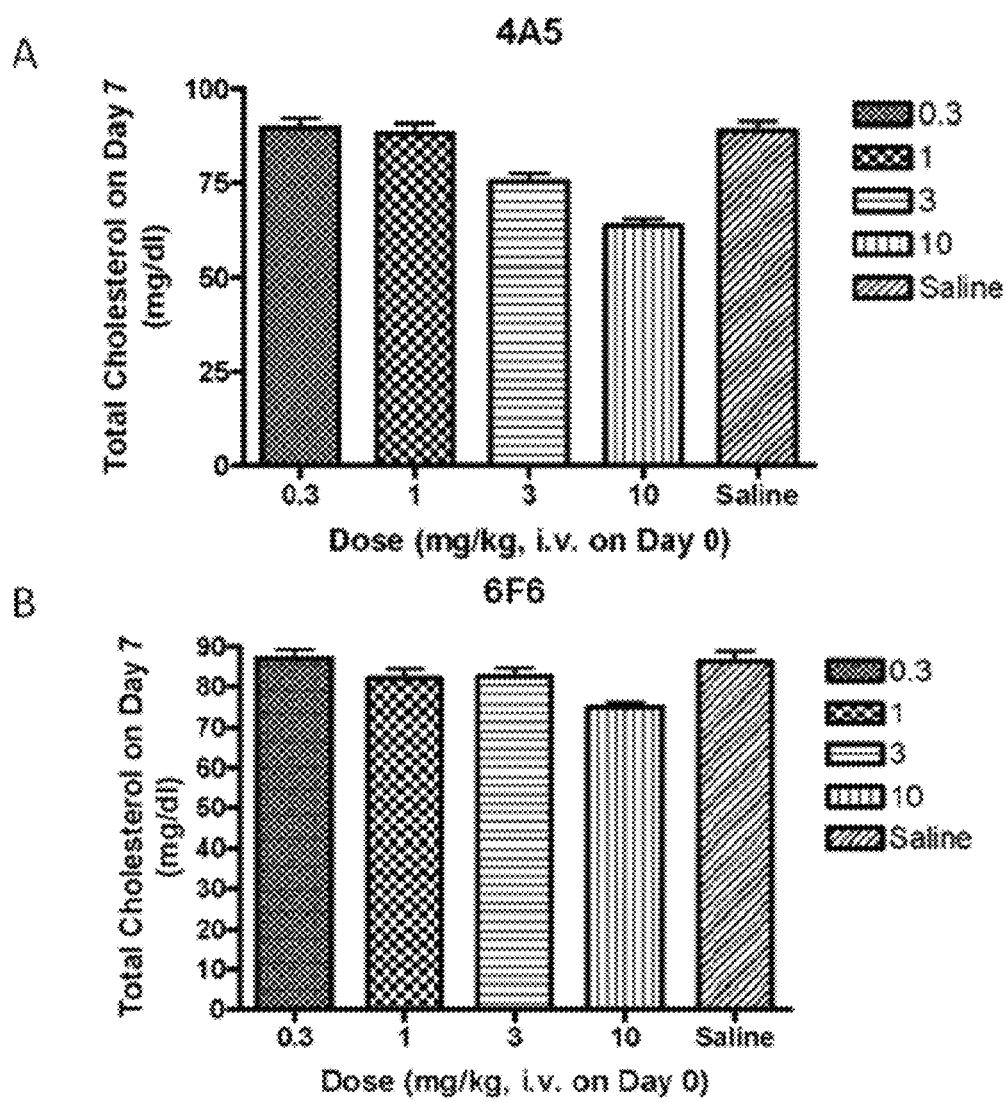
FIG. 11 illustrates the dose dependence of the cholesterol lowering effect of anti-PCSK9 antagonist antibodies (A) 4A5 and (B) 6F6 in mice.

FIG. 11 illustrates that anti-PCSK9 antagonist antibodies 4A5 and 6F6 lower cholesterol levels in mice in a dose-dependent fashion. Eight week old C57/bl6 mice (n=8/group) were administered the indicated doses of antibodies or saline on day 0 by i.p. bolus injection. Serum samples were collected and tested for cholesterol levels on day 7. In FIG. 11A, the antibody 4A5 showed a graduated decrease in total serum cholesterol with increasing dose of antibody. In FIG. 11B, the antibody 6F6 showed decrease in total serum cholesterol at 10 mg/kg/day.

Figure 12:
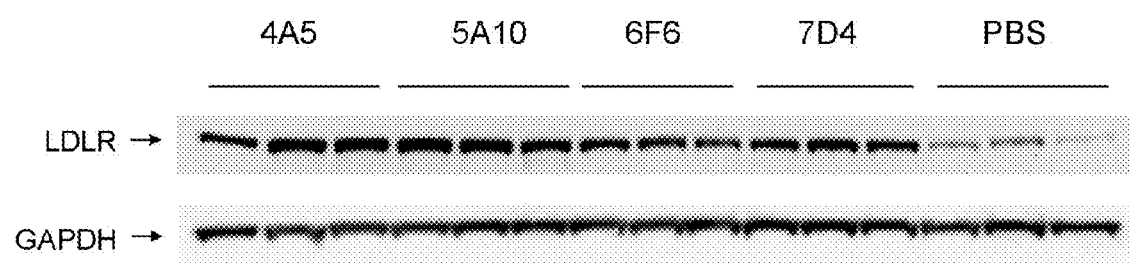
FIG. 12 depicts Western blots of anti-PCSK9 antagonist antibodies effect on liver LDLR levels.

Anti-PCSK9 antagonist antibodies 4A5, 5A10, 6F6 and 7D4 increase liver LDLR levels in mice as found by Western blot analysis. See FIG. 12. For 4A5, 5A10 and 6F6, 8 week old C57/bl6 mice were administered with 10 mg/kg of antibodies or saline on day 0 by i.v. bolus injection, animals were sacrificed on day 7, and whole liver lysate of 3 individual animals were analyzed for LDLR and GAPDH protein levels by Western. For 7D4, 8 week old Bl6/c57 mice were administered with 10 mg/kg of antibodies on days 0, 1, 2, and 3 via i. p. bolus injection, animals were sacrificed on day 4, and whole liver lysate of 3 individual animals were analyzed for LDLR and GAPDH protein levels by Western blot. All antibody-treated mice showed high levels of LDLR as compared to the PBS control mice.

Figure 13:
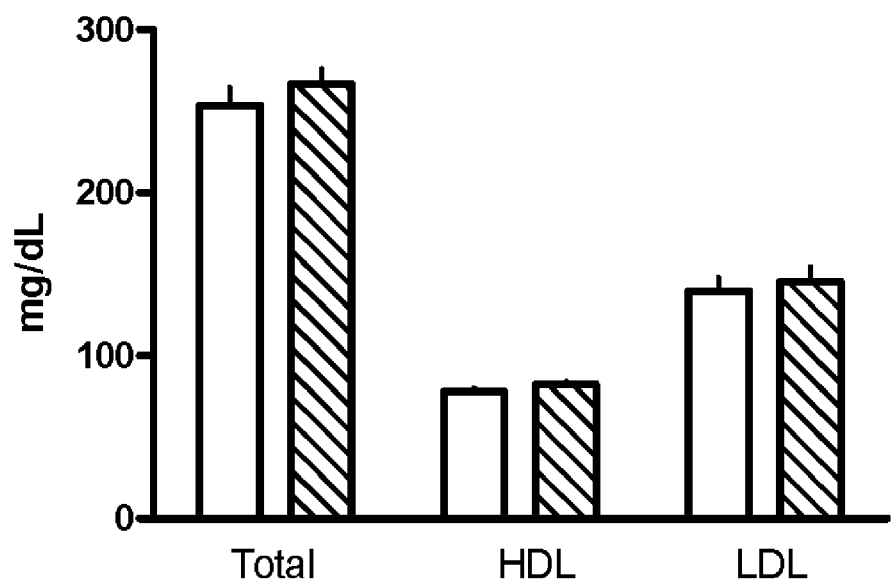
FIG. 13 illustrates the lack of effect of anti-PCSK9 antagonist antibody 4A5 in an LDLR−/− mouse model.

FIG. 13 illustrates that anti-PCSK9 antagonist antibody has no effect in the LDLR−/− mouse. Eight week old LDLR−/− mice (LDLR KO mice) were administered 10 mg/kg 4A5 or saline on day 0 by i.p. bolus injection. Serum samples (from n=9-10 mice) were collected and tested for cholesterol levels on day 7. Administration of the antibody did not appreciably alter the levels of total serum cholesterol, HDL, or LDL.

Figure 14:
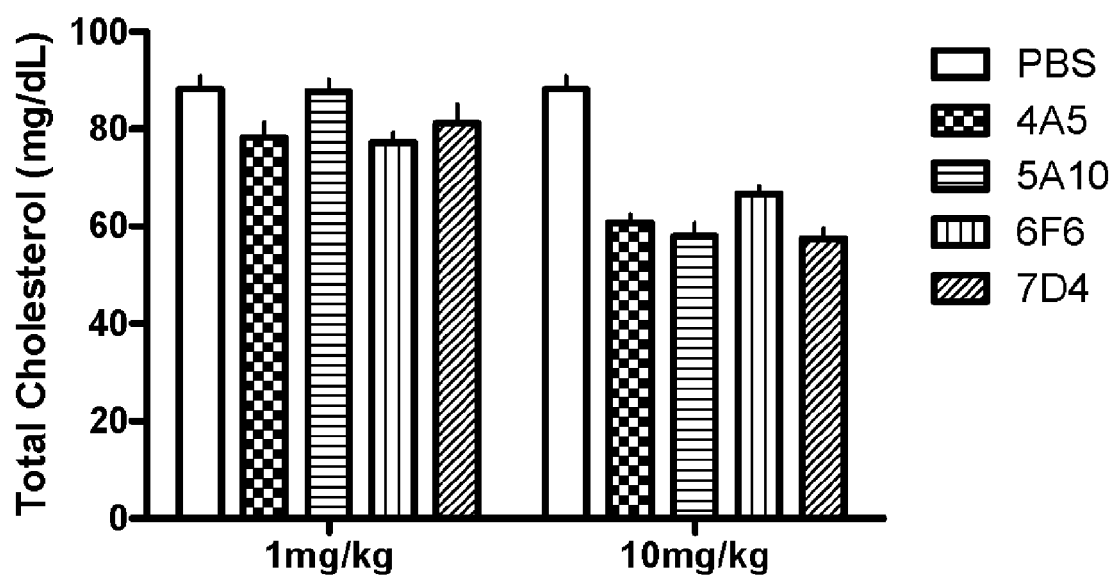
FIG. 14 illustrates the effect on total serum cholesterol of multiple administrations of anti-PCSK9 antagonist antibodies in mice over a longer time course than seen with a single dose.

FIG. 14 illustrates that multiple treatments of anti-PCSK9 antagonist antibodies in mice can substantially decrease total serum cholesterol. Eight week old C57/bl6 mice were administered the indicated doses of antibodies or PBS on days 0, 7, 14 and 21 by i.v. bolus injection. Serum samples (n=5-11 mice) were collected and tested for cholesterol levels on day 28.

Example 8

PCSK9 Antagonist Antibodies Lower Serum LDL in Non-human Primates

Figure 15:
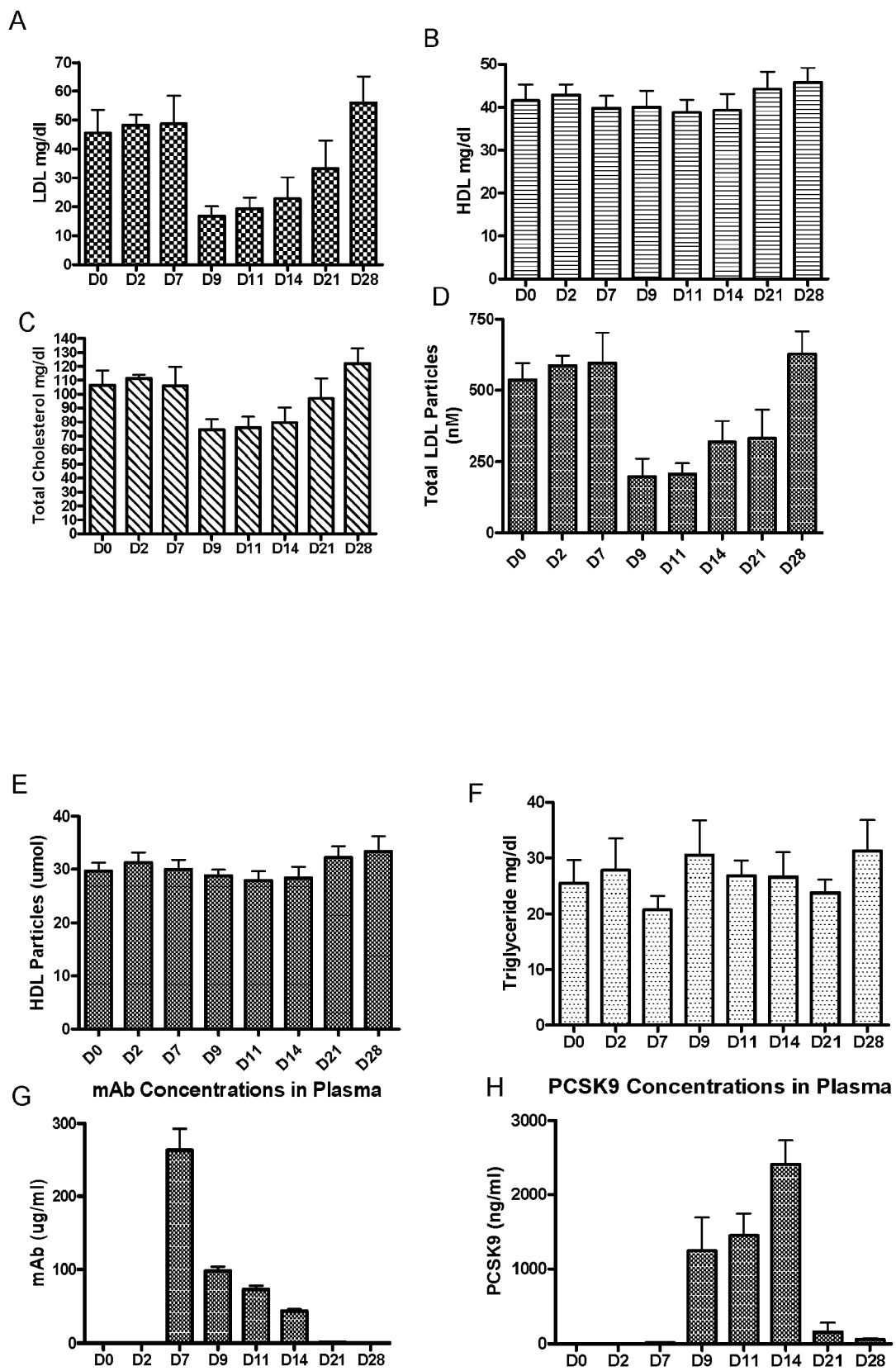
FIG. 15 illustrate the time course of the effects of anti-PCSK9 antagonistic antibody 7D4 on lipid parameters in a cynomolgus monkey model.

To test the in vivo effect of antibodies to PCSK9, antibody 7D4 was tested in cynomolgus monkeys. Four 3-4 year old cynomolgus monkey were injected with vehicle (PBS+0.01% Tween 20) on day 0, and 10 mg/kg 7D4 on day 7. Plasma lipid profiles were analyzed on days 0, 2, 7, 9, 11, 14, 21 and 28 following overnight fasting. A single injection of 10 mg/kg 7D4 produced a dramatic reduction in plasma LDL (60%) (FIG. 15A) and LDL particle numbers (FIG. 15D) in all 4 animals, while having minimal effect on their HDL levels (FIG. 15B) and HDL particle numbers (FIG. 15E). Total cholesterol (FIG. 15C) was also reduced following 7D4 treatment, while triglyceride level (FIG. 15F) was not significantly affected. Total 7D4 (G), and total PCSK9 levels (H) were also measured.

Figure 16:
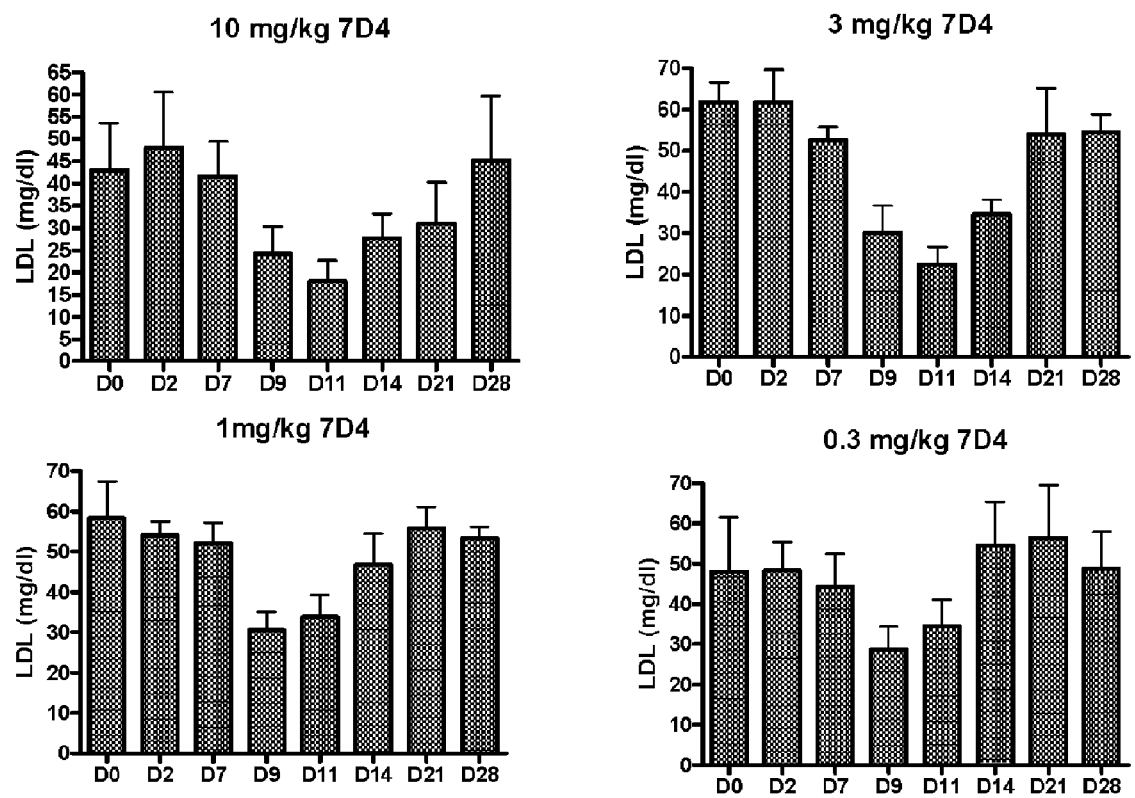
FIG. 16 illustrates the dose- and time-response of anti-PCSK9 antagonistic antibody 7D4 on serum cholesterol levels in the cynomolgus monkey.

FIG. 16 illustrates the dose-response of anti-PCSK9 antibody 7D4 on serum cholesterol levels in the cynomolgus monkey. Two male and two female cynomolgus monkeys 3-5 years of age in each group were given the indicated dose of 7D4 on day 7 and an equal volume of saline on day 0 by i.v. bolus injection. Plasma samples were taken at indicated time points and plasma LDL levels were measured.

Figure 17:
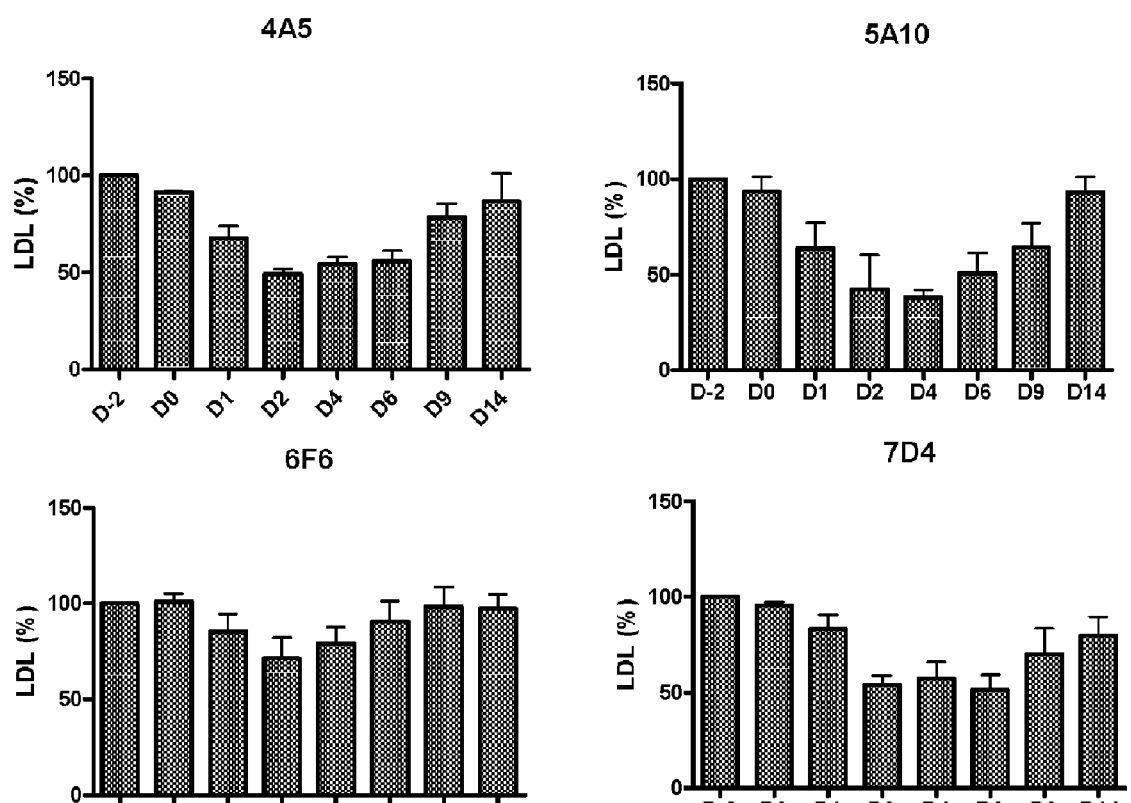
FIG. 17 illustrates a comparison of anti-PCSK9 antagonistic antibodies 4A5, 5A10, 6F6 and 7D4 on serum cholesterol levels in the cynomolgus monkey.

FIG. 17 illustrates a comparison of anti-PCSK9 antibodies 4A5, 5A10, 6F6 and 7D4 on serum cholesterol levels in the cynomolgus monkey. Two male and two female cynomolgus monkeys 3-6 years of age in each group were given 1 mg/kg of the indicated antibody on day 0 by i.v. bolus injection. Plasma samples were taken at indicated time points, plasma LDL levels were measured and normalized to that on day −2.

Figure 18:
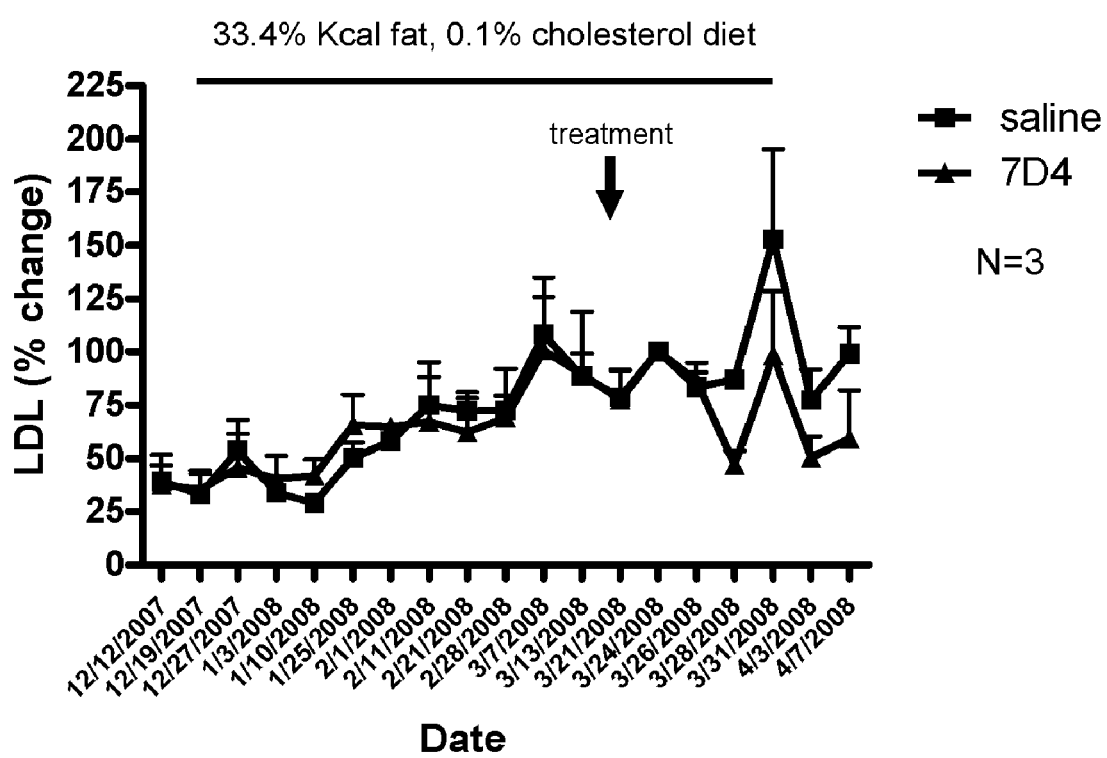
FIG. 18 illustrates the time course of the effect of anti-PCSK9 antagonist antibody 7D4 on plasma cholesterol levels of cynomolgus monkeys fed a 33.4% kcal fat diet supplemented with 0.1% cholesterol.

FIG. 18 illustrates the effect of anti-PCSK9 antagonist antibody 7D4 on plasma cholesterol levels of cynomolgus monkeys fed a 33.4% kcal fat diet supplemented with 0.1% cholesterol. Six 3-5 year old cynomolgus monkeys were put on high-fat diet for 16 weeks. Three monkeys were treated with 10 mg/kg 7D4 and three with saline on the indicated date. LDL levels of individual monkeys were measured and normalized to that of the treatment day.

Example 9

Humanized Anti-PCSK9 Antibody

Figure 19:
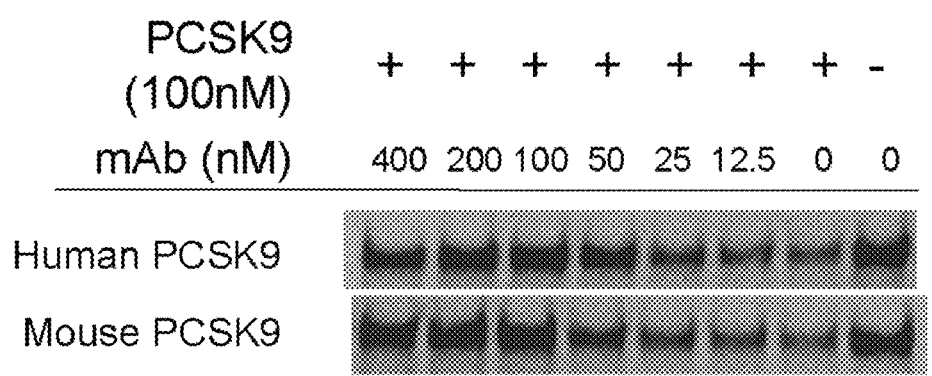
FIG. 19 illustrates the effect of L1L3 (humanized anti-PCSK9 monoclonal antibody) on down regulation of LDLR in Huh7 cells.

The murine monoclonal antibody 5A10 was humanized and affinity matured to provide the L1L3 antibody. L1L3 has an affinity for murine PCSK9 of 200 pM and an affinity for human PCSK9 of 100 pM when measured by Biacore. L1L3 completely inhibits the PCSK9-mediated down regulation of LDLR in cultured Huh7 cells when incubated with 100 nM human or murine PCSK9 antibody. See FIG. 19.

Figure 20:
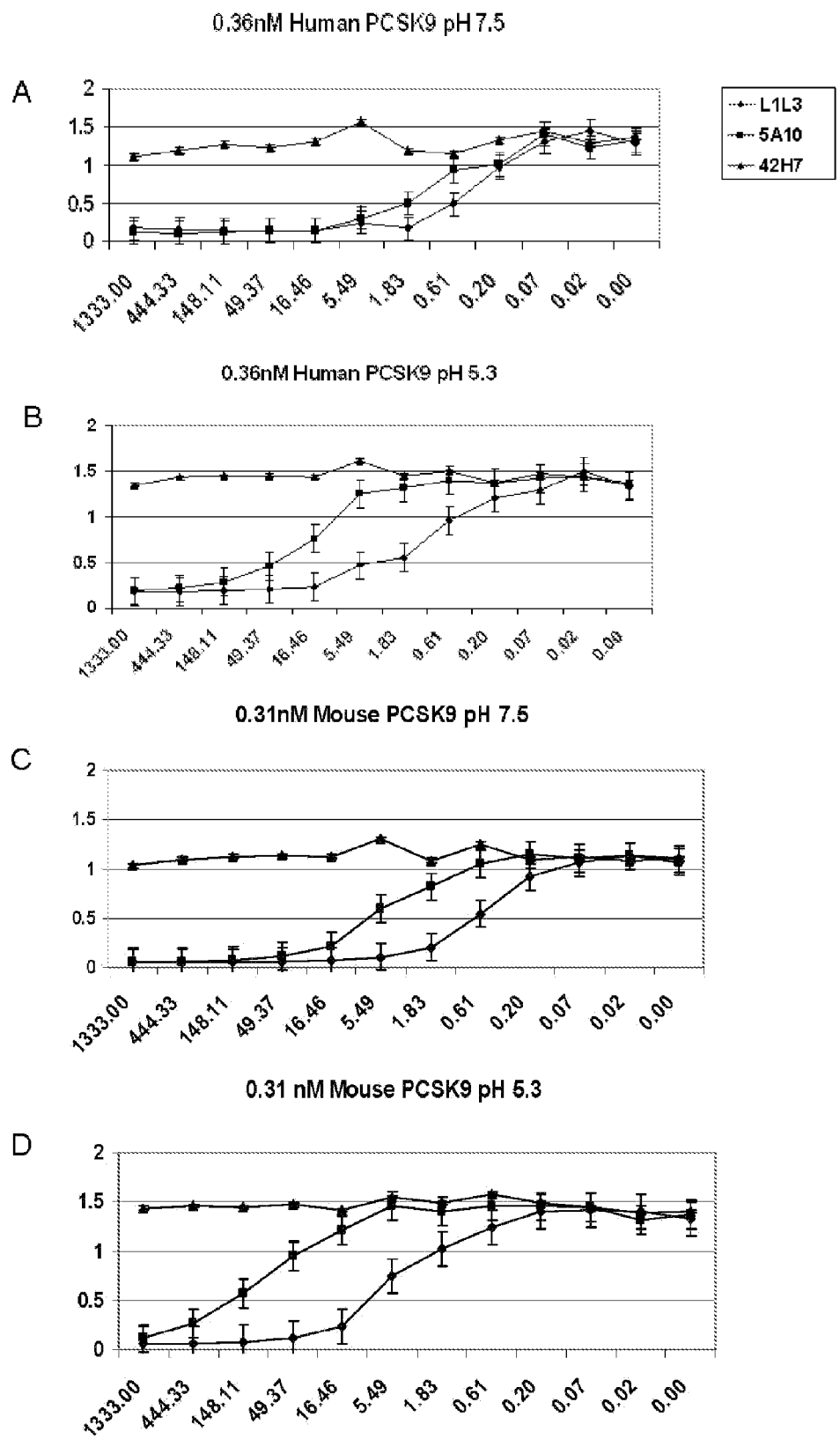
FIG. 20 illustrates the dose-response of L1L3 humanized antibody, the mouse precursor 5A10, and negative control antibody 42H7 on blocking the binding of recombinant biotinylated human PCSK9 (A and B) and mouse PCSK9 (C and D) to immobilized recombinant LDLR extracellular domain in vitro at pH 7.5 (A and C) and pH 5.3 (B and D).

FIG. 20 illustrates the dose-response of L1L3, mouse precursor 5A10, and negative control antibody 42H7 to block the binding of recombinant biotinylated human PCSK9 and mouse PCSK9 to immobilized recombinant LDLR extracellular domain in vitro. FIG. 20A shows human PCSK9 binding to human LDLR extracellular domain at pH 7.5. FIG. 20B shows human PCSK9 binding to human LDLR extracellular domain at pH 5.3. FIG. 20C shows mouse PCSK9 binding to human LDLR extracellular domain at pH 7.5. FIG. 20D shows mouse PCSK9 binding to human LDLR extracellular domain at pH 5.3.

Figure 21:
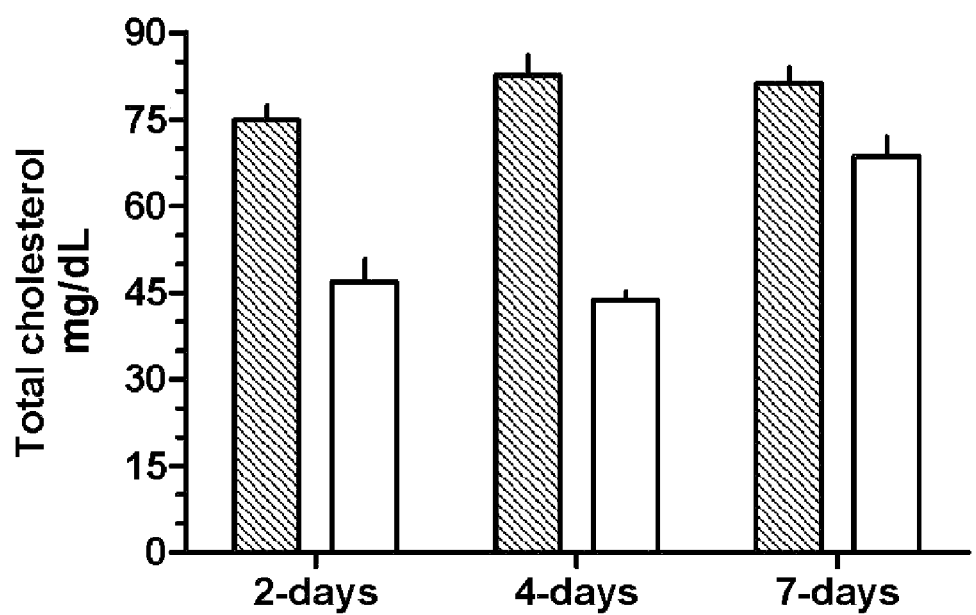
FIG. 21 illustrates the effect on serum cholesterol of treatment of mice with 10 mg/kg L1L3.

FIG. 21 shows the effect on serum cholesterol of treatment with 10 mg/kg L1L3 in mice. Two groups (n=8/group) of 8 week old C57/bl6 mice were dosed with 10 mg/kg L1L3 or an equal volume of saline by i. p. injection on day O, Serum samples were collected and assayed for cholesterol levels on days 2, 4 and 7. L1L3 decreased total serum cholesterol by about 40% at days 2 and 4. In another study, when 10 mg/kg of L1L3 was administered as a single intraperitoneal (IP) dose to C57BL/6 mice fed a normal diet (n=10), serum cholesterol levels were reduced by 47% compared to saline treated controls, 4 days post treatment. When L1L3 was administered as a single IP dose at 0, 0.1, 1, 10 and 80 mg/kg (n=6/group) in a dose-response experiment in male Sprague-Dawley rats fed a normal diet, serum cholesterol levels were dose-dependently reduced, with maximum effect of 50% seen at 10 and 80 mg/kg, 48 hours post dosing. The duration of the cholesterol repression was also dose dependent, ranging from 1 to 21 days.

The amino acid sequence of L1L3 fully humanized heavy chain (SEQ ID NO:15) is shown in Table 8. The sequence of the variable region is underlined (SEQ ID NO: 54).

TABLE 8

| | | | | |
|---|---|---|---|---|
| <u>qvqlvqsgae</u> | <u>vkkpgasvkv</u> | <u>sckasgytft</u> | <u>syymhwvrqa</u> | 60 |
| <u>pgqglewmge</u> | <u>ispfqgrtny</u> | | | |
| <u>nekfksrvtm</u> | <u>trdtststvy</u> | <u>melsslrsed</u> | <u>tavyycarer</u> | 120 |
| <u>plyasdlwgq</u> | <u>gttvtvssas</u> | | | |
| tkgpsvfpla | pcsrstsest | aalgclvkdy | fpepvtvswn | 180 |
| sgaltsgvht | fpavlqssgl | | | |
| yslssvvtvp | ssnfgtqtyt | cnvdhkpsnt | kvdktverkc | 240 |
| cvecppcpap | pvagpsvflf | | | |

TABLE 8-continued

| | | | | |
|---|---|---|---|---|
| ppkpkdtlmi | srtpevtcvv | vdvshedpev | qfnwyvdgve | 300 |
| vhnaktkpre | eqfnstfrvv | | | |
| svltvvhqdw | lngkeykckv | snkglpssie | ktisktkgqp | 360 |
| repqvytlpp | sreemtknqv | | | |
| sltclvkgfy | psdiavewes | ngqpennykt | tppmldsdgs | 420 |
| fflyskltvd | ksrwqqgnvf | | | |
| scsvmhealh | nhytqkslsl | spgk | | 444 |

The amino acid sequence of L1L3 fully humanized light chain (SEQ ID NO:14) is shown in Table 9. The variable region is underlined (SEQ ID NO: 53).

TABLE 9

| | | | | |
|---|---|---|---|---|
| <u>diqmtqspss</u> | <u>lsasvgdrvt</u> | <u>itcrasqgis</u> | <u>salawyqqkp</u> | 60 |
| <u>gkapklliys</u> | <u>asyrytqvps</u> | | | |
| <u>rfsgsgsgtd</u> | <u>ftftisslqp</u> | <u>ediatyycqq</u> | <u>ryslwrtfgq</u> | 120 |
| <u>gtkleikrtv</u> | aapsvfifpp | | | |
| sdeqlksgta | svvcllnnfy | preakvqwkv | dnalqsgnSq | 180 |
| esvteqdskd | styslsstlt | | | |
| lskadyekhk | vyacevthqg | lsspvtksfn | rgec | 214 |

Figure 22:
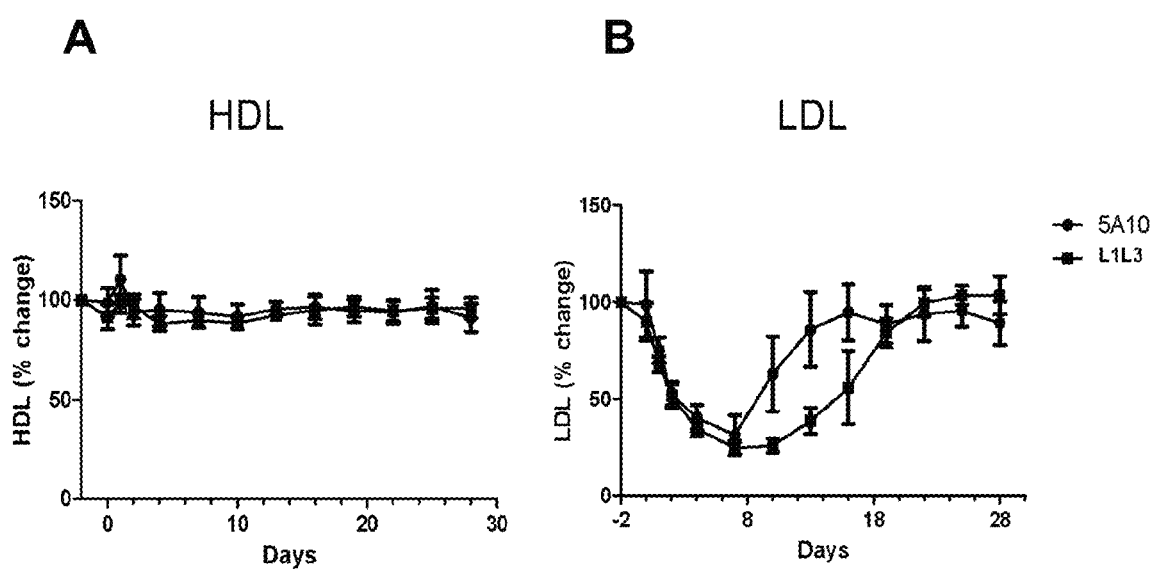
FIG. 22 illustrates the effect of administration of 5A10 antibody or L1L3 to cynomolgus monkeys and measurement of changes in serum HDL (A) and serum LDL (B) as a function of time.

FIG. 22 shows the effect of intravenous administration of an effective dose (3 mg/kg) of antibody 5A10 (solid circles) or antibody L1L3 (solid squares) to each of four cynomolgus monkeys at day zero. The change in serum HDL (FIG. 22A) and serum LDL (FIG. 22B) was measured from −2 to +28 days. Both antibodies resulted in greater than about 70% decrease in serum LDL levels by about seven days, an effect that substantially persisted for about six more days in the animals administered L1L3. All the animals showed normal liver and kidney function and near-normal hematocrits.

L1L3 dose-dependently reduced LDL-C, with a maximum effect observed in the mg/kg group, which maintained a 70% reduction in LDL-C levels until day 21 post-dosing, and fully recovered by day 31. HDL-C levels were not affected by L1L3 treatment in all dose groups. The animals in the 3 mg/kg dose group (n=4) were also given two additional IV doses of 3 mg/kg L1L3 on study days 42 and 56 (2-weeks apart). These two additional doses again lowered LDL-C and maintained LDL-C levels below 50% for 4 weeks. LDL-C levels returned to normal two weeks later. Serum HDL-C levels remained unchanged throughout the study.

The efficacy of L1L3 in non-human primates with hypercholesterolemia and pharmacodynamic interactions between L1L3 and HMG-CoA reductase inhibiting statins were investigated. Prior to the initiation of the study, the LDL-C levels of a cohort of cynomolgus monkeys (n=12) were elevated to an average of 120 mg/dL, compared to the normal average levels of 50 mg/dL, by feeding with a diet containing 35% fat (wt/wt) and 600 ppm cholesterol for over 18 months. Surprisingly, no effect was observed on serum total cholesterol or LDL-C levels after the daily administration of a medium-dose (10 mg/animal) of Crestor® (rosuvastatin calcium) for 6 weeks, and after a subsequent daily administration of high-dose (20 mg/kg) for 2 weeks. A single administration of 3 mg/kg L1L3 with Crestor® or vehicle treatment for 2 weeks, effectively lowered serum LDL-C levels by 56% by day 5 post treatment, and gradually recovered in 2.5 to 3 weeks while not affecting HDL-C levels. Upon switching the animals to daily administration of 50 mg/kg Zocor® (simvastatin), their LDL-C levels reached a maximal reduction of 43% at day 5, and stabilized thereafter. After 3 weeks of 50 mg/kg/day Zocor® administration, these animals were treated with a single dose of 3 mg/kg L1L3 while still receiving 50 mg/kg/day Zocor®. Administration of L1L3 resulted in another additional 65% reduction in LDL-C, in addition to the 43% reduction by Zocor®, by day 5, and returned to pre-dosing levels within 2 weeks.

Other CDR amino acid substitutions were made to 5A10 in the course of humanization and affinity maturation and to achieve particular properties. The sequences of the modified CDRs and the PCSK9 binding abilities of the antibodies containing these modified CDRs are listed in FIGS. 24 A-G. The numbers following each sequence in FIGS. 24 A-G represent the SEQ ID NO for that sequence.

The disclosures of all references cited herein are hereby incorporated by reference herein.

It is claimed:

1. A host cell that recombinantly produces an antibody which specifically binds to PCSK9, wherein the antibody comprises a heavy chain variable region (VH) comprising complementarity determining region one (CDR1), CDR2, and CDR3 of the amino acid sequence shown in SEQ ID NO: 54, and a light chain variable region (VL) comprising CDR1, CDR2, and CDR3 of the amino acid sequence shown in SEQ ID NO: 53.

2. The host cell of claim 1, wherein the antibody comprises:
a VH complementarity determining region one (CDR1) having the amino acid sequence shown in SEQ ID NO:8, 59, or 60, a VH CDR2 having the amino acid sequence shown in SEQ ID NO:9 or 61, and a VH CDR3 having the amino acid sequence shown in SEQ ID NO:10; and
a VL CDR1 having the amino acid sequence shown in SEQ ID NO:11, a VL CDR2 having the amino acid sequence shown in SEQ ID NO:12, and VL CDR3 having the amino acid sequence shown in SEQ ID NO:13.

3. The host cell of claim 2, wherein the antibody comprises:
a VH region comprising the amino acid sequence shown in SEQ ID NO: 54 or a variant thereof with one or several amino acid substitutions in amino acids positions that are not within said CDRs; and
a VL region comprising the amino acid sequence shown in SEQ ID NO: 53 or a variant thereof with one or several amino acid substitutions in amino acids positions that are not within said CDRs.

4. The host cell of claim 3, wherein the antibody further comprises an immunologically inert constant region.

5. The host cell of claim 4, wherein the constant region is aglycosylated Fc.

6. The host cell of claim 4, wherein the antibody has an isotype that is selected from the group consisting of $IgG_2$, $IgG_4$, $IgG_{2\Delta a}$, $IgG_{4\Delta b}$, $IgG_{4\Delta c}$, $IgG_4$ S228P, $IgG_{4\Delta b}$ S228P and $IgG_{4\Delta c}$ S228P.

7. The host cell of claim 3, wherein the antibody comprises a light chain having the amino acid sequence shown in SEQ ID NO:14 and a heavy chain having the amino acid sequence shown in SEQ ID NO:15, with or without the C-terminal lysine of the amino acid sequence shown in SEQ ID NO: 15.

8. An isolated nucleic acid encoding an antibody which specifically binds to PCSK9, wherein the antibody comprises:

a heavy chain variable region (VH) comprising complementarity determining region one (CDR1), CDR2, and CDR3 of the amino acid sequence shown in SEQ ID NO: 54; and
a light chain variable region (VL) comprising CDR1, CDR2, and CDR3 of the amino acid sequence shown in SEQ ID NO: 53.

9. The isolated nucleic acid of claim 8, wherein the antibody comprises:
a VH complementarity determining region one (CDR1) having the amino acid sequence shown in SEQ ID NO:8, 59, or 60, a VH CDR2 having the amino acid sequence shown in SEQ ID NO:9 or 61, and a VH CDR3 having the amino acid sequence shown in SEQ ID NO:10; and
a VL CDR1 having the amino acid sequence shown in SEQ ID NO:11, a VL CDR2 having the amino acid sequence shown in SEQ ID NO:12, and VL CDR3 having the amino acid sequence shown in SEQ ID NO:13.

10. The isolated nucleic acid of claim 9, wherein the antibody comprises:
a VH region comprising the amino acid sequence shown in SEQ ID NO: 54 or a variant thereof with one or several amino acid substitutions in amino acids positions that are not within said CDRs; and
a VL region comprising the amino acid sequence shown in SEQ ID NO: 53 or a variant thereof with one or several amino acid substitutions in amino acids positions that are not within said CDRs.

11. The isolated nucleic acid of claim 10, wherein the antibody further comprises an immunologically inert constant region.

12. The isolated nucleic acid of claim 11, wherein the constant region is aglycosylated Fc.

13. The isolated nucleic acid of claim 11, wherein the antibody has an isotype that is selected from the group consisting of $IgG_2$, $IgG_4$, $IgG_{2\Delta a}$, $IgG_{4\Delta b}$, $IgG_{4\Delta c}$, $IgG_4$ S228P, $IgG_{4\Delta b}$ S228P and $IgG_{4\Delta c}$ S228P.

14. The isolated nucleic acid of claim 10, wherein the antibody comprises a light chain having the amino acid sequence shown in SEQ ID NO:14 and a heavy chain having the amino acid sequence shown in SEQ ID NO:15, with or without the C-terminal lysine of the amino acid sequence shown in SEQ ID NO: 15.

* * * * *